(12) United States Patent
Oe et al.

(10) Patent No.: US 8,551,752 B2
(45) Date of Patent: Oct. 8, 2013

(54) RNA POLYMERASE MUTANT WITH IMPROVED FUNCTIONS

(75) Inventors: Seigo Oe, Ayase (JP); Hiroshi Sato, Ayase (JP); Teruhiko Ide, Ayase (JP)

(73) Assignee: Tosoh Corporation, Yamaguchi (JP)

( * ) Notice: Subject to any disclaimer, the term of this patent is extended or adjusted under 35 U.S.C. 154(b) by 251 days.

(21) Appl. No.: 13/057,418

(22) PCT Filed: Aug. 7, 2009

(86) PCT No.: PCT/JP2009/064323
§ 371 (c)(1),
(2), (4) Date: Feb. 3, 2011

(87) PCT Pub. No.: WO2010/016621
PCT Pub. Date: Feb. 11, 2010

(65) Prior Publication Data
US 2011/0136181 A1    Jun. 9, 2011

(30) Foreign Application Priority Data

Aug. 8, 2008 (JP) .................................. 2008-205491
Feb. 23, 2009 (JP) .................................. 2009-038979
Feb. 23, 2009 (JP) .................................. 2009-038980

(51) Int. Cl.
*C12N 9/12* (2006.01)

(52) U.S. Cl.
USPC ............................. 435/194; 530/350; 435/183

(58) Field of Classification Search
None
See application file for complete search history.

(56) References Cited

U.S. PATENT DOCUMENTS

| | | |
|---|---|---|
| 6,524,828 B1 | 2/2003 | Liao et al. |
| 6,867,027 B1 | 3/2005 | Hayashizaki et al. |
| 7,335,471 B2 | 2/2008 | Guillerez et al. |
| 2003/0175738 A1 | 9/2003 | Sugiyama et al. |

FOREIGN PATENT DOCUMENTS

| | | |
|---|---|---|
| EP | 0939130 A1 | 9/1999 |
| EP | 1403364 A1 | 3/2004 |
| JP | 11-018799 A | 1/1999 |
| JP | 11-075867 A | 3/1999 |
| JP | 2002-532095 A | 10/2002 |
| JP | 2003-525627 A | 9/2003 |
| JP | 2004-535163 A | 11/2004 |
| WO | 01/66705 A1 | 9/2001 |

OTHER PUBLICATIONS

Ngo et al. In the Protein Folding Problem and Tertiary Structure Prediction, 1994, Merz et al. (ed.), Birkhauser, Boston, MA, pp. 433 and 492-495, Ref: U, Form-892.*
Extended Search Report issued Feb. 1, 2013, in corresponding European Patent Application No. 09805098.2.

* cited by examiner

*Primary Examiner* — Richard Hutson
(74) *Attorney, Agent, or Firm* — Sughrue Mion, PLLC

(57) ABSTRACT

Disclosed is a T7 RNA polymerase mutant having improved thermal stability and/or specific activity in comparison with wild-type T7-like bacteriophage RNA polymerase, wherein at least one amino acid residue corresponding to at least one of the amino acid residues selected from the group at least consisting of glutamine at position 768, lysine at position 179 and valine at position 685 of the amino acid sequence that composes wild-type T7 RNA polymerase shown in SEQ ID NO: 6, is substituted with another amino acid.

11 Claims, 12 Drawing Sheets

```
SEQUENCE LISTING

<160> NUMBER OF SEQ ID NOS: 59

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 1
gcacttcatg aacacgatta acatcgc                                            27

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 2
agtgccaagc ttgactttct cagagat                                            27

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 3
gtcaagcttg gcactaaggc actggctgg                                          29

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 4
ctagataagc tttacgcgaa cgcgaagtcc g                                       31

<210> SEQ ID NO 5
<211> LENGTH: 2652
<212> TYPE: DNA
<213> ORGANISM: Bacteriophage T7

<400> SEQUENCE: 5 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15
```

```
gct gct atc ccg ttc aac act ctg gct gac cat tac ggt gag cgt tta      96
Ala Ala Ile Pro Phe Asn Thr Leu Ala Asp His Tyr Gly Glu Arg Leu
        20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
    35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
            85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
            115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac     528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct     576
Val Tyr Lys Lys Ala Phe Met Gln Val Val Glu Ala Asp Met Leu Ser
                180                 185                 190 aag ggt cta ctc ggt ggc gag gcg tgg tct tcg tgg cat aag gaa gac     624
Lys Gly Leu Leu Gly Gly Glu Ala Trp Ser Ser Trp His Lys Glu Asp
                195                 200                 205 tct att cat gta gga gta cgc tgc atc gag atg ctc att gag tca acc     672
Ser Ile His Val Gly Val Arg Cys Ile Glu Met Leu Ile Glu Ser Thr
210                 215                 220 gga atg gtt agc tta cac cgc caa aat gct ggc gta gta ggt caa gac     720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc     768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta     816
Arg Ala Gly Ala Leu Ala Gly Ile Ser Pro Met Phe Gln Pro Cys Val
                260                 265                 270 gtt cct cct aag ccg tgg act ggc att act ggt ggt ggc tat tgg gct     864
Val Pro Pro Lys Pro Trp Thr Gly Ile Thr Gly Gly Gly Tyr Trp Ala
                275                 280                 285 aac ggt cgt cgt cct ctg gcg ctg gtg cgt act cac agt aag aaa gca     912
Asn Gly Arg Arg Pro Leu Ala Leu Val Arg Thr His Ser Lys Lys Ala
            290                 295                 300 ctg atg cgc tac gaa gac gtt tac atg cct gag gtg tac aaa gcg att     960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg    1008
Asn Ile Ala Gln Asn Thr Ala Trp Lys Ile Asn Lys Lys Val Leu Ala
                325                 330                 335
```

```
gtc gcc aac gta atc acc aag tgg aag cat tgt ccg gtc gag gac atc    1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac    1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg    1152
Met Asn Pro Glu Ala Leu Thr Ala Trp Lys Arg Ala Ala Ala Ala Val
            370                 375                 380 tac cgc aag gac aag gct cgc aag tct cgc gtt atc agc ctt gag ttc    1200
Tyr Arg Lys Asp Lys Ala Arg Lys Ser Arg Ile Ser Leu Glu Phe
385                 390                 395                 400 atg ctt gag caa gcc aat aag ttt gct aac cat aag gcc atc tgg ttc    1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc    1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa    1344
Asn Pro Gln Gly Asn Asp Met Thr Lys Gly Leu Leu Thr Leu Ala Lys
            435                 440                 445 ggt aaa cca atc ggt aag gaa ggt tac tac tgg ctg aaa atc cac ggt    1392
Gly Lys Pro Ile Gly Lys Glu Gly Tyr Tyr Trp Leu Lys Ile His Gly
            450                 455                 460 gca aac tgt gcg ggt gtc gat aag gtt ccg ttc cct gag cgc atc aag    1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca    1488
Phe Ile Glu Glu Asn His Glu Asn Ile Met Ala Cys Ala Lys Ser Pro
            485                 490                 495 ctg gag aac act tgg tgg gct gag caa gat tct ccg ttc tgc ttc ctt    1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat    1584
Ala Phe Cys Phe Glu Tyr Ala Gly Val Gln His His Gly Leu Ser Tyr
            515                 520                 525 aac tgc tcc ctt ccg ctg gcg ttt gac ggg tct tgc tct ggc atc cag    1632
Asn Cys Ser Leu Pro Leu Ala Phe Asp Gly Ser Cys Ser Gly Ile Gln
            530                 535                 540 cac ttc tcc gcg atg ctc cga gat gag gta ggt ggt cgc gcg gtt aac    1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag    1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac    1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa    1824
Glu Val Val Thr Val Thr Asp Glu Asn Thr Gly Glu Ile Ser Glu Lys
            595                 600                 605 gtc aag ctt ggc act aag gca ctg gct ggt caa tgg ctg gct tac ggt    1872
Val Lys Leu Gly Thr Lys Ala Leu Ala Gly Gln Trp Leu Ala Tyr Gly
            610                 615                 620 gtt act cgc agt gtg act aag cgt tca gtc atg acg ctg gct tac ggg    1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag    1968
Ser Lys Glu Phe Gly Phe Arg Gln Gln Val Leu Glu Asp Thr Ile Gln
            645                 650                 655
```

```
cca gct att gat tcc ggc aag ggt ctg atg ttc act cag ccg aat cag    2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg    2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag    2112
Val Val Ala Ala Val Glu Ala Met Asn Trp Leu Lys Ser Ala Ala Lys
    690                 695                 700 ctt ctg gct gct gag gtc aaa gat aag aag act gga gag att ctt cgc    2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg    2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
    770                 775                 780 agc caa gac ggt agc cac ctt cgt aag act gta gtg tgg gca cac gag    2400
Ser Gln Asp Gly Ser His Leu Arg Lys Thr Val Val Trp Ala His Glu
785                 790                 795                 800 aag tac gga atc gaa tct ttt gca ctg att cac gac tcc ttc ggt acc    2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                    2652
Ala Phe Ala <210> SEQ ID NO 6
<211> LENGTH: 883
<212> TYPE: PRT
<213> ORGANISM: Bacteriophage T7

<400> SEQUENCE: 6

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
```

```
                65                  70                  75                  80
Met Ile Ala Arg Ile Asn Asp Trp Phe Glu Glu Val Lys Ala Lys Arg
                        85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
                130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

Leu Glu Asn Thr Trp Trp Ala Glu Gln Asp Ser Pro Phe Cys Phe Leu
               500                 505                 510

Ala Phe Cys Phe Glu Tyr Ala Gly Val Gln His His Gly Leu Ser Tyr
         515                 520                 525

Asn Cys Ser Leu Pro Leu Ala Phe Asp Gly Ser Cys Ser Gly Ile Gln
     530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                 565                 570                 575

Lys Val Asn Glu Ile Leu Gln Ala Asp Ala Ile Asn Gly Thr Asp Asn
             580                 585                 590

Glu Val Val Thr Val Thr Asp Glu Asn Thr Gly Glu Ile Ser Glu Lys
         595                 600                 605

Val Lys Leu Gly Thr Lys Ala Leu Ala Gly Gln Trp Leu Ala Tyr Gly
     610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                 645                 650                 655

Pro Ala Ile Asp Ser Gly Lys Gly Leu Met Phe Thr Gln Pro Asn Gln
             660                 665                 670

Ala Ala Gly Tyr Met Ala Lys Leu Ile Trp Glu Ser Val Ser Val Thr
         675                 680                 685

Val Val Ala Ala Val Glu Ala Met Asn Trp Leu Lys Ser Ala Ala Lys
     690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                 725                 730                 735

Gln Glu Tyr Lys Lys Pro Ile Gln Thr Arg Leu Asn Leu Met Phe Leu
             740                 745                 750

Gly Gln Phe Arg Leu Gln Pro Thr Ile Asn Thr Asn Lys Asp Ser Glu
         755                 760                 765

Ile Asp Ala His Lys Gln Glu Ser Gly Ile Ala Pro Asn Phe Val His
     770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                 805                 810                 815

Ile Pro Ala Asp Ala Ala Asn Leu Phe Lys Ala Val Arg Glu Thr Met
             820                 825                 830

Val Asp Thr Tyr Glu Ser Cys Asp Val Leu Ala Asp Phe Tyr Asp Gln
         835                 840                 845

Phe Ala Asp Gln Leu His Glu Ser Gln Leu Asp Lys Met Pro Ala Leu
     850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 7
<211> LENGTH: 28
<212> TYPE: DNA
<213> ORGANISM: Artificial Sequence
<220> FEATURE:

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 7
cacgatgcat ctgaaatgag ctgttgac                                    28

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
atacctaggc tgcagctacg cgaacgcgaa                                  30

<210> SEQ ID NO 9
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 9
atggggcatc atcatcatca tcatatgaac acgattaaca tc                    42

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 10
gtcgatgtct tccggtttca tcggg                                       25

<210> SEQ ID NO 11
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 11
atgatgatga tgatgatgcc ccatggtctg tttcctgtgt g                     41

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 12
gcttccacag caatggcatc ctggtc                                      26

<210> SEQ ID NO 13
<211> LENGTH: 2676
<212> TYPE: DNA
<213> ORGANISM: Artificial Sequence
<220> FEATURE:
<223> OTHER INFORMATION: Synthetic T7 RNA polymerase gene

<400> SEQUENCE: 13 atg ggg cat cat cat cat cat cat atg aac acg att aac atc gct aag    48
Met Gly His His His His His His Met Asn Thr Ile Asn Ile Ala Lys
1               5                   10                  15

```
aac gac ttc tct gac atc gaa ctg gct gct atc ccg ttc aac act ctg        96
Asn Asp Phe Ser Asp Ile Glu Leu Ala Ala Ile Pro Phe Asn Thr Leu
         20                  25                  30 gct gac cat tac ggt gag cgt tta gct cgc gaa cag ttg gcc ctt gag       144
Ala Asp His Tyr Gly Glu Arg Leu Ala Arg Glu Gln Leu Ala Leu Glu
     35                  40                  45 cat gag tct tac gag atg ggt gaa gca cgc ttc cgc aag atg ttt gag       192
His Glu Ser Tyr Glu Met Gly Glu Ala Arg Phe Arg Lys Met Phe Glu
 50                  55                  60 cgt caa ctt aaa gct ggt gag gtt gcg gat aac gct gcc gcc aag cct       240
Arg Gln Leu Lys Ala Gly Glu Val Ala Asp Asn Ala Ala Ala Lys Pro
65                  70                  75                  80 ctc atc act acc cta ctc cct aag atg att gca cgc atc aac gac tgg       288
Leu Ile Thr Thr Leu Leu Pro Lys Met Ile Ala Arg Ile Asn Asp Trp
             85                  90                  95 ttt gag gaa gtg aaa gct aag cgc ggc aag cgc ccg aca gcc ttc cag       336
Phe Glu Glu Val Lys Ala Lys Arg Gly Lys Arg Pro Thr Ala Phe Gln
        100                 105                 110 ttc ctg caa gaa atc aag ccg gaa gcc gta gcg tac atc acc att aag       384
Phe Leu Gln Glu Ile Lys Pro Glu Ala Val Ala Tyr Ile Thr Ile Lys
    115                 120                 125 acc act ctg gct tgc cta acc agt gct gac aat aca acc gtt cag gct       432
Thr Thr Leu Ala Cys Leu Thr Ser Ala Asp Asn Thr Thr Val Gln Ala
130                 135                 140 gta gca agc gca atc ggt cgg gcc att gag gac gag gct cgc ttc ggt       480
Val Ala Ser Ala Ile Gly Arg Ala Ile Glu Asp Glu Ala Arg Phe Gly
145                 150                 155                 160 cgt atc cgt gac ctt gaa gct aag cac ttc aag aaa aac gtt gag gaa       528
Arg Ile Arg Asp Leu Glu Ala Lys His Phe Lys Lys Asn Val Glu Glu
                165                 170                 175 caa ctc aac aag cgc gta ggg cac gtc tac aag aaa gca ttt atg caa       576
Gln Leu Asn Lys Arg Val Gly His Val Tyr Lys Lys Ala Phe Met Gln
            180                 185                 190 gtt gtc gag gct gac atg ctc tct aag ggt cta ctc ggt ggc gag gcg       624
Val Val Glu Ala Asp Met Leu Ser Lys Gly Leu Leu Gly Gly Glu Ala
        195                 200                 205 tgg tct tcg tgg cat aag gaa gac tct att cat gta gga gta cgc tgc       672
Trp Ser Ser Trp His Lys Glu Asp Ser Ile His Val Gly Val Arg Cys
    210                 215                 220 atc gag atg ctc att gag tca acc gga atg gtt agc tta cac cgc caa       720
Ile Glu Met Leu Ile Glu Ser Thr Gly Met Val Ser Leu His Arg Gln
225                 230                 235                 240 aat gct ggc gta gta ggt caa gac tct gag act atc gaa ctc gca cct       768
Asn Ala Gly Val Val Gly Gln Asp Ser Glu Thr Ile Glu Leu Ala Pro
                245                 250                 255 gaa tac gct gag gct atc gca acc cgt gca ggt gcg ctg gct ggc atc       816
Glu Tyr Ala Glu Ala Ile Ala Thr Arg Ala Gly Ala Leu Ala Gly Ile
            260                 265                 270 tct ccg atg ttc caa cct tgc gta gtt cct cct aag ccg tgg act ggc       864
Ser Pro Met Phe Gln Pro Cys Val Val Pro Pro Lys Pro Trp Thr Gly
        275                 280                 285 att act ggt ggt ggc tat tgg gct aac ggt cgt cgt cct ctg gcg ctg       912
Ile Thr Gly Gly Gly Tyr Trp Ala Asn Gly Arg Arg Pro Leu Ala Leu
    290                 295                 300 gtg cgt act cac agt aag aaa gca ctg atg cgc tac gaa gac gtt tac       960
Val Arg Thr His Ser Lys Lys Ala Leu Met Arg Tyr Glu Asp Val Tyr
305                 310                 315                 320 atg cct gag gtg tac aaa gcg att aac att gcg caa aac acc gca tgg      1008
Met Pro Glu Val Tyr Lys Ala Ile Asn Ile Ala Gln Asn Thr Ala Trp
                325                 330                 335
```

```
aaa atc aac aag aaa gtc cta gcg gtc gcc aac gta atc acc aag tgg      1056
Lys Ile Asn Lys Lys Val Leu Ala Val Ala Asn Val Ile Thr Lys Trp
            340                 345                 350 aag cat tgt ccg gtc gag gac atc cct gcg att gag cgt gaa gaa ctc      1104
Lys His Cys Pro Val Glu Asp Ile Pro Ala Ile Glu Arg Glu Glu Leu
            355                 360                 365 ccg atg aaa ccg gaa gac atc gac atg aat cct gag gct ctc acc gcg      1152
Pro Met Lys Pro Glu Asp Ile Asp Met Asn Pro Glu Ala Leu Thr Ala
            370                 375                 380 tgg aaa cgt gct gcc gct gct gtg tac cgc aag gac aag gct cgc aag      1200
Trp Lys Arg Ala Ala Ala Ala Val Tyr Arg Lys Asp Lys Ala Arg Lys
385                 390                 395                 400 tct cgc cgt atc agc ctt gag ttc atg ctt gag caa gcc aat aag ttt      1248
Ser Arg Arg Ile Ser Leu Glu Phe Met Leu Glu Gln Ala Asn Lys Phe
            405                 410                 415 gct aac cat aag gcc atc tgg ttc cct tac aac atg gac tgg cgc ggt      1296
Ala Asn His Lys Ala Ile Trp Phe Pro Tyr Asn Met Asp Trp Arg Gly
            420                 425                 430 cgt gtt tac gct gtg tca atg ttc aac ccg caa ggt aac gat atg acc      1344
Arg Val Tyr Ala Val Ser Met Phe Asn Pro Gln Gly Asn Asp Met Thr
            435                 440                 445 aaa gga ctg ctt acg ctg gcg aaa ggt aaa cca atc ggt aag gaa ggt      1392
Lys Gly Leu Leu Thr Leu Ala Lys Gly Lys Pro Ile Gly Lys Glu Gly
            450                 455                 460 tac tac tgg ctg aaa atc cac ggt gca aac tgt gcg ggt gtc gat aag      1440
Tyr Tyr Trp Leu Lys Ile His Gly Ala Asn Cys Ala Gly Val Asp Lys
465                 470                 475                 480 gtt ccg ttc cct gag cgc atc aag ttc att gag gaa aac cac gag aac      1488
Val Pro Phe Pro Glu Arg Ile Lys Phe Ile Glu Glu Asn His Glu Asn
            485                 490                 495 atc atg gct tgc gct aag tct cca ctg gag aac act tgg tgg gct gag      1536
Ile Met Ala Cys Ala Lys Ser Pro Leu Glu Asn Thr Trp Trp Ala Glu
            500                 505                 510 caa gat tct ccg ttc tgc ttc ctt gcg ttc tgc ttt gag tac gct ggg      1584
Gln Asp Ser Pro Phe Cys Phe Leu Ala Phe Cys Phe Glu Tyr Ala Gly
            515                 520                 525 gta cag cac cac ggc ctg agc tat aac tgc tcc ctt ccg ctg gcg ttt      1632
Val Gln His His Gly Leu Ser Tyr Asn Cys Ser Leu Pro Leu Ala Phe
530                 535                 540 gac ggg tct tgc tct ggc atc cag cac ttc tcc gcg atg ctc cga gat      1680
Asp Gly Ser Cys Ser Gly Ile Gln His Phe Ser Ala Met Leu Arg Asp
545                 550                 555                 560 gag gta ggt ggt cgc gcg gtt aac ttg ctt cct agt gaa acc gtt cag      1728
Glu Val Gly Gly Arg Ala Val Asn Leu Leu Pro Ser Glu Thr Val Gln
            565                 570                 575 gac atc tac ggg att gtt gct aag aaa gtc aac gag att cta caa gca      1776
Asp Ile Tyr Gly Ile Val Ala Lys Lys Val Asn Glu Ile Leu Gln Ala
            580                 585                 590 gac gca atc aat ggg acc gat aac gaa gta gtt acc gtg acc gat gag      1824
Asp Ala Ile Asn Gly Thr Asp Asn Glu Val Val Thr Val Thr Asp Glu
            595                 600                 605 aac act ggt gaa atc tct gag aaa gtc aag ctt ggc act aag gca ctg      1872
Asn Thr Gly Glu Ile Ser Glu Lys Val Lys Leu Gly Thr Lys Ala Leu
            610                 615                 620 gct ggt caa tgg ctg gct tac ggt gtt act cgc agt gtg act aag cgt      1920
Ala Gly Gln Trp Leu Ala Tyr Gly Val Thr Arg Ser Val Thr Lys Arg
625                 630                 635                 640 tca gtc atg acg ctg gct tac ggg tcc aaa gag ttc ggc ttc cgt caa      1968
Ser Val Met Thr Leu Ala Tyr Gly Ser Lys Glu Phe Gly Phe Arg Gln
            645                 650                 655
```

```
caa gtg ctg gaa gat acc att cag cca gct att gat tcc ggc aag ggt    2016
Gln Val Leu Glu Asp Thr Ile Gln Pro Ala Ile Asp Ser Gly Lys Gly
        660                 665                 670 ctg atg ttc act cag ccg aat cag gct gct gga tac atg gct aag ctg    2064
Leu Met Phe Thr Gln Pro Asn Gln Ala Ala Gly Tyr Met Ala Lys Leu
    675                 680                 685 att tgg gaa tct gtg agc gtg acg gtg gta gct gcg gtt gaa gca atg    2112
Ile Trp Glu Ser Val Ser Val Thr Val Val Ala Ala Val Glu Ala Met
690                 695                 700 aac tgg ctt aag tct gct gct aag ctt ctg gct gct gag gtc aaa gat    2160
Asn Trp Leu Lys Ser Ala Ala Lys Leu Leu Ala Ala Glu Val Lys Asp
705                 710                 715                 720 aag aag act gga gag att ctt cgc aag cgt tgc gct gtg cat tgg gta    2208
Lys Lys Thr Gly Glu Ile Leu Arg Lys Arg Cys Ala Val His Trp Val
            725                 730                 735 act cct gat ggt ttc cct gtg tgg cag gaa tac aag aag cct att cag    2256
Thr Pro Asp Gly Phe Pro Val Trp Gln Glu Tyr Lys Lys Pro Ile Gln
        740                 745                 750 acg cgc ttg aac ctg atg ttc ctc ggt cag ttc cgc tta cag cct acc    2304
Thr Arg Leu Asn Leu Met Phe Leu Gly Gln Phe Arg Leu Gln Pro Thr
    755                 760                 765 att aac acc aac aaa gat agc gag att gat gca cac aaa cag gag tct    2352
Ile Asn Thr Asn Lys Asp Ser Glu Ile Asp Ala His Lys Gln Glu Ser
770                 775                 780 ggt atc gct cct aac ttt gta cac agc caa gac ggt agc cac ctt cgt    2400
Gly Ile Ala Pro Asn Phe Val His Ser Gln Asp Gly Ser His Leu Arg
785                 790                 795                 800 aag act gta gtg tgg gca cac gag aag tac gga atc gaa tct ttt gca    2448
Lys Thr Val Val Trp Ala His Glu Lys Tyr Gly Ile Glu Ser Phe Ala
            805                 810                 815 ctg att cac gac tcc ttc ggt acc att ccg gct gac gct gcg aac ctg    2496
Leu Ile His Asp Ser Phe Gly Thr Ile Pro Ala Asp Ala Ala Asn Leu
        820                 825                 830 ttc aaa gca gtg cgc gaa act atg gtt gac aca tat gag tct tgt gat    2544
Phe Lys Ala Val Arg Glu Thr Met Val Asp Thr Tyr Glu Ser Cys Asp
    835                 840                 845 gta ctg gct gat ttc tac gac cag ttc gct gac cag ttg cac gag tct    2592
Val Leu Ala Asp Phe Tyr Asp Gln Phe Ala Asp Gln Leu His Glu Ser
850                 855                 860 caa ttg gac aaa atg cca gca ctt ccg gct aaa ggt aac ttg aac ctc    2640
Gln Leu Asp Lys Met Pro Ala Leu Pro Ala Lys Gly Asn Leu Asn Leu
865                 870                 875                 880 cgt gac atc tta gag tcg gac ttc gcg ttc gcg taa                    2676
Arg Asp Ile Leu Glu Ser Asp Phe Ala Phe Ala
            885                 890

<210> SEQ ID NO 14
<211> LENGTH: 891
<212> TYPE: PRT
<213> ORGANISM: Artificial Sequence
<220> FEATURE:
<223> OTHER INFORMATION: Synthetic T7 RNA polymerase protein

<400> SEQUENCE: 14

Met Gly His His His His His His Met Asn Thr Ile Asn Ile Ala Lys
1               5                   10                  15

Asn Asp Phe Ser Asp Ile Glu Leu Ala Ala Ile Pro Phe Asn Thr Leu
            20                  25                  30

Ala Asp His Tyr Gly Glu Arg Leu Ala Arg Glu Gln Leu Ala Leu Glu
        35                  40                  45

His Glu Ser Tyr Glu Met Gly Glu Ala Arg Phe Arg Lys Met Phe Glu
```

```
                50                  55                  60
Arg Gln Leu Lys Ala Gly Glu Val Ala Asp Asn Ala Ala Lys Pro
 65                  70                  75                  80

Leu Ile Thr Thr Leu Leu Pro Lys Met Ile Ala Arg Ile Asn Asp Trp
                 85                  90                  95

Phe Glu Glu Val Lys Ala Lys Arg Gly Lys Arg Pro Thr Ala Phe Gln
                100                 105                 110

Phe Leu Gln Glu Ile Lys Pro Glu Ala Val Ala Tyr Ile Thr Ile Lys
                115                 120                 125

Thr Thr Leu Ala Cys Leu Thr Ser Ala Asp Asn Thr Thr Val Gln Ala
                130                 135                 140

Val Ala Ser Ala Ile Gly Arg Ala Ile Glu Asp Glu Ala Arg Phe Gly
145                 150                 155                 160

Arg Ile Arg Asp Leu Glu Ala Lys His Phe Lys Lys Asn Val Glu Glu
                165                 170                 175

Gln Leu Asn Lys Arg Val Gly His Val Tyr Lys Lys Ala Phe Met Gln
                180                 185                 190

Val Val Glu Ala Asp Met Leu Ser Lys Gly Leu Leu Gly Gly Glu Ala
                195                 200                 205

Trp Ser Ser Trp His Lys Glu Asp Ser Ile His Val Gly Val Arg Cys
210                 215                 220

Ile Glu Met Leu Ile Glu Ser Thr Gly Met Val Ser Leu His Arg Gln
225                 230                 235                 240

Asn Ala Gly Val Val Gly Gln Asp Ser Glu Thr Ile Glu Leu Ala Pro
                245                 250                 255

Glu Tyr Ala Glu Ala Ile Ala Thr Arg Ala Gly Ala Leu Ala Gly Ile
                260                 265                 270

Ser Pro Met Phe Gln Pro Cys Val Val Pro Lys Pro Trp Thr Gly
                275                 280                 285

Ile Thr Gly Gly Gly Tyr Trp Ala Asn Gly Arg Arg Pro Leu Ala Leu
                290                 295                 300

Val Arg Thr His Ser Lys Lys Ala Leu Met Arg Tyr Glu Asp Val Tyr
305                 310                 315                 320

Met Pro Glu Val Tyr Lys Ala Ile Asn Ile Ala Gln Asn Thr Ala Trp
                325                 330                 335

Lys Ile Asn Lys Lys Val Leu Ala Val Ala Asn Val Ile Thr Lys Trp
                340                 345                 350

Lys His Cys Pro Val Glu Asp Ile Pro Ala Ile Glu Arg Glu Glu Leu
                355                 360                 365

Pro Met Lys Pro Glu Asp Ile Asp Met Asn Pro Glu Ala Leu Thr Ala
                370                 375                 380

Trp Lys Arg Ala Ala Ala Val Tyr Arg Lys Asp Lys Ala Arg Lys
385                 390                 395                 400

Ser Arg Arg Ile Ser Leu Glu Phe Met Leu Glu Gln Ala Asn Lys Phe
                405                 410                 415

Ala Asn His Lys Ala Ile Trp Phe Pro Tyr Asn Met Asp Trp Arg Gly
                420                 425                 430

Arg Val Tyr Ala Val Ser Met Phe Asn Pro Gln Gly Asn Asp Met Thr
                435                 440                 445

Lys Gly Leu Leu Thr Leu Ala Lys Gly Lys Pro Ile Gly Lys Glu Gly
                450                 455                 460

Tyr Tyr Trp Leu Lys Ile His Gly Ala Asn Cys Ala Gly Val Asp Lys
465                 470                 475                 480
```

-continued

Val Pro Phe Pro Glu Arg Ile Lys Phe Ile Glu Glu Asn His Glu Asn
            485                 490                 495

Ile Met Ala Cys Ala Lys Ser Pro Leu Glu Asn Thr Trp Trp Ala Glu
                500                 505                 510

Gln Asp Ser Pro Phe Cys Phe Leu Ala Phe Cys Phe Glu Tyr Ala Gly
            515                 520                 525

Val Gln His His Gly Leu Ser Tyr Asn Cys Ser Leu Pro Leu Ala Phe
        530                 535                 540

Asp Gly Ser Cys Ser Gly Ile Gln His Phe Ser Ala Met Leu Arg Asp
545                 550                 555                 560

Glu Val Gly Gly Arg Ala Val Asn Leu Leu Pro Ser Glu Thr Val Gln
                565                 570                 575

Asp Ile Tyr Gly Ile Val Ala Lys Lys Val Asn Glu Ile Leu Gln Ala
            580                 585                 590

Asp Ala Ile Asn Gly Thr Asp Asn Glu Val Val Thr Val Thr Asp Glu
        595                 600                 605

Asn Thr Gly Glu Ile Ser Glu Lys Val Lys Leu Gly Thr Lys Ala Leu
    610                 615                 620

Ala Gly Gln Trp Leu Ala Tyr Gly Val Thr Arg Ser Val Thr Lys Arg
625                 630                 635                 640

Ser Val Met Thr Leu Ala Tyr Gly Ser Lys Glu Phe Gly Phe Arg Gln
                645                 650                 655

Gln Val Leu Glu Asp Thr Ile Gln Pro Ala Ile Asp Ser Gly Lys Gly
            660                 665                 670

Leu Met Phe Thr Gln Pro Asn Gln Ala Ala Gly Tyr Met Ala Lys Leu
        675                 680                 685

Ile Trp Glu Ser Val Ser Val Thr Val Ala Val Glu Ala Met
690                 695                 700

Asn Trp Leu Lys Ser Ala Ala Lys Leu Leu Ala Ala Glu Val Lys Asp
705                 710                 715                 720

Lys Lys Thr Gly Glu Ile Leu Arg Lys Arg Cys Ala Val His Trp Val
                725                 730                 735

Thr Pro Asp Gly Phe Pro Val Trp Gln Glu Tyr Lys Lys Pro Ile Gln
            740                 745                 750

Thr Arg Leu Asn Leu Met Phe Leu Gly Gln Phe Arg Leu Gln Pro Thr
        755                 760                 765

Ile Asn Thr Asn Lys Asp Ser Glu Ile Asp Ala His Lys Gln Glu Ser
    770                 775                 780

Gly Ile Ala Pro Asn Phe Val His Ser Gln Asp Gly Ser His Leu Arg
785                 790                 795                 800

Lys Thr Val Val Trp Ala His Glu Lys Tyr Gly Ile Glu Ser Phe Ala
                805                 810                 815

Leu Ile His Asp Ser Phe Gly Thr Ile Pro Ala Asp Ala Ala Asn Leu
            820                 825                 830

Phe Lys Ala Val Arg Glu Thr Met Val Asp Thr Tyr Glu Ser Cys Asp
        835                 840                 845

Val Leu Ala Asp Phe Tyr Asp Gln Phe Ala Asp Gln Leu His Glu Ser
    850                 855                 860

Gln Leu Asp Lys Met Pro Ala Leu Pro Ala Lys Gly Asn Leu Asn Leu
865                 870                 875                 880

Arg Asp Ile Leu Glu Ser Asp Phe Ala Phe Ala
                885                 890

<210> SEQ ID NO 15

```
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 15
gagcggataa caatttcaca cagg                                              24

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 16
gcattggtaa ctgtcagacc aag                                               23

<210> SEQ ID NO 17
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 17
ggtatggctg tgcaggtcgt aaatcactg                                         29

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 18
cgactggttt gaggaagtga aagctaagcg                                        30

<210> SEQ ID NO 19
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 19
aggtcaagac tctgagacta tcgaactcgc                                        30

<210> SEQ ID NO 20
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 20
acaaggctcg caagtctcgc cgtatcagcc                                        30

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 21
```
tcttgctctg gcatccagca cttctccgcg                                    30

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 22
tggtagctgc ggttgaagca atgaactggc                                    30

<210> SEQ ID NO 23
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 23
tgtactggct gatttctacg accagttcgc                                    30

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 24
tatttgatgc ctggcagttc cctactctc                                     29

<210> SEQ ID NO 25
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 25
aagattcgat tccgtacttc tcgtgtgccc                                    30

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 26
gtatcttcca gcacttgttg acggaagccg                                    30

<210> SEQ ID NO 27
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 27
accaagtgtt ctccagtgga gacttagcg                                     29

<210> SEQ ID NO 28
<211> LENGTH: 30
<212> TYPE: DNA
<213> ORGANISM: Artificial Sequence
<220> FEATURE:

-continued

<223> OTHER INFORMATION: Synthetic oligonucleotide primer

<400> SEQUENCE: 28
tgtcctcgac cggacaatgc ttccacttgg                                    30

<210> SEQ ID NO 29
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 29
ccgagtagac ccttagagag catgtcagcc                                    30

<210> SEQ ID NO 30
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 30
cccatctcgt aagactcat gctcaagggcc                                    30

<210> SEQ ID NO 31
<211> LENGTH: 2652
<212> TYPE: DNA
<213> ORGANISM: Artificial Sequence
<220> FEATURE:
<223> OTHER INFORMATION: Synthetic T7 RNA polymerase gene

<400> SEQUENCE: 31

```
atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160
```

```
cac ttc aag aaa aac gtt gag gaa caa ctc aac aag cgc gta ggg cac        528
His Phe Lys Lys Asn Val Glu Glu Gln Leu Asn Lys Arg Val Gly His
            165                 170                 175 gtc tac gag aaa gca ttt atg caa gtt gtc gag gct gac atg ctc tct        576
Val Tyr Glu Lys Ala Phe Met Gln Val Val Glu Ala Asp Met Leu Ser
            180                 185                 190 aag ggt cta ctc ggt ggc gag gcg tgg tct tcg tgg cat aag gaa gac        624
Lys Gly Leu Leu Gly Gly Glu Ala Trp Ser Ser Trp His Lys Glu Asp
            195                 200                 205 tct att cat gta gga gta cgc tgc atc gag atg ctc att gag tca acc        672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac        720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc        768
Ser Glu Thr Ile Glu Leu Ala Pro Glu Tyr Ala Glu Ala Ile Ala Thr
            245                 250                 255 cgt gca ggt gcg ctg gct ggc atc tct ccg atg ttc caa cct tgc gta        816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct        864
Val Pro Pro Lys Pro Trp Thr Gly Ile Thr Gly Gly Gly Tyr Trp Ala
            275                 280                 285 aac ggt cgt cgt cct ctg gcg ctg gtg cgt act cac agt aag aaa gca        912
Asn Gly Arg Arg Pro Leu Ala Leu Val Arg Thr His Ser Lys Lys Ala
            290                 295                 300 ctg atg cgc tac gaa gac gtt tac atg cct gag gtg tac aaa gcg att        960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg        1008
Asn Ile Ala Gln Asn Thr Ala Trp Lys Ile Asn Lys Lys Val Leu Ala
            325                 330                 335 gtc gcc aac gta atc acc aag tgg aag cat tgt ccg gtc gag gac atc        1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac        1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg        1152
Met Asn Pro Glu Ala Leu Thr Ala Trp Lys Arg Ala Ala Ala Ala Val
            370                 375                 380 tac cgc aag gac aag gct cgc aag tct cgc cgt atc agc ctt gag ttc        1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc        1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc        1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa        1344
Asn Pro Gln Gly Asn Asp Met Thr Lys Gly Leu Leu Thr Leu Ala Lys
            435                 440                 445 ggt aaa cca atc ggt aag gaa ggt tac tac tgg ctg aaa atc cac ggt        1392
Gly Lys Pro Ile Gly Lys Glu Gly Tyr Tyr Trp Leu Lys Ile His Gly
            450                 455                 460 gca aac tgt gcg ggt gtc gat aag gtt ccg ttc cct gag cgc atc aag        1440
Ala Asn Cys Ala Gly Val Asp Lys Val Pro Phe Pro Glu Arg Ile Lys
465                 470                 475                 480
```

| | | | | | | | | | | | | | | | | |
|---|---|---|---|---|---|---|---|---|---|---|---|---|---|---|---|---|
| ttc | att | gag | gaa | aac | cac | gag | aac | atc | atg | gct | tgc | gct | aag | tct | cca | 1488 |
| Phe | Ile | Glu | Glu | Asn | His | Glu | Asn | Ile | Met | Ala | Cys | Ala | Lys | Ser | Pro | |
| | | | | | 485 | | | | 490 | | | | 495 | | | |
| ctg | gag | aac | act | tgg | tgg | gct | gag | caa | gat | tct | ccg | ttc | tgc | ttc | ctt | 1536 |
| Leu | Glu | Asn | Thr | Trp | Trp | Ala | Glu | Gln | Asp | Ser | Pro | Phe | Cys | Phe | Leu | |
| | | | 500 | | | | | 505 | | | | | 510 | | | |
| gcg | ttc | tgc | ttt | gag | tac | gct | ggg | gta | cag | cac | cac | ggc | ctg | agc | tat | 1584 |
| Ala | Phe | Cys | Phe | Glu | Tyr | Ala | Gly | Val | Gln | His | His | Gly | Leu | Ser | Tyr | |
| | | 515 | | | | | 520 | | | | | 525 | | | | |
| aac | tgc | tcc | ctt | ccg | ctg | gcg | ttt | gac | ggg | tct | tgc | tct | ggc | atc | cag | 1632 |
| Asn | Cys | Ser | Leu | Pro | Leu | Ala | Phe | Asp | Gly | Ser | Cys | Ser | Gly | Ile | Gln | |
| | 530 | | | | | 535 | | | | | 540 | | | | | |
| cac | ttc | tcc | gcg | atg | ctc | cga | gat | gag | gta | ggt | ggt | cgc | gcg | gtt | aac | 1680 |
| His | Phe | Ser | Ala | Met | Leu | Arg | Asp | Glu | Val | Gly | Gly | Arg | Ala | Val | Asn | |
| 545 | | | | | 550 | | | | | 555 | | | | | 560 | |
| ttg | ctt | cct | agt | gaa | acc | gtt | cag | gac | atc | tac | ggg | att | gtt | gct | aag | 1728 |
| Leu | Leu | Pro | Ser | Glu | Thr | Val | Gln | Asp | Ile | Tyr | Gly | Ile | Val | Ala | Lys | |
| | | | | 565 | | | | | 570 | | | | | 575 | | |
| aaa | gtc | aac | gag | att | cta | caa | gca | gac | gca | atc | aat | ggg | acc | gat | aac | 1776 |
| Lys | Val | Asn | Glu | Ile | Leu | Gln | Ala | Asp | Ala | Ile | Asn | Gly | Thr | Asp | Asn | |
| | | | 580 | | | | | 585 | | | | | 590 | | | |
| gaa | gta | gtt | acc | gtg | acc | gat | gag | aac | act | ggt | gaa | atc | tct | gag | aaa | 1824 |
| Glu | Val | Val | Thr | Val | Thr | Asp | Glu | Asn | Thr | Gly | Glu | Ile | Ser | Glu | Lys | |
| | | | 595 | | | | | 600 | | | | | 605 | | | |
| gtc | aag | ctt | ggc | act | aag | gca | ctg | gct | ggt | caa | tgg | ctg | gct | tac | ggt | 1872 |
| Val | Lys | Leu | Gly | Thr | Lys | Ala | Leu | Ala | Gly | Gln | Trp | Leu | Ala | Tyr | Gly | |
| | | 610 | | | | | 615 | | | | | 620 | | | | |
| gtt | act | cgc | agt | gtg | act | aag | cgt | tca | gtc | atg | acg | ctg | gct | tac | ggg | 1920 |
| Val | Thr | Arg | Ser | Val | Thr | Lys | Arg | Ser | Val | Met | Thr | Leu | Ala | Tyr | Gly | |
| 625 | | | | | 630 | | | | | 635 | | | | | 640 | |
| tcc | aaa | gag | ttc | ggc | ttc | cgt | caa | caa | gtg | ctg | gaa | gat | acc | att | cag | 1968 |
| Ser | Lys | Glu | Phe | Gly | Phe | Arg | Gln | Gln | Val | Leu | Glu | Asp | Thr | Ile | Gln | |
| | | | | 645 | | | | | 650 | | | | | 655 | | |
| cca | gct | att | gat | tcc | ggc | aag | ggt | ctg | atg | ttc | act | cag | ccg | aat | cag | 2016 |
| Pro | Ala | Ile | Asp | Ser | Gly | Lys | Gly | Leu | Met | Phe | Thr | Gln | Pro | Asn | Gln | |
| | | | 660 | | | | | 665 | | | | | 670 | | | |
| gct | gct | gga | tac | atg | gct | aag | ctg | att | tgg | gaa | tct | gtg | agc | gtg | acg | 2064 |
| Ala | Ala | Gly | Tyr | Met | Ala | Lys | Leu | Ile | Trp | Glu | Ser | Val | Ser | Val | Thr | |
| | | | | 675 | | | | | 680 | | | | | 685 | | |
| gtg | gta | gct | gcg | gtt | gaa | gca | atg | aac | tgg | ctt | aag | tct | gct | gct | aag | 2112 |
| Val | Val | Ala | Ala | Val | Glu | Ala | Met | Asn | Trp | Leu | Lys | Ser | Ala | Ala | Lys | |
| | | | 690 | | | | | 695 | | | | | 700 | | | |
| ctt | ctg | gct | gct | gag | gtc | aaa | gat | aag | aag | act | gga | gag | att | ctt | cgc | 2160 |
| Leu | Leu | Ala | Ala | Glu | Val | Lys | Asp | Lys | Lys | Thr | Gly | Glu | Ile | Leu | Arg | |
| 705 | | | | | 710 | | | | | 715 | | | | | 720 | |
| aag | cgt | tgc | gct | gtg | cat | tgg | gta | act | cct | gat | ggt | ttc | cct | gtg | tgg | 2208 |
| Lys | Arg | Cys | Ala | Val | His | Trp | Val | Thr | Pro | Asp | Gly | Phe | Pro | Val | Trp | |
| | | | | 725 | | | | | 730 | | | | | 735 | | |
| cag | gaa | tac | aag | aag | cct | att | cag | acg | cgc | ttg | aac | ctg | atg | ttc | ctc | 2256 |
| Gln | Glu | Tyr | Lys | Lys | Pro | Ile | Gln | Thr | Arg | Leu | Asn | Leu | Met | Phe | Leu | |
| | | | 740 | | | | | 745 | | | | | 750 | | | |
| ggt | cag | ttc | cgc | tta | cag | cct | acc | att | aac | acc | aac | aaa | gat | agc | gag | 2304 |
| Gly | Gln | Phe | Arg | Leu | Gln | Pro | Thr | Ile | Asn | Thr | Asn | Lys | Asp | Ser | Glu | |
| | | 755 | | | | | 760 | | | | | 765 | | | | |
| att | gat | gca | cac | aaa | cag | gag | tct | ggt | atc | gct | cct | aac | ttt | gta | cac | 2352 |
| Ile | Asp | Ala | His | Lys | Gln | Glu | Ser | Gly | Ile | Ala | Pro | Asn | Phe | Val | His | |
| | 770 | | | | | 775 | | | | | 780 | | | | | |
| agc | caa | gac | ggt | agc | cac | ctt | cgt | aag | act | gta | gtg | tgg | gca | cac | gag | 2400 |
| Ser | Gln | Asp | Gly | Ser | His | Leu | Arg | Lys | Thr | Val | Val | Trp | Ala | His | Glu | |
| 785 | | | | | 790 | | | | | 795 | | | | | 800 | |

```
aag tac gga atc gaa tct ttt gca ctg att cac gac tcc ttc ggt acc    2448
Lys Tyr Gly Ile Glu Ser Phe Ala Leu Ile His Asp Ser Phe Gly Thr
            805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
        820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
    835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                     2652
Ala Phe Ala
```

<210> SEQ ID NO 32
<211> LENGTH: 883
<212> TYPE: PRT
<213> ORGANISM: Artificial Sequence
<220> FEATURE:
<223> OTHER INFORMATION: Synthetic T7 RNA polymerase protein

<400> SEQUENCE: 32

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Glu Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255
```

```
Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
```

```
                675                 680                 685
Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 33
<211> LENGTH: 2652
<212> TYPE: DNA
<213> ORGANISM: Artificial Sequence
<220> FEATURE:
<223> OTHER INFORMATION: Synthetic T7 RNA polymerase gene

<400> SEQUENCE: 33 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
```

```
                    115                 120                 125
gct gac aat aca acc gtt cag gct gta gca agc gca atc ggt cgg gcc      432
Ala Asp Asn Thr Thr Val Gln Ala Val Ala Ser Ala Ile Gly Arg Ala
        130                 135                 140 att gag gac gag gct cgc ttc ggt cgt atc cgt gac ctt gaa gct aag      480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac      528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct      576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac      624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc      672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac      720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc      768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta      816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct      864
Val Pro Pro Lys Pro Trp Thr Gly Ile Thr Gly Gly Gly Tyr Trp Ala
        275                 280                 285 aac ggt cgt cgt cct ctg gcg ctg gtg cgt act cac agt aag aaa gca      912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc     1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
```

```
                435                 440                 445
ggt aaa cca atc ggt aag gaa ggt tac tac tgg ctg aaa atc cac ggt        1392
Gly Lys Pro Ile Gly Lys Glu Gly Tyr Tyr Trp Leu Lys Ile His Gly
        450                 455                 460 gca aac tgt gcg ggt gtc gat aag gtt ccg ttc cct gag cgc atc aag        1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca        1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt        1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat        1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag        1632
Asn Cys Ser Leu Pro Leu Ala Phe Asp Gly Ser Cys Ser Gly Ile Gln
530                 535                 540 cac ttc tcc gcg atg ctc cga gat gag gta ggt ggt cgc gcg gtt aac        1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag        1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac        1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa        1824
Glu Val Val Thr Val Thr Asp Glu Asn Thr Gly Glu Ile Ser Glu Lys
        595                 600                 605 gtc aag ctt ggc act aag gca ctg gct ggt caa tgg ctg gct tac ggt        1872
Val Lys Leu Gly Thr Lys Ala Leu Ala Gly Gln Trp Leu Ala Tyr Gly
610                 615                 620 gtt act cgc agt gtg act aag cgt tca gtc atg acg ctg gct tac ggg        1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag        1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag        2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg        2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag        2112
Val Val Ala Ala Val Glu Ala Met Asn Trp Leu Lys Ser Ala Ala Lys
690                 695                 700 ctt ctg gct gct gag gtc aaa gat aag aag act gga gag att ctt cgc        2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg        2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc        2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag        2304
Gly Gln Phe Arg Leu Gln Pro Thr Ile Asn Thr Asn Lys Asp Ser Glu
```

```
                      755                 760                 765
att gat gca cac aaa cag gag tct ggt atc gct cct aac ttt gta cac      2352
Ile Asp Ala His Lys Gln Glu Ser Gly Ile Ala Pro Asn Phe Val His
    770                 775                 780 agc cta gac ggt agc cac ctt cgt aag act gta gtg tgg gca cac gag      2400
Ser Leu Asp Gly Ser His Leu Arg Lys Thr Val Val Trp Ala His Glu
785                 790                 795                 800 aag tac gga atc gaa tct ttt gca ctg att cac gac tcc ttc ggt acc      2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg      2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag      2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt      2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc      2640
Pro Ala Lys Gly Asn Leu Asn Leu Arg Asp Ile Leu Glu Ser Asp Phe
865                 870                 875                 880 gcg ttc gcg taa                                                       2652
Ala Phe Ala <210> SEQ ID NO 34
<211> LENGTH: 883
<212> TYPE: PRT
<213> ORGANISM: Artificial Sequence
<220> FEATURE:
<223> OTHER INFORMATION: Synthetic T7 RNA polymerase protein

<400> SEQUENCE: 34

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
```

```
                195                 200                 205
    Ser Ile His Val Gly Val Arg Cys Ile Glu Met Leu Ile Glu Ser Thr
        210                 215                 220
    Gly Met Val Ser Leu His Arg Gln Asn Ala Gly Val Val Gly Gln Asp
    225                 230                 235                 240
    Ser Glu Thr Ile Glu Leu Ala Pro Glu Tyr Ala Glu Ala Ile Ala Thr
                    245                 250                 255
    Arg Ala Gly Ala Leu Ala Gly Ile Ser Pro Met Phe Gln Pro Cys Val
                260                 265                 270
    Val Pro Pro Lys Pro Trp Thr Gly Ile Thr Gly Gly Tyr Trp Ala
            275                 280                 285
    Asn Gly Arg Arg Pro Leu Ala Leu Val Arg Thr His Ser Lys Lys Ala
        290                 295                 300
    Leu Met Arg Tyr Glu Asp Val Tyr Met Pro Glu Val Tyr Lys Ala Ile
    305                 310                 315                 320
    Asn Ile Ala Gln Asn Thr Ala Trp Lys Ile Asn Lys Lys Val Leu Ala
                    325                 330                 335
    Val Ala Asn Val Ile Thr Lys Trp Lys His Cys Pro Val Glu Asp Ile
                340                 345                 350
    Pro Ala Ile Glu Arg Glu Glu Leu Pro Met Lys Pro Glu Asp Ile Asp
            355                 360                 365
    Met Asn Pro Glu Ala Leu Thr Ala Trp Lys Arg Ala Ala Ala Val
        370                 375                 380
    Tyr Arg Lys Asp Lys Ala Arg Lys Ser Arg Ile Ser Leu Glu Phe
    385                 390                 395                 400
    Met Leu Glu Gln Ala Asn Lys Phe Ala Asn His Lys Ala Ile Trp Phe
                    405                 410                 415
    Pro Tyr Asn Met Asp Trp Arg Gly Arg Val Tyr Ala Val Ser Met Phe
                420                 425                 430
    Asn Pro Gln Gly Asn Asp Met Thr Lys Gly Leu Leu Thr Leu Ala Lys
            435                 440                 445
    Gly Lys Pro Ile Gly Lys Glu Gly Tyr Tyr Trp Leu Lys Ile His Gly
        450                 455                 460
    Ala Asn Cys Ala Gly Val Asp Lys Val Pro Phe Pro Glu Arg Ile Lys
    465                 470                 475                 480
    Phe Ile Glu Glu Asn His Glu Asn Ile Met Ala Cys Ala Lys Ser Pro
                    485                 490                 495
    Leu Glu Asn Thr Trp Trp Ala Glu Gln Asp Ser Pro Phe Cys Phe Leu
                500                 505                 510
    Ala Phe Cys Phe Glu Tyr Ala Gly Val Gln His His Gly Leu Ser Tyr
            515                 520                 525
    Asn Cys Ser Leu Pro Leu Ala Phe Asp Gly Ser Cys Ser Gly Ile Gln
        530                 535                 540
    His Phe Ser Ala Met Leu Arg Asp Glu Val Gly Gly Arg Ala Val Asn
    545                 550                 555                 560
    Leu Leu Pro Ser Glu Thr Val Gln Asp Ile Tyr Gly Ile Val Ala Lys
                    565                 570                 575
    Lys Val Asn Glu Ile Leu Gln Ala Asp Ala Ile Asn Gly Thr Asp Asn
                580                 585                 590
    Glu Val Val Thr Val Thr Asp Glu Asn Thr Gly Glu Ile Ser Glu Lys
            595                 600                 605
    Val Lys Leu Gly Thr Lys Ala Leu Ala Gly Gln Trp Leu Ala Tyr Gly
        610                 615                 620
```

-continued

```
Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
770                 775                 780

Ser Leu Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 35
<211> LENGTH: 2652
<212> TYPE: DNA
<213> ORGANISM: Artificial Sequence
<220> FEATURE:
<223> OTHER INFORMATION: Synthetic T7 RNA polymerase gene

<400> SEQUENCE: 35 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
                20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
            35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
        50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80
```

```
atg att gca cgc atc aac gac tgg ttt gag gaa gta aaa gct aag cgc        288
Met Ile Ala Arg Ile Asn Asp Trp Phe Glu Glu Val Lys Ala Lys Arg
            85                  90                  95 ggc aag cgc ccg aca gcc ttc cag ttc ctg caa gaa atc aag ccg gaa        336
Gly Lys Arg Pro Thr Ala Phe Gln Phe Leu Gln Glu Ile Lys Pro Glu
        100                 105                 110 gcc gta gcg tac atc acc att aag acc act ctg gct tgc cta acc agt        384
Ala Val Ala Tyr Ile Thr Ile Lys Thr Thr Leu Ala Cys Leu Thr Ser
            115                 120                 125 gct gac aat aca acc gtt cag gct gta gca agc gca atc ggt cgg gcc        432
Ala Asp Asn Thr Thr Val Gln Ala Val Ala Ser Ala Ile Gly Arg Ala
130                 135                 140 att gag gac gag gct cgc ttc ggt cgt atc cgt gac ctt gaa gct aag        480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac        528
His Phe Lys Lys Asn Val Glu Glu Gln Leu Asn Lys Arg Val Gly His
                165                 170                 175 gtc tac gag aaa gca ttt atg caa gtt gtc gag gct gac atg ctc tct        576
Val Tyr Glu Lys Ala Phe Met Gln Val Val Glu Ala Asp Met Leu Ser
            180                 185                 190 aag ggt cta ctc ggt ggc gag gcg tgg tct tcg tgg cat aag gaa gac        624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc        672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac        720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc        768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta        816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct        864
Val Pro Pro Lys Pro Trp Thr Gly Ile Thr Gly Gly Gly Tyr Trp Ala
        275                 280                 285 aac ggt cgt cgt cct ctg gcg ctg gtg cgt act cac agt aag aaa gca        912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att        960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg       1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc       1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac       1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg       1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc       1200
Tyr Arg Lys Asp Lys Ala Arg Lys Ser Arg Arg Ile Ser Leu Glu Phe
385                 390                 395                 400
```

```
                                                               -continued atg ctt gag caa gcc aat aag ttt gct aac cat aag gcc atc tgg ttc      1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc      1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa      1344
Asn Pro Gln Gly Asn Asp Met Thr Lys Gly Leu Leu Thr Leu Ala Lys
    435                 440                 445 ggt aaa cca atc ggt aag gaa ggt tac tac tgg ctg aaa atc cac ggt      1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag      1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca      1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt      1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat      1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag      1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac      1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag      1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
        595                 600                 605 gtc aag ctt ggc act aag gca ctg gct ggt caa tgg ctg gct tac ggt      1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag      2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg      2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag      2112
Val Val Ala Ala Val Glu Ala Met Asn Trp Leu Lys Ser Ala Ala Lys
    690                 695                 700 ctt ctg gct gct gag gtc aaa gat aag aag act gga gag att ctt cgc      2160
Leu Leu Ala Ala Glu Val Lys Asp Lys Lys Thr Gly Glu Ile Leu Arg
705                 710                 715                 720
```

```
aag cgt tgc gct gtg cat tgg gta act cct gat ggt ttc cct gtg tgg      2208
Lys Arg Cys Ala Val His Trp Val Thr Pro Asp Gly Phe Pro Val Trp
            725                 730                 735 cag gaa tac aag aag cct att cag acg cgc ttg aac ctg atg ttc ctc      2256
Gln Glu Tyr Lys Lys Pro Ile Gln Thr Arg Leu Asn Leu Met Phe Leu
        740                 745                 750 ggt cag ttc cgc tta cag cct acc att aac acc aac aaa gat agc gag      2304
Gly Gln Phe Arg Leu Gln Pro Thr Ile Asn Thr Asn Lys Asp Ser Glu
    755                 760                 765 att gat gca cac aaa cag gag tct ggt atc gct cct aac ttt gta cac      2352
Ile Asp Ala His Lys Gln Glu Ser Gly Ile Ala Pro Asn Phe Val His
770                 775                 780 agc cta gac ggt agc cac ctt cgt aag act gta gtg tgg gca cac gag      2400
Ser Leu Asp Gly Ser His Leu Arg Lys Thr Val Val Trp Ala His Glu
785                 790                 795                 800 aag tac gga atc gaa tct ttt gca ctg att cac gac tcc ttc ggt acc      2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg      2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag      2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt      2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc      2640
Pro Ala Lys Gly Asn Leu Asn Leu Arg Asp Ile Leu Glu Ser Asp Phe
865                 870                 875                 880 gcg ttc gcg taa                                                       2652
Ala Phe Ala <210> SEQ ID NO 36
<211> LENGTH: 883
<212> TYPE: PRT
<213> ORGANISM: Artificial Sequence
<220> FEATURE:
<223> OTHER INFORMATION: Synthetic T7 RNA polymerase protein

<400> SEQUENCE: 36

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140
```

```
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Glu Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575
```

```
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Val Leu Glu Asp Thr Ile Gln
            645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
            725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
770                 775                 780
Ser Leu Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
            805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
            835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 37
<211> LENGTH: 34
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (16)..(17)
<223> OTHER INFORMATION: n is a, c, g, or t

<400> SEQUENCE: 37
gtagggcacg tctacnnkaa agcatttatg caag                              34

<210> SEQ ID NO 38
<211> LENGTH: 25
<212> TYPE: DNA
```

```
<213> ORGANISM: Artificial Sequence
<220> FEATURE:
<223> OTHER INFORMATION: Synthetic oligonucleotide primer

<400> SEQUENCE: 38
gtcgatgtct tccggtttca tcggg                                             25

<210> SEQ ID NO 39
<211> LENGTH: 34
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (18)..(19)
<223> OTHER INFORMATION: n is a, c, g, or t

<400> SEQUENCE: 39
cttgcataaa tgctttmnng tagacgtgcc ctac                                   34

<210> SEQ ID NO 40
<211> LENGTH: 37
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (18)..(19)
<223> OTHER INFORMATION: n is a, c, g, or t

<400> SEQUENCE: 40
ctaactttgt acacagcnnk gacggtagcc accttcg                                37

<210> SEQ ID NO 41
<211> LENGTH: 37
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (19)..(20)
<223> OTHER INFORMATION: n is a, c, g, or t

<400> SEQUENCE: 41
cgaaggtggc taccgtcmnn gctgtgtaca aagttag                                37

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 42
gtgaccgatg agaacactgg                                                   20

<210> SEQ ID NO 43
<211> LENGTH: 2652
<212> TYPE: DNA
<213> ORGANISM: Artificial Sequence
<220> FEATURE:
<223> OTHER INFORMATION: Synthetic T7 RNA polymerase

<400> SEQUENCE: 43 atg aac acg att aac atc gct aag aac gac ttc tct gac atc gaa ctg     48
Met Asn Thr Ile Asn Ile Ala Lys Asn Asp Phe Ser Asp Ile Glu Leu
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

| | | | | | | | | | | | | | | | | |
|---|---|---|---|---|---|---|---|---|---|---|---|---|---|---|---|---|
| gct | gct | atc | ccg | ttc | aac | act | ctg | gct | gac | cat | tac | ggt | gag | cgt | tta | 96 |
| Ala | Ala | Ile | Pro | Phe | Asn | Thr | Leu | Ala | Asp | His | Tyr | Gly | Glu | Arg | Leu | |
| | | | 20 | | | | | 25 | | | | | 30 | | | |
| gct | cgc | gaa | cag | ttg | gcc | ctt | gag | cat | gag | tct | tac | gag | atg | ggt | gaa | 144 |
| Ala | Arg | Glu | Gln | Leu | Ala | Leu | Glu | His | Glu | Ser | Tyr | Glu | Met | Gly | Glu | |
| | | 35 | | | | | 40 | | | | | 45 | | | | |
| gca | cgc | ttc | cgc | aag | atg | ttt | gag | cgt | caa | ctt | aaa | gct | ggt | gag | gtt | 192 |
| Ala | Arg | Phe | Arg | Lys | Met | Phe | Glu | Arg | Gln | Leu | Lys | Ala | Gly | Glu | Val | |
| | 50 | | | | | 55 | | | | | 60 | | | | | |
| gcg | gat | aac | gct | gcc | gcc | aag | cct | ctc | atc | act | acc | cta | ctc | cct | aag | 240 |
| Ala | Asp | Asn | Ala | Ala | Ala | Lys | Pro | Leu | Ile | Thr | Thr | Leu | Leu | Pro | Lys | |
| 65 | | | | | 70 | | | | | 75 | | | | | 80 | |
| atg | att | gca | cgc | atc | aac | gac | tgg | ttt | gag | gaa | gtg | aaa | gct | aag | cgc | 288 |
| Met | Ile | Ala | Arg | Ile | Asn | Asp | Trp | Phe | Glu | Glu | Val | Lys | Ala | Lys | Arg | |
| | | | | 85 | | | | | 90 | | | | | 95 | | |
| ggc | aag | cgc | ccg | aca | gcc | ttc | cag | ttc | ctg | caa | gaa | atc | aag | ccg | gaa | 336 |
| Gly | Lys | Arg | Pro | Thr | Ala | Phe | Gln | Phe | Leu | Gln | Glu | Ile | Lys | Pro | Glu | |
| | | | 100 | | | | | 105 | | | | | 110 | | | |
| gcc | gta | gcg | tac | atc | acc | att | aag | acc | act | ctg | gct | tgc | cta | acc | agt | 384 |
| Ala | Val | Ala | Tyr | Ile | Thr | Ile | Lys | Thr | Thr | Leu | Ala | Cys | Leu | Thr | Ser | |
| | | 115 | | | | | 120 | | | | | 125 | | | | |
| gct | gac | aat | aca | acc | gtt | cag | gct | gta | gca | agc | gca | atc | ggt | cgg | gcc | 432 |
| Ala | Asp | Asn | Thr | Thr | Val | Gln | Ala | Val | Ala | Ser | Ala | Ile | Gly | Arg | Ala | |
| | 130 | | | | | 135 | | | | | 140 | | | | | |
| att | gag | gac | gag | gct | cgc | ttc | ggt | cgt | atc | cgt | gac | ctt | gaa | gct | aag | 480 |
| Ile | Glu | Asp | Glu | Ala | Arg | Phe | Gly | Arg | Ile | Arg | Asp | Leu | Glu | Ala | Lys | |
| 145 | | | | | 150 | | | | | 155 | | | | | 160 | |
| cac | ttc | aag | aaa | aac | gtt | gag | gaa | caa | ctc | aac | aag | cgc | gta | ggg | cac | 528 |
| His | Phe | Lys | Lys | Asn | Val | Glu | Glu | Gln | Leu | Asn | Lys | Arg | Val | Gly | His | |
| | | | | 165 | | | | | 170 | | | | | 175 | | |
| gtc | tac | gag | aaa | gca | ttt | atg | caa | gtt | gtc | gag | gct | gac | atg | ctc | tct | 576 |
| Val | Tyr | Glu | Lys | Ala | Phe | Met | Gln | Val | Val | Glu | Ala | Asp | Met | Leu | Ser | |
| | | | 180 | | | | | 185 | | | | | 190 | | | |
| aag | ggt | cta | ctc | ggt | ggc | gag | gcg | tgg | tct | tcg | tgg | cat | aag | gaa | gac | 624 |
| Lys | Gly | Leu | Leu | Gly | Gly | Glu | Ala | Trp | Ser | Ser | Trp | His | Lys | Glu | Asp | |
| | | 195 | | | | | 200 | | | | | 205 | | | | |
| tct | att | cat | gta | gga | gta | cgc | tgc | atc | gag | atg | ctc | att | gag | tca | acc | 672 |
| Ser | Ile | His | Val | Gly | Val | Arg | Cys | Ile | Glu | Met | Leu | Ile | Glu | Ser | Thr | |
| | 210 | | | | | 215 | | | | | 220 | | | | | |
| gga | atg | gtt | agc | tta | cac | cgc | caa | aat | gct | ggc | gta | gta | ggt | caa | gac | 720 |
| Gly | Met | Val | Ser | Leu | His | Arg | Gln | Asn | Ala | Gly | Val | Val | Gly | Gln | Asp | |
| 225 | | | | | 230 | | | | | 235 | | | | | 240 | |
| tct | gag | act | atc | gaa | ctc | gca | cct | gaa | tac | gct | gag | gct | atc | gca | acc | 768 |
| Ser | Glu | Thr | Ile | Glu | Leu | Ala | Pro | Glu | Tyr | Ala | Glu | Ala | Ile | Ala | Thr | |
| | | | | 245 | | | | | 250 | | | | | 255 | | |
| cgt | gca | ggt | gcg | ctg | gct | ggc | atc | tct | ccg | atg | ttc | caa | cct | tgc | gta | 816 |
| Arg | Ala | Gly | Ala | Leu | Ala | Gly | Ile | Ser | Pro | Met | Phe | Gln | Pro | Cys | Val | |
| | | | 260 | | | | | 265 | | | | | 270 | | | |
| gtt | cct | cct | aag | ccg | tgg | act | ggc | att | act | ggt | ggc | tat | tgg | gct | | 864 |
| Val | Pro | Pro | Lys | Pro | Trp | Thr | Gly | Ile | Thr | Gly | Gly | Tyr | Trp | Ala | | |
| | | 275 | | | | | 280 | | | | | 285 | | | | |
| aac | ggt | cgt | cgt | cct | ctg | gcg | ctg | gtg | cgt | act | cac | agt | aag | aaa | gca | 912 |
| Asn | Gly | Arg | Arg | Pro | Leu | Ala | Leu | Val | Arg | Thr | His | Ser | Lys | Lys | Ala | |
| | 290 | | | | | 295 | | | | | 300 | | | | | |
| ctg | atg | cgc | tac | gaa | gac | gtt | tac | atg | cct | gag | gtg | tac | aaa | gcg | att | 960 |
| Leu | Met | Arg | Tyr | Glu | Asp | Val | Tyr | Met | Pro | Glu | Val | Tyr | Lys | Ala | Ile | |
| 305 | | | | | 310 | | | | | 315 | | | | | 320 | |
| aac | att | gcg | caa | aac | acc | gca | tgg | aaa | atc | aac | aag | aaa | gtc | cta | gcg | 1008 |
| Asn | Ile | Ala | Gln | Asn | Thr | Ala | Trp | Lys | Ile | Asn | Lys | Lys | Val | Leu | Ala | |

```
                        325                 330                 335
gtc gcc aac gta atc acc aag tgg aag cat tgt ccg gtc gag gac atc      1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac      1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg      1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc      1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc      1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc      1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa      1344
Asn Pro Gln Gly Asn Asp Met Thr Lys Gly Leu Leu Thr Leu Ala Lys
        435                 440                 445 ggt aaa cca atc ggt aag gaa ggt tac tac tgg ctg aaa atc cac ggt      1392
Gly Lys Pro Ile Gly Lys Glu Gly Tyr Tyr Trp Leu Lys Ile His Gly
    450                 455                 460 gca aac tgt gcg ggt gtc gat aag gtt ccg ttc cct gag cgc atc aag      1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca      1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt      1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat      1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag      1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac      1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag      1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
        595                 600                 605 gtc aag ctt ggc act aag gca ctg gct ggt caa tgg ctg gct tac ggt      1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
```

```
                        645                 650                 655
cca gct att gat tcc ggc aag ggt ctg atg ttc act cag ccg aat cag    2016
Pro Ala Ile Asp Ser Gly Lys Gly Leu Met Phe Thr Gln Pro Asn Gln
            660                 665                 670 gct gct gga tac atg gct aag ctg att tgg gaa tct gcg agc gtg acg    2064
Ala Ala Gly Tyr Met Ala Lys Leu Ile Trp Glu Ser Ala Ser Val Thr
            675                 680                 685 gtg gta gct gcg gtt gaa gca atg aac tgg ctt aag tct gct gct aag    2112
Val Val Ala Ala Val Glu Ala Met Asn Trp Leu Lys Ser Ala Ala Lys
            690                 695                 700 ctt ctg gct gct gag gtc aaa gat aag aag act gga gag att ctt cgc    2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg    2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
            755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
            770                 775                 780 agc cta gac ggt agc cac ctt cgt aag act gta gtg tgg gca cac gag    2400
Ser Leu Asp Gly Ser His Leu Arg Lys Thr Val Val Trp Ala His Glu
785                 790                 795                 800 aag tac gga atc gaa tct ttt gca ctg att cac gac tcc ttc ggt acc    2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
            835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                    2652
Ala Phe Ala <210> SEQ ID NO 44
<211> LENGTH: 883
<212> TYPE: PRT
<213> ORGANISM: Artificial Sequence
<220> FEATURE:
<223> OTHER INFORMATION: Synthetic T7 RNA polymerase

<400> SEQUENCE: 44

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45
```

```
Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                     85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
 130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Glu Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
 290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
 370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480
```

```
Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Ala Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Leu Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 45
```

```
<211> LENGTH: 2652
<212> TYPE: DNA
<213> ORGANISM: Artificial Sequence
<220> FEATURE:
<223> OTHER INFORMATION: Synthetic T7 RNA polymerase

<400> SEQUENCE: 45 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
                20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
            35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
        50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
                100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
            115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
        130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac     528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct     576
Val Tyr Lys Lys Ala Phe Met Gln Val Val Glu Ala Asp Met Leu Ser
                180                 185                 190 aag ggt cta ctc ggt ggc gag gcg tgg tct tcg tgg cat aag gaa gac     624
Lys Gly Leu Leu Gly Gly Glu Ala Trp Ser Ser Trp His Lys Glu Asp
            195                 200                 205 tct att cat gta gga gta cgc tgc atc gag atg ctc att gag tca acc     672
Ser Ile His Val Gly Val Arg Cys Ile Glu Met Leu Ile Glu Ser Thr
        210                 215                 220 gga atg gtt agc tta cac cgc caa aat gct ggc gta gta ggt caa gac     720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc     768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta     816
Arg Ala Gly Ala Leu Ala Gly Ile Ser Pro Met Phe Gln Pro Cys Val
                260                 265                 270 gtt cct cct aag ccg tgg act ggc att act ggt ggt ggc tat tgg gct     864
Val Pro Pro Lys Pro Trp Thr Gly Ile Thr Gly Gly Gly Tyr Trp Ala
            275                 280                 285
```

```
aac ggt cgt cgt cct ctg gcg ctg gtg cgt act cac agt aag aaa gca      912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
        340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
        370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc     1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
            435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
        450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
        500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
            515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
        530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag     1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac     1776
Lys Val Asn Glu Ile Leu Gln Ala Asp Ala Ile Asn Gly Thr Asp Asn
        580                 585                 590 gaa gta gtt acc gtg acc gat gag aac act ggt gaa atc tct gag aaa     1824
Glu Val Val Thr Val Thr Asp Glu Asn Thr Gly Glu Ile Ser Glu Lys
            595                 600                 605
```

```
gtc aag ctt ggc act aag gca ctg gct ggt caa tgg ctg gct tac ggt      1872
Val Lys Leu Gly Thr Lys Ala Leu Ala Gly Gln Trp Leu Ala Tyr Gly
    610             615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625             630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag      2016
Pro Ala Ile Asp Ser Gly Lys Gly Leu Met Phe Thr Gln Pro Asn Gln
            660                 665                 670 gct gct gga tac atg gct aag ctg att tgg gaa tct gcg agc gtg acg      2064
Ala Ala Gly Tyr Met Ala Lys Leu Ile Trp Glu Ser Ala Ser Val Thr
        675                 680                 685 gtg gta gct gcg gtt gaa gca atg aac tgg ctt aag tct gct gct aag      2112
Val Val Ala Ala Val Glu Ala Met Asn Trp Leu Lys Ser Ala Ala Lys
    690                 695                 700 ctt ctg gct gct gag gtc aaa gat aag aag act gga gag att ctt cgc      2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg      2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc      2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag      2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac      2352
Ile Asp Ala His Lys Gln Glu Ser Gly Ile Ala Pro Asn Phe Val His
    770                 775                 780 agc cta gac ggt agc cac ctt cgt aag act gta gtg tgg gca cac gag      2400
Ser Leu Asp Gly Ser His Leu Arg Lys Thr Val Val Trp Ala His Glu
785                 790                 795                 800 aag tac gga atc gaa tct ttt gca ctg att cac gac tcc ttc ggt acc      2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg      2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag      2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt      2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc      2640
Pro Ala Lys Gly Asn Leu Asn Leu Arg Asp Ile Leu Glu Ser Asp Phe
865                 870                 875                 880 gcg ttc gcg taa                                                      2652
Ala Phe Ala
```

<210> SEQ ID NO 46
<211> LENGTH: 883
<212> TYPE: PRT
<213> ORGANISM: Artificial Sequence
<220> FEATURE:
<223> OTHER INFORMATION: Synthetic T7 RNA polymerase

<400> SEQUENCE: 46

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65              70                  75                      80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
```

-continued

```
                420             425             430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
        450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
        610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Ala Ser Val Thr
        675                 680                 685
Val Val Ala Ala Val Glu Ala Met Asn Trp Leu Lys Ser Ala Ala Lys
        690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
        770                 775                 780
Ser Leu Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
```

```
Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 47
<211> LENGTH: 20
<212> TYPE: DNA
<213> ORGANISM: Artificial Sequence
<220> FEATURE:
<223> OTHER INFORMATION: Synthetic scissor oligonucleotide

<400> SEQUENCE: 47
gatagcggga aagggatcgc                                                     20

<210> SEQ ID NO 48
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 48
aattctaata cgactcacta tagggagact atcggtaaca gtgatgat                      48

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 49
ctgactcagg tgctgttgaa                                                     20

<210> SEQ ID NO 50
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 50
agcgtagagg caaaagaaag tgggac                                              26

<210> SEQ ID NO 51
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 51
gatttgggaa tctgcgagcg tgacggtgg                                           29

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 52
gtgacatctt agagtcggac ttcgc                                               25
```

<210> SEQ ID NO 53
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 53
ccaccgtcac gctcgcagat tcccaaatc                                29

<210> SEQ ID NO 54
<211> LENGTH: 2652
<212> TYPE: DNA
<213> ORGANISM: Artificial Sequence
<220> FEATURE:
<223> OTHER INFORMATION: Synthetic T7 RNA polymerase

<400> SEQUENCE: 54

```
atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac     528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct     576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac     624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc     672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac     720
Gly Met Val Ser Leu His Arg Gln Asn Ala Gly Val Val Gly Gln Asp
```

```
                225                 230                 235                 240
tct gag act atc gaa ctc gca cct gaa tac gct gag gct atc gca acc      768
Ser Glu Thr Ile Glu Leu Ala Pro Glu Tyr Ala Glu Ala Ile Ala Thr
                    245                 250                 255 cgt gca ggt gcg ctg gct ggc atc tct ccg atg ttc caa cct tgc gta      816
Arg Ala Gly Ala Leu Ala Gly Ile Ser Pro Met Phe Gln Pro Cys Val
                260                 265                 270 gtt cct cct aag ccg tgg act ggc att act ggt ggc tat tgg gct          864
Val Pro Pro Lys Pro Trp Thr Gly Ile Thr Gly Gly Tyr Trp Ala
            275                 280                 285 aac ggt cgt cgt cct ctg gcg ctg gtg cgt act cac agt aag aaa gca      912
Asn Gly Arg Arg Pro Leu Ala Leu Val Arg Thr His Ser Lys Lys Ala
        290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
                340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
        370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc     1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
                420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
            435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
                500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
            515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
        530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
```

-continued

| | | | | |
|---|---|---|---|---|
| 545 | 550 | 555 | 560 | |
| ttg ctt cct agt gaa acc gtt cag gac atc tac ggg att gtt gct aag<br>Leu Leu Pro Ser Glu Thr Val Gln Asp Ile Tyr Gly Ile Val Ala Lys<br>565 570 575 | | | | 1728 |
| aaa gtc aac gag att cta caa gca gac gca atc aat ggg acc gat aac<br>Lys Val Asn Glu Ile Leu Gln Ala Asp Ala Ile Asn Gly Thr Asp Asn<br>580 585 590 | | | | 1776 |
| gaa gta gtt acc gtg acc gat gag aac act ggt gaa atc tct gag aaa<br>Glu Val Val Thr Val Thr Asp Glu Asn Thr Gly Glu Ile Ser Glu Lys<br>595 600 605 | | | | 1824 |
| gtc aag ctt ggc act aag gca ctg gct ggt caa tgg ctg gct tac ggt<br>Val Lys Leu Gly Thr Lys Ala Leu Ala Gly Gln Trp Leu Ala Tyr Gly<br>610 615 620 | | | | 1872 |
| gtt act cgc agt gtg act aag cgt tca gtc atg acg ctg gct tac ggg<br>Val Thr Arg Ser Val Thr Lys Arg Ser Val Met Thr Leu Ala Tyr Gly<br>625 630 635 640 | | | | 1920 |
| tcc aaa gag ttc ggc ttc cgt caa caa gtg ctg gaa gat acc att cag<br>Ser Lys Glu Phe Gly Phe Arg Gln Gln Val Leu Glu Asp Thr Ile Gln<br>645 650 655 | | | | 1968 |
| cca gct att gat tcc ggc aag ggt ctg atg ttc act cag ccg aat cag<br>Pro Ala Ile Asp Ser Gly Lys Gly Leu Met Phe Thr Gln Pro Asn Gln<br>660 665 670 | | | | 2016 |
| gct gct gga tac atg gct aag ctg att tgg gaa tct gcg agc gtg acg<br>Ala Ala Gly Tyr Met Ala Lys Leu Ile Trp Glu Ser Ala Ser Val Thr<br>675 680 685 | | | | 2064 |
| gtg gta gct gcg gtt gaa gca atg aac tgg ctt aag tct gct gct aag<br>Val Val Ala Ala Val Glu Ala Met Asn Trp Leu Lys Ser Ala Ala Lys<br>690 695 700 | | | | 2112 |
| ctt ctg gct gct gag gtc aaa gat aag aag act gga gag att ctt cgc<br>Leu Leu Ala Ala Glu Val Lys Asp Lys Lys Thr Gly Glu Ile Leu Arg<br>705 710 715 720 | | | | 2160 |
| aag cgt tgc gct gtg cat tgg gta act cct gat ggt ttc cct gtg tgg<br>Lys Arg Cys Ala Val His Trp Val Thr Pro Asp Gly Phe Pro Val Trp<br>725 730 735 | | | | 2208 |
| cag gaa tac aag aag cct att cag acg cgc ttg aac ctg atg ttc ctc<br>Gln Glu Tyr Lys Lys Pro Ile Gln Thr Arg Leu Asn Leu Met Phe Leu<br>740 745 750 | | | | 2256 |
| ggt cag ttc cgc tta cag cct acc att aac acc aac aaa gat agc gag<br>Gly Gln Phe Arg Leu Gln Pro Thr Ile Asn Thr Asn Lys Asp Ser Glu<br>755 760 765 | | | | 2304 |
| att gat gca cac aaa cag gag tct ggt atc gct cct aac ttt gta cac<br>Ile Asp Ala His Lys Gln Glu Ser Gly Ile Ala Pro Asn Phe Val His<br>770 775 780 | | | | 2352 |
| agc caa gac ggt agc cac ctt cgt aag act gta gtg tgg gca cac gag<br>Ser Gln Asp Gly Ser His Leu Arg Lys Thr Val Val Trp Ala His Glu<br>785 790 795 800 | | | | 2400 |
| aag tac gga atc gaa tct ttt gca ctg att cac gac tcc ttc ggt acc<br>Lys Tyr Gly Ile Glu Ser Phe Ala Leu Ile His Asp Ser Phe Gly Thr<br>805 810 815 | | | | 2448 |
| att ccg gct gac gct gcg aac ctg ttc aaa gca gtg cgc gaa act atg<br>Ile Pro Ala Asp Ala Ala Asn Leu Phe Lys Ala Val Arg Glu Thr Met<br>820 825 830 | | | | 2496 |
| gtt gac aca tat gag tct tgt gat gta ctg gct gat ttc tac gac cag<br>Val Asp Thr Tyr Glu Ser Cys Asp Val Leu Ala Asp Phe Tyr Asp Gln<br>835 840 845 | | | | 2544 |
| ttc gct gac cag ttg cac gag tct caa ttg gac aaa atg cca gca ctt<br>Phe Ala Asp Gln Leu His Glu Ser Gln Leu Asp Lys Met Pro Ala Leu<br>850 855 860 | | | | 2592 |
| ccg gct aaa ggt aac ttg aac ctc cgt gac atc tta gag tcg gac ttc<br>Pro Ala Lys Gly Asn Leu Asn Leu Arg Asp Ile Leu Glu Ser Asp Phe | | | | 2640 |

```
                865                 870                 875                 880
gcg ttc gcg taa                                                                    2652
Ala Phe Ala <210> SEQ ID NO 55
<211> LENGTH: 883
<212> TYPE: PRT
<213> ORGANISM: Artificial Sequence
<220> FEATURE:
<223> OTHER INFORMATION: Synthetic T7 RNA polymerase

<400> SEQUENCE: 55

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350
```

```
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Ala Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
            725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
```

```
                     770                 775                 780
Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 56
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 56
ctttgtacac agcatggacg gtagccac                                    28

<210> SEQ ID NO 57
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 57
gtggctaccg tccatgctgt gtacaaag                                    28

<210> SEQ ID NO 58
<211> LENGTH: 2652
<212> TYPE: DNA
<213> ORGANISM: Artificial Sequence
<220> FEATURE:
<223> OTHER INFORMATION: Synthetic T7 RNA polymerase

<400> SEQUENCE: 58 atg aac acg att aac atc gct aag aac gac ttc tct gac atc gaa ctg    48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta    96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa   144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt   192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag   240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc   288
Met Ile Ala Arg Ile Asn Asp Trp Phe Glu Glu Val Lys Ala Lys Arg
                85                  90                  95
```

```
ggc aag cgc ccg aca gcc ttc cag ttc ctg caa gaa atc aag ccg gaa    336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt    384
Ala Val Ala Tyr Ile Thr Ile Lys Thr Thr Leu Ala Cys Leu Thr Ser
            115                 120                 125 gct gac aat aca acc gtt cag gct gta gca agc gca atc ggt cgg gcc    432
Ala Asp Asn Thr Thr Val Gln Ala Val Ala Ser Ala Ile Gly Arg Ala
130                 135                 140 att gag gac gag gct cgc ttc ggt cgt atc cgt gac ctt gaa gct aag    480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac    528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct    576
Val Tyr Lys Lys Ala Phe Met Gln Val Val Glu Ala Asp Met Leu Ser
                180                 185                 190 aag ggt cta ctc ggt ggc gag gcg tgg tct tcg tgg cat aag gaa gac    624
Lys Gly Leu Leu Gly Gly Glu Ala Trp Ser Ser Trp His Lys Glu Asp
            195                 200                 205 tct att cat gta gga gta cgc tgc atc gag atg ctc att gag tca acc    672
Ser Ile His Val Gly Val Arg Cys Ile Glu Met Leu Ile Glu Ser Thr
210                 215                 220 gga atg gtt agc tta cac cgc caa aat gct ggc gta gta ggt caa gac    720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc    768
Ser Glu Thr Ile Glu Leu Ala Pro Glu Tyr Ala Glu Ala Ile Ala Thr
            245                 250                 255 cgt gca ggt gcg ctg gct ggc atc tct ccg atg ttc caa cct tgc gta    816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct    864
Val Pro Pro Lys Pro Trp Thr Gly Ile Thr Gly Gly Gly Tyr Trp Ala
            275                 280                 285 aac ggt cgt cgt cct ctg gcg ctg gtg cgt act cac agt aag aaa gca    912
Asn Gly Arg Arg Pro Leu Ala Leu Val Arg Thr His Ser Lys Lys Ala
290                 295                 300 ctg atg cgc tac gaa gac gtt tac atg cct gag gtg tac aaa gcg att    960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg   1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc   1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac   1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg   1152
Met Asn Pro Glu Ala Leu Thr Ala Trp Lys Arg Ala Ala Ala Ala Val
370                 375                 380 tac cgc aag gac aag gct cgc aag tct cgc cgt atc agc ctt gag ttc   1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc   1248
Met Leu Glu Gln Ala Asn Lys Phe Ala Asn His Lys Ala Ile Trp Phe
                405                 410                 415
```

```
cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
        435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
    450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag     1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac     1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa     1824
Glu Val Val Thr Val Thr Asp Glu Asn Thr Gly Glu Ile Ser Glu Lys
        595                 600                 605 gtc aag ctt ggc act aag gca ctg gct ggt caa tgg ctg gct tac ggt     1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg     1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag     1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag     2016
Pro Ala Ile Asp Ser Gly Lys Gly Leu Met Phe Thr Gln Pro Asn Gln
            660                 665                 670 gct gct gga tac atg gct aag ctg att tgg gaa tct gcg agc gtg acg     2064
Ala Ala Gly Tyr Met Ala Lys Leu Ile Trp Glu Ser Ala Ser Val Thr
        675                 680                 685 gtg gta gct gcg gtt gaa gca atg aac tgg ctt aag tct gct gct aag     2112
Val Val Ala Ala Val Glu Ala Met Asn Trp Leu Lys Ser Ala Ala Lys
    690                 695                 700 ctt ctg gct gct gag gtc aaa gat aag aag act gga gag att ctt cgc     2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg     2208
Lys Arg Cys Ala Val His Trp Val Thr Pro Asp Gly Phe Pro Val Trp
                725                 730                 735
```

```
cag gaa tac aag aag cct att cag acg cgt ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
770                 775                 780 agc atg gac ggt agc cac ctt cgt aag act gta gtg tgg gca cac gag    2400
Ser Met Asp Gly Ser His Leu Arg Lys Thr Val Val Trp Ala His Glu
785                 790                 795                 800 aag tac gga atc gaa tct ttt gca ctg att cac gac tcc ttc ggt acc    2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                    2652
Ala Phe Ala
```

<210> SEQ ID NO 59
<211> LENGTH: 883
<212> TYPE: PRT
<213> ORGANISM: Artificial Sequence
<220> FEATURE:
<223> OTHER INFORMATION: Synthetic T7 RNA polymerase

<400> SEQUENCE: 59

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
```

```
                        165                 170                 175
Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395             400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590
```

-continued

```
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
        610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Ala Ser Val Thr
        675                 680                 685
Val Val Ala Ala Val Glu Ala Met Asn Trp Leu Lys Ser Ala Ala Lys
        690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
770                 775                 780
Ser Met Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala
```

US 8,551,752 B2

RNA POLYMERASE MUTANT WITH IMPROVED FUNCTIONS

CROSS REFERENCE TO RELATED APPLICATIONS

This application is a National Stage of International Application No. PCT/JP2009/064323 filed Aug. 7, 2009, claiming priority based on Japanese Patent Application No. 2008-205491 filed Aug. 8, 2008, Japanese Patent Application No. 2009-038979 filed Feb. 23, 2009 and Japanese Patent Application No. 2009-038980 filed Feb. 23, 2009, the contents of all of which are incorporated herein by reference in their entirety.

TECHNICAL FIELD

The present invention relates to an RNA polymerase having improved function, and more particularly, to an RNA polymerase having improved thermal stability and/or specific activity by being introduced a mutation into a portion of an amino acid sequence of the wild-type RNA polymerase, a method for producing said RNA polymerase, and a method for producing RNA by using said RNA polymerase.

BACKGROUND ART

The present invention relates to a mutant RNA polymerase obtained from a bacteriophage that has improved thermal stability and/or specific activity in comparison with a wild type under high-temperature conditions, and more particularly, to T7 RNA polymerase. Although examples of bacteriophages that can infect *Escherichia coli* include T3, T7, ϕI, ϕII, W31, H, Y, A1, croC21, C22 and C23, RNA polymerase encoded by a T7 phage is T7 RNA polymerase.

The first characteristic of T7 RNA polymerase is high selectivity with respect to a promoter sequence. Although T7 RNA polymerase binds to its own unique promoter sequence, it does not bind with other promoter sequences even if they are promoter sequences of other bacteriophages. Due to this high selectivity, RNA polymerase transcription reactions can be reliably improved with respect to its own genome instead of the host genome.

Next, different from other polymerases, T7 RNA polymerase has a series of functions that enable it to recognize a promoter, begin transcription, elongate the RNA transcription product and terminate transcription without requiring a cofactor, and is able to elongate RNA five times faster than *E. coli* RNA polymerase.

Moreover, since it is a single-stranded protein having a molecular weight of 98.6 kDa and 883 amino acids, it enables inexpensive, large-volume production of enzymes.

As a result of having the advantages described above, T7 RNA polymerase is aggressively used in various fields, examples of which include in vitro transcription and a high expression system in *E. coli* (U.S. Pat. No. 4,952,496: Patent Document 1), a cell-free protein synthesis system, a base sequencing method (Japanese Unexamined Patent Publication No. H11-18799: Patent Document 2), and an isothermal nucleic acid amplification method. The following provides a detailed explanation of the TRC method, which is a type of isothermal nucleic acid amplification method (Japanese Unexamined Patent Publication No. 2000-14400: Patent Document 3, and Ishiguro, T. et al., Analytical Biochemistry, 314, 77-86 (2003): Non-Patent Document 1).

The TRC method is a method for amplifying a target RNA containing a specific RNA sequence by utilizing a concerted action between DNA-dependent RNA polymerase and reverse transcriptase. Namely, by use of a primer specific to the target RNA which comprises a T7 promoter sequence, reverse transcriptase and ribonuclease H, a double-stranded DNA comprising the promotor sequence is synthesized, and then RNA composed of the specific RNA sequence is synthesized by use of a T7 RNA polymerase. The synthesized RNA is used as a template for synthesizing double-stranded DNA that contains the aforementioned promoter sequence, thereby the aforementioned reaction is carried out in the manner of chain reaction. Differing from the case of amplifying by the PCR method, since amplification of nucleic acids by the TRC method enables the reaction to be carried out at a constant temperature, it has the advantage of eliminating the need for complex temperature control. However, when nucleic acid amplification is carried out with the TRC method using wild-type T7 RNA polymerase, reduction in nucleic acid amplification efficiency is observed at temperatures of 46° C. or higher due to a decrease in activity of the T7 RNA polymerase. Consequently, nucleic acid amplification using the current TRC method is typically carried out under comparatively low temperature conditions in the order of 40 to 45° C. However, RNA has a tendency of assuming a complex, higher order structure under low temperature conditions, and this has made it difficult to design primers capable of highly sensitive detection in the TRC method. Consequently, there has been a need for T7 RNA polymerase that demonstrates high thermal stability and/or high specific activity even under temperature conditions of 46° C. or higher.

Since systems have been established for measuring T7 RNA polymerase activity (Ikeda, R. A. et al., Biochemistry, 31, 9073-9080 (1992): Non-Patent Document 2, and Ikeda, R. A. et al., Nucl. Acid Res., 20, 2517-2524 (1992): Non-Patent Document 3), several RNA polymerases have been produced that have various improved functions by mutation. Examples of such RNA polymerases include an enzyme the promoter sequence which it recognizes had been altered through amino acid substitution (U.S. Pat. No. 5,385,834: Patent Document 4), an enzyme having enhanced specific activity and thermal stability at high temperatures (Japanese Unexamined Patent Application Publication (Translation of PCT Application) No. 2003-525627: Patent Document 5), and an enzyme having enhanced 3'-deoxyribonucleotide uptake function through amino acid deletion and substitution (Japanese Unexamined Patent Publication No. 2003-61683: Patent Document 6).

SUMMARY OF THE INVENTION

An object of the present invention is to provide a T7 RNA polymerase having improved thermal stability and/or specific activity in comparison with the wild type, and a production method thereof.

As a result of conducting studies to solve the aforementioned problems, the inventors of the present invention found amino acid sites for which thermal stability or specific activity is improved by substituting the amino acid sequence of wild-type T7 RNA polymerase using genetic engineering techniques, and succeeded in producing a mutant having improved thermal stability or specific activity in comparison with a wild strain. Moreover, the inventors of the present invention succeeded at producing a mutant having improved thermal stability and specific activity by combining a mutation of amino acid sites that improve thermal stability and mutation of amino acid sites that improve specific activity.

More specifically, a T7 RNA polymerase, in which at least amino acid residues corresponding to glutamine at position 768 and/or lysine at position 179 of the amino acid sequence composing the wild-type T7 RNA polymerase shown in SEQ ID NO: 6, have been substituted with other amino acids was found to have improved thermal stability and/or specific activity in comparison with wild-type T7 RNA polymerase.

Moreover, thermal stability and/or specific activity were found to improve in comparison with wild-type T7 RNA polymerase by substituting an amino acid residue at a different site from the above sites, namely an amino acid residue corresponding to valine at position 685, with another amino acid.

In addition, a T7 RNA polymerase mutant having further improved thermal stability and/or specific activity was able to be obtained by combining each of the aforementioned amino acid residues.

Namely, the present invention includes the following inventions:

(1) a T7 RNA polymerase mutant characterized by having improved thermal stability and/or specific activity in comparison with wild-type T7-like bacteriophage RNA polymerase, wherein at least one amino acid residue corresponding to at least one of the amino acid residues selected from the group consisting of glutamine at position 786, lysine at position 179 and valine at position 685 of the amino acid sequence that composes wild-type T7 RNA polymerase shown in SEQ ID NO: 6, is substituted with another amino acid;

(2) a T7 RNA polymerase mutant characterized by having improved thermal stability and/or specific activity in comparison with wild-type T7-like bacteriophage RNA polymerase, wherein at least the amino acid residue corresponding to glutamine at position 786 of the amino acid sequence that composes wild-type T7 RNA polymerase shown in SEQ ID NO: 6 is substituted with a hydrophobic amino acid;

(3) a T7 RNA polymerase mutant characterized by having improved thermal stability and/or specific activity in comparison with wild-type T7-like bacteriophage RNA polymerase, wherein at least the amino acid residue corresponding to glutamine at position 786 of the amino acid sequence that composes wild-type T7 RNA polymerase shown in SEQ ID NO: 6 is substituted with leucine or methionine;

(4) the T7 RNA polymerase mutant described in (2) or (3) characterized by having improved thermal stability and specific activity as compared with wild-type T7-like bacteriophage RNA polymerase, wherein at least the amino acid residue corresponding to lysine at position 179 of the amino acid sequence that composes wild-type T7 RNA polymerase shown in SEQ ID NO: 6 is further substituted with any of glutamate, asparagine or cysteine;

(5) a T7 RNA polymerase mutant characterized by having improved thermal stability and/or specific activity in comparison with wild-type T7-like bacteriophage RNA polymerase, wherein at least the amino acid residue corresponding to lysine at position 179 of the amino acid sequence that composes wild-type T7 RNA polymerase shown in SEQ ID NO: 6 is substituted with any of glutamate, asparagine or cysteine;

(6) the T7 RNA polymerase mutant described in any of (2) to (5) characterized by having improved thermal stability and specific activity as compared with wild-type T7-like bacteriophage RNA polymerase, wherein at least the amino acid residue corresponding to valine at position 685 of the amino acid sequence that composes wild-type T7 RNA polymerase shown in SEQ ID NO: 6 is further substituted with a neutral or weakly hydrophobic amino acid;

(7) the T7 RNA polymerase mutant described in (6) characterized by having improved thermal stability and specific activity as compared with wild-type T7-like bacteriophage RNA polymerase, wherein at least the amino acid residue corresponding to valine at position 685 of the amino acid sequence that composes wild-type T7 RNA polymerase shown in SEQ ID NO: 6 is further substituted with alanine;

(8) a T7 RNA polymerase mutant characterized by having improved thermal stability and/or specific activity in comparison with wild-type T7-like bacteriophage RNA polymerase, wherein at least the amino acid residue corresponding to valine at position 685 of the amino acid sequence that composes wild-type T7 RNA polymerase shown in SEQ ID NO: 6 is substituted with a neutral or weakly hydrophobic amino acid;

(9) a T7 RNA polymerase mutant characterized by having improved thermal stability and/or specific activity in comparison with wild-type T7-like bacteriophage RNA polymerase, wherein at least the amino acid residue corresponding to valine at position 685 of the amino acid sequence that composes wild-type T7 RNA polymerase shown in SEQ ID NO: 6 is substituted with alanine;

(10) a T7 RNA polymerase mutant, wherein the amino acid residue corresponding to valine at position 685 of the amino acid sequence that composes wild-type T7 RNA polymerase shown in SEQ ID NO: 6 is substituted with another amino acid, and the amino acid residues corresponding to lysine at position 179 and/or glutamine at position 786 is (are) substituted with other amino acid residues;

(11) a T7 RNA polymerase mutant, wherein the amino acid residue corresponding to valine at position 685 of the amino acid sequence that composes wild-type T7 RNA polymerase shown in SEQ ID NO: 6 is substituted with alanine, and the amino acid residue corresponding to lysine at position 179 is substituted with glutamate, and/or the amino acid residue corresponding to glutamine at position 786 is substituted with leucine or methionine;

(12) a gene encoding the T7 RNA polymerase mutant of any of (1) to (11);

(13) a cell able to produce T7 RNA polymerase by expressing a gene that encodes the T7 RNA polymerase mutant of any of (1) to (11);

(14) a method for producing T7 RNA polymerase by expressing a gene that encodes the T7 RNA polymerase mutant of any of (1) to (11);

(15) a method for producing RNA using the T7 RNA polymerase mutant of any of (1) to (11); and,

(16) a method for amplifying RNA using the T7 RNA polymerase mutant of any of (1) to (11).

Since the T7 RNA polymerase mutant of the present invention has improved thermal stability and/or specific activity in comparison with wild-type T7 RNA polymerase, it can be expected to enable a transcription reaction to be carried out over a broader temperature range and/or shorten transcription reaction time in comparison with the wild strain.

BEST MODE FOR CARRYING OUT THE INVENTION

Figure 1:
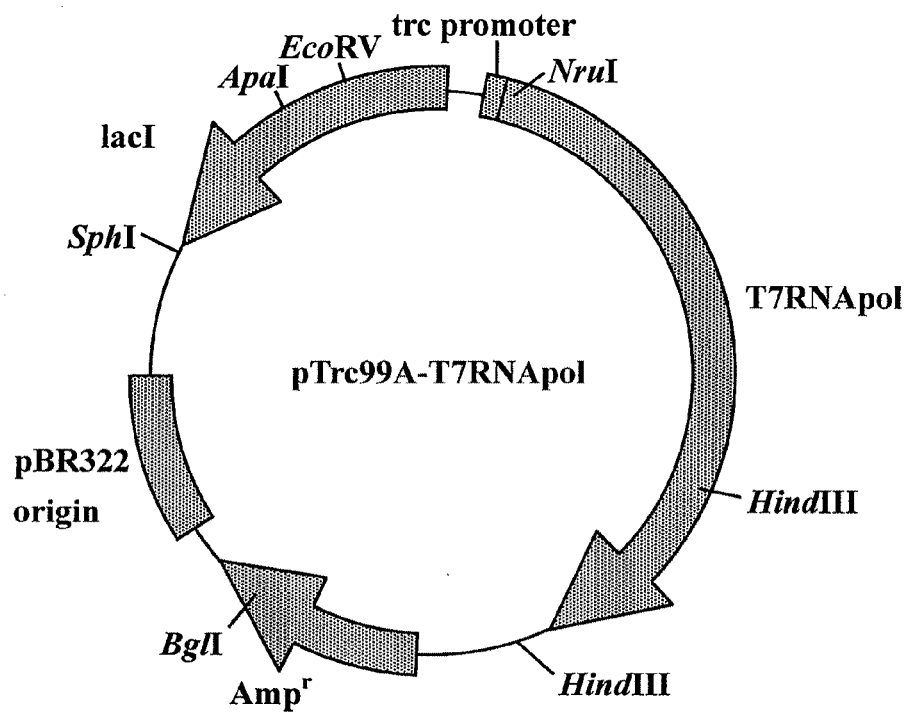
FIG. 1 shows a restriction map of plasmid pTrc99A-T7RNApol cloned from T7 RNA polymerase.

The following provides a detailed explanation of the present invention.

In a first aspect thereof, the T7 RNA polymerase having improved thermal stability and/or specific activity disclosed in the present invention at least has an amino acid residue corresponding to glutamine at position 786 of the amino acid sequence that composes wild-type T7 RNA polymerase shown in SEQ ID NO: 6 substituted with another amino acid, preferably the substituted amino acid is any hydrophobic amino acid (leucine, methionine, phenylalanine or tyrosine), and more preferably the substituted amino acid is leucine or methionine. Furthermore, in the present description, the "amino acid residue corresponding to glutamine at position 786" refers to a glutamine residue at position 786 when based on the amino acid sequence shown in SEQ ID NO: 6, and in the case a polypeptide has been added to or deleted from the 5'-terminal side of T7 RNA polymerase composed of the sequence shown in SEQ ID NO: 6, the position is shifted by the length of the polypeptide that has been added or deleted (for example, in the case of T7 RNA polymerase in which a polypeptide composed of 10 amino acid residues has been added to the 5'-terminal side of T7 RNA polymerase composed of the sequence shown in SEQ ID NO: 6, the "amino acid residue corresponding to glutamine at position 786" becomes glutamine at position 796).

In a second aspect thereof, the T7 RNA polymerase having improved thermal stability and/or specific activity disclosed in the present invention at least has an amino acid residue corresponding to lysine at position 179 of the amino acid sequence that composes wild-type T7 RNA polymerase shown in SEQ ID NO: 6 substituted with another amino acid, preferably the substituted amino acid is glutamate, asparagine or cysteine, and more preferably the substituted amino acid is glutamate. Furthermore, in the present description, the "amino acid residue corresponding to lysine at position 179" refers to a lysine residue at position 179 when based on the amino acid sequence shown in SEQ ID NO: 6, and in the case a polypeptide has been added to or deleted from the 5'-terminal side of T7 RNA polymerase composed of the sequence shown in SEQ ID NO: 6, the position is shifted by the length of the polypeptide that has been added or deleted.

In a third aspect thereof, the T7 RNA polymerase having improved thermal stability and/or specific activity disclosed in the present invention at least has an amino acid residue corresponding to glutamine at position 786 and an amino acid residue corresponding to lysine at position 179 of the amino acid sequence that composes wild-type T7 RNA polymerase shown in SEQ ID NO: 6 each substituted with another amino acid, preferably the amino acid residue at position 786 is substituted with a hydrophobic amino acid (leucine, methionine, phenylalanine or tyrosine) and the amino acid residue at position 179 is substituted with a glutamate, asparagine or cysteine, and more preferably the amino acid residue at position 786 is substituted with leucine or methionine, and the amino acid residue at position 179 is substituted with glutamate, asparagine or cysteine.

In a fourth aspect thereof, the T7 RNA polymerase having improved thermal stability and/or specific activity disclosed in the present invention at least has an amino acid residue corresponding to valine at position 685 of the amino acid sequence that composes wild-type T7 RNA polymerase shown in SEQ ID NO: 6 substituted with another amino acid, preferably the amino acid is a neutral or weakly hydrophobic amino acid (alanine, glycine, serine, threonine, cysteine, asparagine or glutamine), and more preferably the substituted amino acid is alanine. Furthermore, in the present description, the "amino acid residue corresponding to valine at position 685" refers to a valine residue at position 685 when based on the amino acid sequence shown in SEQ ID NO: 6, and in the case a polypeptide has been added to or deleted from the 5'-terminal side of T7 RNA polymerase composed of the sequence shown in SEQ ID NO: 6, the position is shifted by the length of the polypeptide that has been added or deleted (for example, in the case of T7 RNA polymerase in which a polypeptide composed of 10 amino acid residues has been added to the 5'-terminal side of T7 RNA polymerase composed of the sequence shown in SEQ ID NO: 6, the "amino acid residue corresponding to valine at position 685" becomes lysine at position 695).

In a fifth aspect thereof, the T7 RNA polymerase having improved thermal stability and/or specific activity disclosed in the present invention further has an amino acid residue corresponding to lysine at position 179 and/or glutamine at position 786 substituted with another amino acid in addition to substituting an amino acid residue corresponding to valine at position 685 of the amino acid sequence that composes wild-type T7 RNA polymerase shown in SEQ ID NO: 6 each substituted with another amino acid, and preferably the amino acid residue corresponding to lysine at position 179 is substituted with glutamate, and/or the amino acid residue corresponding to glutamine at position 786 is substituted with leucine or methionine, respectively. Furthermore, in the present description, the "amino acid residue corresponding to lysine at position 179 and/or glutamine at position 786" refers to a lysine residue at position 179 and/or a glutamine residue at position 786 when based on the amino acid sequence shown in SEQ ID NO: 6, and in the case a polypeptide has been added to or deleted from the 5'-terminal side of T7 RNA polymerase composed of the sequence shown in SEQ ID NO: 6, the position is shifted by the length of the polypeptide that has been added or deleted.

The T7 RNA polymerase mutant of the present invention can be produced by introducing a mutation into wild-type T7 RNA polymerase gene. Methods for introducing a desired mutation into a prescribed nucleic acid sequence are known among persons with ordinary skill in the art. For example, DNA having a mutation can be constructed by suitably using a known technique such as site-directed mutagenesis, PCR using a degenerate oligonucleotide, or exposure of cell containing nucleic acid to a mutagenic agent or radiation.

Wild-type T7 RNA polymerase gene can be acquired by any method provided it is a method that can be carried out by a person with ordinary skill in the art, and for example, can be acquired by PCR using a suitable primer that has been produced from a T7 phage (such as DSM No. 4623, ATCC 11303-B7 or NCIMB10380) based on the genome information thereof.

There are no particular limitations on the method used to acquire the enzyme of the present invention, and may be a protein synthesized by chemical synthesis, or a recombinant protein produced using genetic recombination technology. In the case of acquiring the enzyme of the present invention using genetic recombination technology, a target enzyme can be obtained by incorporating T7 RNA polymerase gene in a host using a suitable method.

Although various types of cultured cells such as yeast, animal cell lines, plant cells or insect cells can be used for the host used, in the case of T7 RNA polymerase gene, E. coli is preferably used as a host since it is inherently an infection target of a bacteriophage and offers ease in handling. Examples of strains of E. coli used for transformation include, but are not limited to, strain JM109 and strain HB101.

The gene of the present invention can be used by inserting into a suitable vector. There are no particular limitations on the type of vector used in the present invention, and may be a self-replicating vector or may be incorporated in the genome of host cells during introduction into host cells. The vector used in the present invention is preferably an expression vector. In an expression vector, the gene of the present invention is operatively linked to an enzyme required to transcription (such as a promoter). The promoter is a DNA sequence that demonstrates transcription activity in host cells, and can be suitably selected according to the type of host. Examples of promoters capable of being used in E. coli include lac, trp and tac promoters, and in the case of using E. coli for the host, it is convenient to transform a target gene by incorporating in a suitable plasmid. Examples of plasmids used include, but are not limited to, expression plasmids such as pTrc99A (GE Healthcare Bio-Sciences) or pCDF-1b (Takara Bio), and any ordinary E. coli vector may be used provided it can be acquired by a person with ordinary skill in the art. In addition, a sequence useful for enzyme purification may be added to the T7 RNA polymerase gene produced. For example, a signal peptide may be used to obtain an extracellular secreted enzyme, or a gene may be produced so that a tag sequence containing a histidine hexamer is added to a terminal as a signal peptide. The type of signal peptide and method for coupling the signal peptide with the enzyme are inherently not limited to the methods described above, and any signal peptide can be used that is capable of being used by a person with ordinary skill in the art.

The enzyme of the present invention can be acquired by culturing the produced transformant in a suitable nutritive medium under conditions that allow expression of the inserted DNA construct. Isolation and purification methods used for ordinary proteins may be used to isolate and purify the transformant from the culture. For example, in the case the enzyme of the present invention is expressed within cells, after culture, the cells are recovered by centrifugal separation and suspended into a suitable aqueous buffer, and then the cells are lysed by lysozyme treatment or ultrasonic homogenization to obtain a cell-free extract. Moreover, a supernatant obtained by centrifugally separating the cell-free extract is purified using ordinary protein isolation and purification methods. Examples of such methods include solvent extraction, salting out using ammonium salfate, desalination process, precipitation using an organic solvent, anion exchange chromatography using a resin such as diethylaminoethyl (DEAE) Toyopearl (trade name, Tosoh Corp.), hydrophobic chromatography using a resin such as Butyl-Toyopearl or Phenyl-Toyopearl (trade names, Tosoh Corp.), gel filtration using a molecular sieve, affinity chromatography, chromatofocusing and electrophoresis in the manner of isoelectrophoresis, and these techniques may be used alone or in combination to obtain a purified finished product. In addition, it is convenient to use a method that accommodates use of signal peptide, and for example, and purification can be carried out easily by using a histidine hexamer sequence with a nickel column.

The T7 RNA polymerase mutant of the present invention can also be obtained by chemical synthesis, for example, in addition to the methods described above.

The enzyme of the present invention as explained above can be used in various applications as conventionally known T7 RNA polymerase. Namely, the enzyme of the present invention can be used as RNA polymerase to synthesize RNA. More specifically, single-strand RNA synthesis can be carried out by using ribonucleotides (ATP, CTP, GTP, UTP) as substrates as well as using double-stranded DNA having a specific sequence as the template.

Moreover, the RNA polymerase of the present invention can also be used in an isothermal nucleic acid amplification reaction in which a target RNA containing a specific RNA sequence is amplified by a concerted action with reverse transcriptase. Examples of isothermal nucleic acid amplification reactions include TRC (Patent Document 3 and Non-Patent Document 1), NASBA and TMA.

The T7 RNA polymerase mutant of the present invention has improved thermal stability and/or specific activity in comparison with wild-type T7 RNA polymerase. Consequently, it can be stored more easily than the wild type and can be stored for a long period of time. Accordingly, it can provide reagents that are easier to use and can be used over a long period of time.

In addition, since the T7 RNA polymerase mutant of the present invention can be used under higher temperature conditions than the wild type, experimental conditions in transcription reactions and isothermal nucleic acid amplification reactions can be improved, enabling it to be used over a broader temperature range than the wild type regardless of whether the reactions are carried out in vitro or in vivo.

In the case of an isothermal nucleic acid amplification reaction using the TRC method in particular, since the enzyme decreases in activity at a temperature of 46° C. or higher in the case of using wild-type T7 RNA polymerase, it was necessary to carry out the nucleic acid amplification reaction under comparative low temperature conditions of 40 to 45° C. In addition, RNA has a tendency to assume a complex, higher order structure under the aforementioned temperature conditions, and this has made it difficult to design primers capable of highly sensitive detection. On the other hand, the T7 RNA polymerase mutant of the present invention has improved thermal stability and/or specific activity as compared with the wild type under temperature conditions of 46° C. or higher. Consequently, nucleic acid amplification using the TRC method can be carried out under temperature conditions of 46° C. or higher, thereby making it possible to provide a nucleic acid amplification reagent having a shorter detection time than in the prior art. In addition, since it is difficult for RNA to assume a complex higher order structure under high-temperature conditions, primers can be easily designed for more highly sensitive detection. Consequently, by carrying out nucleic acid amplification by TRC under temperature conditions of 46° C. or higher using the T7 RNA polymerase mutant of the present invention, a nucleic acid amplification reagent can be provided that is capable of detecting with higher sensitivity than that of the prior art.

EXAMPLES

Although the following provides a more detailed explanation of the present invention through examples thereof, the present invention is not limited by these examples.

Example 1

Cloning of T7 RNA Polymerase Gene

Cloning of T7 RNA polymerase gene was carried out according to the method described below.
(1) T7 RNA polymerase gene was amplified by PCR by dividing into a first half and a second half using a T7 phage genomic DNA genomic library (Sigma) as template plasmid with the following reagent composition and under the following conditions. Furthermore, among the synthetic DNA primers in the reagent composition, primer FF (SEQ ID NO: 1) and primer FR (SEQ ID NO: 2) were used for the first half of amplification, while primer RF (SEQ ID NO: 3) and primer RR (SEQ ID NO: 4) were used for the second half of amplification.
(Reagent Composition) (total reaction solution volume: 100 μL)

| Synthetic DNA primers | 200 pM each |
| Template plasmid | 100 ng |
| dNTPs | 0.2 mM |
| Taq DNA polymerase (Takara Ex Taq (trade name), Takara Bio) | 0.025 unit/μL |

Buffer provided for the enzyme (Reaction Conditions)
After initially heating for 2 minutes at 94° C., a temperature cycle consisting of 1 minute at 94° C., 30 seconds at 58° C. and 1 minute at 72° C. was repeated 25 times using a thermal cycler (Perkin-Elmer).

(2) The PCR products were purified by subjecting the solution obtained following the PCR reaction to 1% agarose gel electrophoresis, staining the gel with ethidium bromide and cutting out bands of the target products from the stained gel.
(3) The purified PCR product of the first half of PCR was digested with restriction enzymes BspH1 and HindIII (Takara Bio), and reacted with pTrc99A vector (GE Healthcare Biosciences) digested with restriction enzymes NcoI (Takara Bio) and HindIII for 30 minutes at 4° C. using T4 ligase.
(4) The reaction solution of (3) was used to transform E. coli strain JM109 and selectively cultured on LBG/Crb agar medium (1% polypeptone, 0.5% yeast extract, 1% NaCl, 0.5% glucose, 1% agar and 50 μg/mL carbenicillin (pH 7.4)), and the plasmid retained by colonies that grew after culturing overnight at 37° C. was designated as pTrc99A-T7F.
(5) After preparing pTrc99A-T7F in accordance with ordinary methods, the PCR product of the second half was digested with restriction enzymes HindIII and reacted with pTrc99A-T7F digested with HindIII for 30 minutes at 4° C. using T4 ligase.
(6) The reaction solution of (5) was used to transform E. coli strain JM109 and selectively cultured on LBG/Crb agar medium (1% polypeptone, 0.5% yeast extract, 1% NaCl, 0.5% glucose, 1% agar and 50 μg/mL carbenicillin (pH 7.4)), and the plasmid retained by colonies that grew after culturing overnight at 37° C. was designated as pTrc99A-T7RNApol. The restriction map of pTrc99A-T7RNApol is shown in FIG. 1. Furthermore, the T7 RNA polymerase gene was confirmed to be free of unintended mutations by determining the base sequence using the method indicated in Example 6. The gene sequence of the resulting T7 RNA polymerase is shown in SEQ ID NO: 5, while the amino acid sequence is shown in SEQ ID NO: 6.

Example 2

Production of Expression Vector

Figure 2:
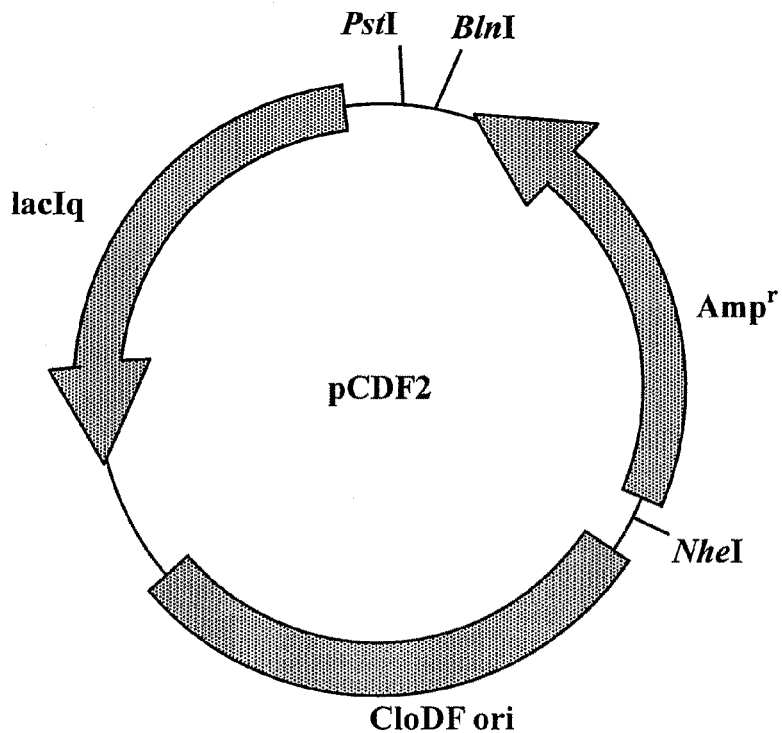
FIG. 2 shows a restriction map of plasmid pCDF2.

A DNA fragment containing T7 RNA polymerase gene was amplified by PCR using the pTrC99A-T7RNApol (FIG. 1) produced in Example 1 as a template, and then ligated into pCDF2 plasmid (FIG. 2).
(1) A PCR reaction was carried out using pTrc99A-T7RNApol (FIG. 1) as a template plasmid with the following reagent composition and under the following reaction conditions.
(Reagent Composition) (total reaction solution volume: 100 μL)

| Primer pTrcF (SEQ ID NO: 7) | 200 pM |
| Primer pTrcR (SEQ ID NO: 8) | 200 pM |
| Template plasmid | 100 ng |
| dNTPs | 0.2 mM |
| Taq DNA polymerase (Takara Ex Taq (trade name), Takara Bio) | 0.025 unit/μL |

Buffer provided for the enzyme (Reaction Conditions)
After initially heating for 2 minutes at 94° C., a temperature cycle consisting of 1 minute at 94° C., 30 seconds at 58° C. and 2 minutes and 40 seconds at 72° C. was repeated 25 times using a thermal cycler (Perkin-Elmer).
(2) The PCR products were purified by subjecting them to 1% agarose gel electrophoresis, staining the gel with ethidium bromide and cutting out bands of the target products from the stained gel.

(3) The purified PCR product was digested with restriction enzymes EcoT22I (Takara Bio) and BlnI (Takara Bio), and reacted with pCDF2 plasmid (FIG. 2) digested with restriction enzymes PstI (Takara Bio) and BlnI for 30 minutes at 4° C. using T4 ligase.

Figure 3:
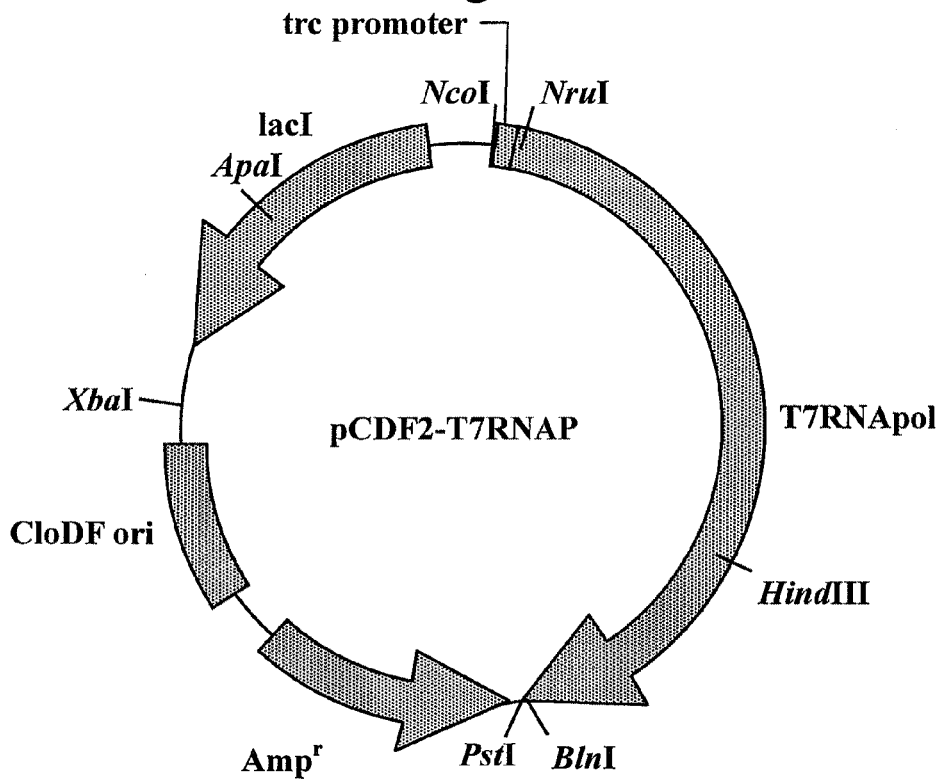
FIG. 3 shows a restriction map of plasmid pCDF2-T7RNAP that produces T7 RNA polymerase.

(4) The reaction solution of (3) was used to transform *E. coli* strain JM109 and selectively cultured on LBG/Crb agar medium (1% polypeptone, 0.5% yeast extract, 1% NaCl, 0.5% glucose, 1% agar and 50 µg/mL carbenicillin (pH 7.4)), and the plasmid retained by colonies that grew after culturing overnight at 37° C. was designated as pCDF2-T7RNAP. The restriction map of pCDF2-T7RNAP is shown in FIG. 3. Furthermore, the T7 RNA polymerase gene was confirmed to be free of unintended mutations by determining the base sequence using the method indicated in Example 6.

(5) A histidine hexamer was introduced based on pCDF2-T7RNAP (FIG. 3) using the method indicated below.

(5-1) One round of a PCR reaction was carried out using pCDF2-T7RNAP (FIG. 3) as a template plasmid with the following reagent composition and under the following reaction conditions. Furthermore, a combination of primer HisF (SEQ ID NO: 9) and primer pCDFR (SEQ ID NO: 10) or a combination of primer H is R (SEQ ID NO: 11) and primer pCDFF (SEQ ID NO: 12) was used for the synthetic primers.

(Reagent Composition) (total reaction solution volume: 100 µL)

| | |
|---|---|
| Synthetic DNA primers | 200 pM each |
| Template plasmid | 100 ng |
| dNTPs | 0.2 mM |
| DNA polymerase (PrimeSTAR HS DNA polymerase (trade name), Takara Bio) | 0.025 unit/µL |

Buffer provided for the enzyme (Reaction Conditions)
After initially heating for 30 seconds at 98° C., a temperature cycle consisting of 30 seconds at 98° C., 30 seconds at 55° C. and 3 minutes at 72° C. was repeated 30 times using a thermal cycler (Perkin-Elmer) followed by reacting for 7 minutes at 72° C.

(5-2) The PCR products were purified by subjecting the reaction solution to 1% agarose gel electrophoresis, staining the gel with ethidium bromide and cutting out bands of the target products from the stained gel.

(5-3) Two rounds of a PCR reaction were carried out using the resulting two types of PCR products as templates, and using the combination of primer pCDFR (SEQ ID NO: 10) and primer pCDFF (SEQ ID NO: 12) as synthetic DNA primers. The reagent composition and reaction conditions of the PCR reaction were the same as section (5-1) with the exception of the synthetic DNA primers, and the amplified products were electrophoresed, extracted and purified in the same manner as section (5-2).

(5-4) 0.2 mM of dNTPs, 0.025 unit/µL of DNA polymerase and the buffer provided for the enzyme were added to the pCDF2-T7RNAP plasmid (FIG. 3) and the product of the second round of PCR purified in section (5-3) and brought to a total reaction solution volume of 100 µL. A PCR reaction was carried out on this reaction solution by initially heating for 30 seconds at 95° C. followed by repeating 18 temperature cycles consisting of 30 seconds at 95° C., 1 minute at 55° C. and 8 minutes at 68° C., and finally allowing to react for 7 minutes at 68° C.

(5-5) Following completion of the PCR reaction, 10 units of restriction DpnI was added followed by digesting for 1 hour at 37° C. and then the PCR produce was transformed into *E. coli* strain JM109 in accordance with ordinary methods.

Figure 4:
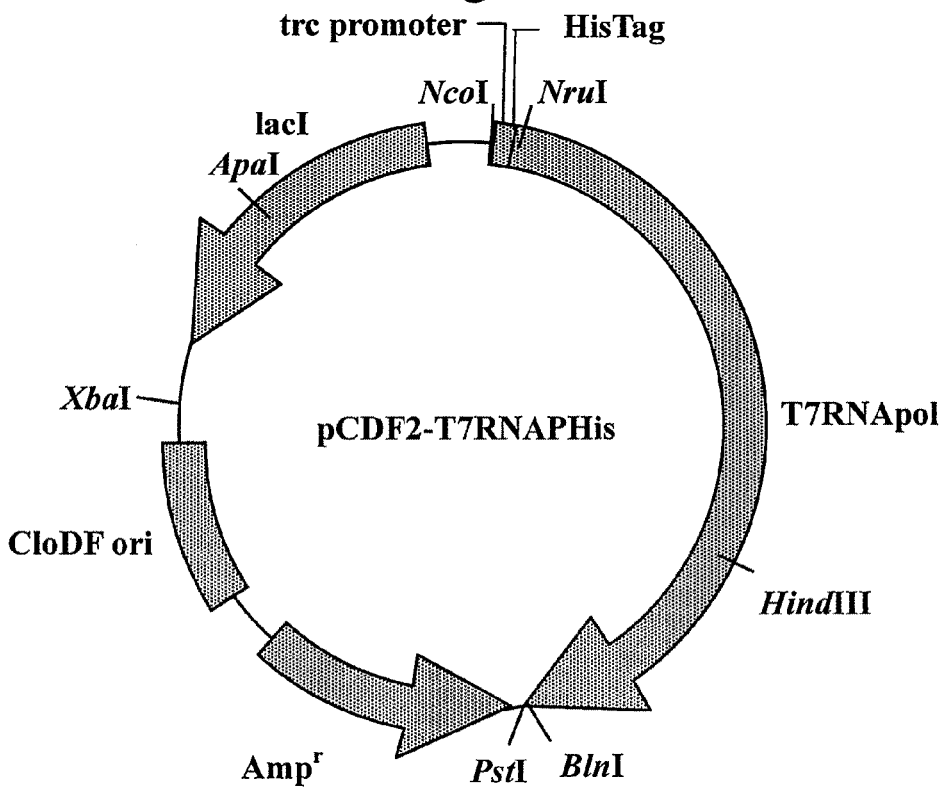
FIG. 4 shows a restriction map of plasmid pCDF2-T7RNAPHis that produces T7 RNA polymerase having a histidine hexamer fused to the N-terminal thereof.

(5-6) A solution of the transformed *E. coli* was applied to LBG/Crb agar medium (1% polypeptone, 0.5% yeast extract, 1% NaCl, 0.5% glucose, 1% agar and 50 µg/mL carbenicillin (pH 7.4)) and incubated overnight at 37° C. Plasmid was extracted from the formed colonies in accordance with ordinary methods to obtain plasmid pCDF2-T7RNAPHis. A restriction map of pCDF2-T7RNAPHis is shown in FIG. 4. Moreover, the plasmid was confirmed to be free of unintended mutations and confirmed to be inserted with histidine hexamer by base sequencing using the method indicated in Example 6. In addition, enzyme was extracted from the cultured bacterial cells and was confirmed to be capable of being affinity-purified by means of a nickel chelate resin. The gene sequence of the resulting T7 RNA polymerase fused with histidine hexamer is shown in SEQ ID NO: 13, while the amino acid sequence is shown in SEQ ID NO: 14.

Example 3

Production of Mutation Library (Part 1)

Mutations were introduced into T7 RNA polymerase gene of plasmid pCDF2-T7RNAPHis (FIG. 4) produced in Example 2 using the procedure described below.

(1) An error-prone PCR reaction was carried out by using plasmid pCDR2-T7RNAPHis (FIG. 4) as a template plasmid with the following reagent composition and under the following reaction conditions.

(Reagent Composition) (total reaction solution volume: 100 µL)

| | |
|---|---|
| MnCl$_2$ | 0.1 to 0.3 mM (as necessary) |
| Primer pTrcFs (SEQ ID NO: 15) | 200 pM |
| Primer pTrcRs (SEQ ID NO: 16) | 200 pM |
| Template plasmid | 100 ng |
| dATP | 0.2 mM |
| dGTP | 0.2 mM |
| dCTP | 1 mM |
| dTTP | 1 mM |
| MgCl$_2$ | 2 mM |
| Taq DNA polymerase (GoTaq (trade name) Promega) | 0.01 unit/µL |

Mg-free buffer provided for the enzyme (Reaction Conditions)
After initially heating for 2 minutes at 94° C., a temperature cycle consisting of 30 seconds at 94° C., 1 minute at 55° C. and 8 minutes at 72° C. was repeated 25 times using a thermal cycler (Perkin-Elmer).

(2) The PCR product was purified by subjecting it to 1% agarose gel electrophoresis, staining the gel with ethidium bromide and cutting out the band of the target product from the stained gel.

(3) After digesting the purified T7 RNA polymerase gene with restriction enzymes NcoI and PstI, it was reacted with plasmid pCDF2 (FIG. 2) digested with the same enzymes for 30 minutes at 4° C. using T4 ligase, and the DNA solution obtained following the reaction was used as a T7 RNA polymerase gene mutant library.

(4) A portion of the produced library was transformed into *E. coli* strain JM109 by a conventional method, the plasmid was purified therefrom, and the effect of error-prone PCR was confirmed by base sequencing using the method indicated in Example 6.

Example 4

Production of Screening Vector

A vector for confirming activity was produced using GFP to evaluate the activity of the mutation library produced in Example 3.

(1) GFP gene dsDNA was synthesized based on base sequence information (GenBank Accession Number AF183395). The synthesized GFP gene was designed to harbor T7 promoter and a base sequence of restriction enzyme SphI (Takara Bio) for cloning.

(2) After digesting the synthesized GFP gene with restriction enzyme SphI for 3 hours at 37° C., the PCR product was purified by subjecting it to 1.0% agarose gel electrophoresis, staining the gel with ethidium bromide and cutting out the target product band from the stained gel. This was then reacted for 30 minutes at 4° C. with pSTV28 vector (Takara Bio) digested and purified simultaneously thereto using T4 ligase.

(3) The reaction solution of (2) was transformed into *E. coli* strain JM109 and selectively cultured in LBG/Cm agar medium (1% polypeptone, 0.5% yeast extract, 1% NaCl, 0.5% glucose, 1% agar, 30 µg/mL chloramphenicol) to obtain colonies that grew after incubating overnight at 37° C.

Figure 5:
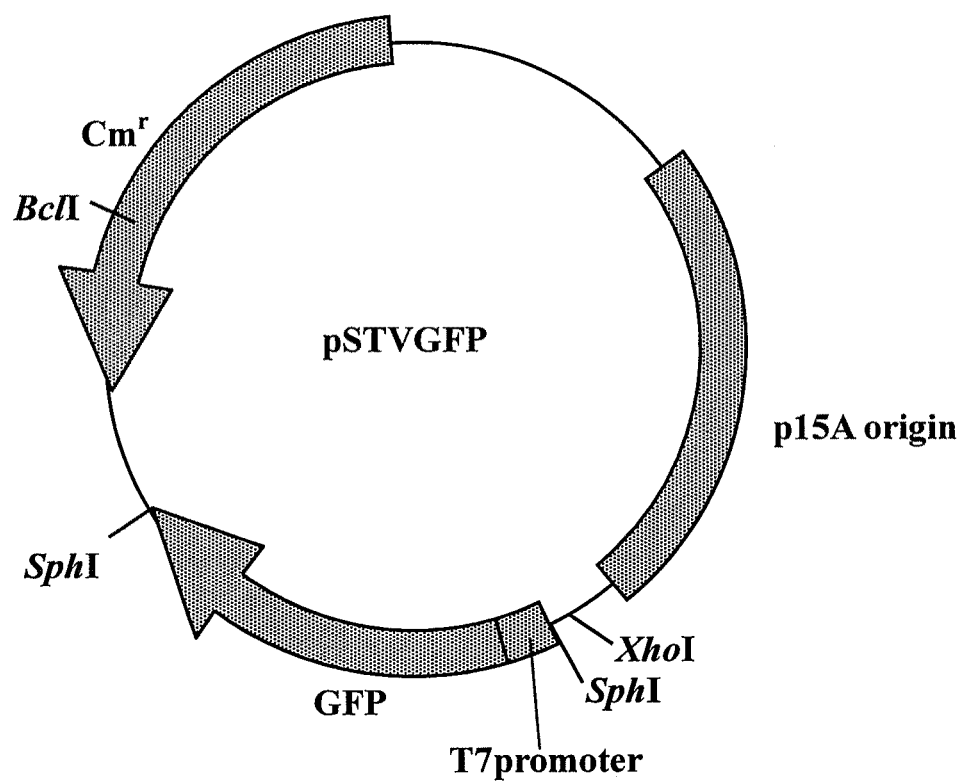
FIG. 5 shows a restriction map of pSTVGFP having a GFP gene for which expression is induced by a T7 promoter.

(4) After culturing the acquired colonies using LBG/Cm broth medium (1% polypeptone, 0.5% yeast extract, 1% NaCl, 0.5% glucose, 30 µg/mL chloramphenicol) overnight at 37° C., plasmid was recovered and this plasmid was designated as pSTVGFP, which retained GFP gene for which expression was induced by T7 promoter. A restriction map of pSTVGFP is shown in FIG. 5.

(5) The acquired pSTVGFP (FIG. 5) was transformed into *E. coli* strain JM109 together with the T7 RNA polymerase gene mutant library produced in Example 3. After culturing this bacterial broth in SOC medium for 1.5 hours, strains for which fluorescence was observed with an FACAria Cell Sorter (Nippon Becton Dickinson) were fractionated for individual clones, and those strains that grew at 37° C. in 2xYTG/Crb medium (1.6% Bacto tryptone, 0.5% Bacto yeast extract, 0.5% NaCl, 0.5% glucose, 50 µg/mL carbenicillin (pH 7.4)) were respectively designated as mutant candidates.

Example 5

Screening of High-Temperature T7 RNA Polymerase

Screening of mutant strains was carried out using a 96-well titer plate so enable efficient evaluation of mutants.

(1) 200 µL of LBG/Crb medium (1% polypeptone, 0.5% yeast extract, 1% NaCl, 0.5% glucose, 50 µg/mL carbenicillin (pH 7.4)) were added to 1 mL volume 96-deep well plate, and the plate was inoculated with GFP-positive colonies obtained in Example 4 followed by culturing overnight at 37° C. and 600 rpm.

(2) 1.0 mL of 2xYTG/Crb medium (1.6% Bacto tryptone, 1% Bacto yeast extract, 0.5% NaCl, 0.5% glucose, 50 µg/mL carbenicillin (pH 7.4)) was added to 2 mL volume 96-deep well plate and the plate was inoculated with 10 µL of the overnight culture broth of (1) followed by starting culturing at 37° C. and 750 rpm.

(3) After culturing for about 4 hours as described in (2) above, 10 µL of 50 mM IPTG (isopropyl-(3-thiogalactopyranoside) solution were added followed by lowering the temperature to 30° C. and shake-culturing for 3 hours. Following completion of culturing, the culture broth was centrifuged at 4° C. for 15 minutes at 3000 rpm followed by recovery of the bacterial cells and storing the bacterial cells by freezing overnight at −30° C.

(4) 100 µL of cell lysis solution (composition: 20 mM Tris-HCl buffer (pH 8.0), 0.2% Triton X-100, 0.02% sodium deoxycholate, 0.03% lysozyme (Taiyo Kagaku), 0.25 units of Benzonase (Novagen)) were added to the frozen cells followed by shaking for 1 hour at 30° C. and 500 rpm and centrifuging at 4° C. for 30 minutes at 3000 rpm to recover the supernatant.

(5) The entire volume of the supernatant obtained in (4) was applied to a 96-well filter plate packed with nickel chelate resin (His-Bind (trade name), Novagen), and after washing four times with 200 µL of buffer A (20 mM Tris-HCl buffer containing 20 mM imidazole and 500 mM sodium chloride (pH 8.0)), the resin was subjected to elution with 50 µL of buffer B (20 mM Tris-HCl buffer containing 150 mM imidazole and 500 mM sodium chloride (pH 8.0)).

(6) The eluted fractions were measured for protein concentration and transcription activity in the same manner as the procedure of Example 7 and specific activity was determined in terms of the amount of transcription product per amount of protein. Transcription activity measurement conditions consisted of setting the reaction temperature to 46° C., the reaction time to 60 minutes and the amount of T7 RNA polymerase to 0.5 µL, and RNA was quantified using a Quant-IT RNA Assay Kit (trade name) (Invitrogen). As a result, 60 strains that demonstrated specific activity roughly twice as high as that of the wild type were screened from among about 4000 mutant strains.

Example 6

Sequencing Method

The mutant candidates selected in Example 5 were cultured overnight at 37° C. in LBG/Crb broth medium (1% polypeptone, 0.5% yeast extract, 1% NaCl, 0.5% glucose, 50 µg/mL carbenicillin (pH 7.4)) followed by extracting plasmids in accordance with ordinary methods. Base sequencing of T7 RNA polymerase gene contained in the extracted plasmids was carried out using the method described below.

(1) Using the Big Dye Terminator V.3.1 Cycle Sequencing Kit (trade name) (Applied Biosystems), 2.0 µl of buffer provided with the kit, 4.0 µL of pre-mix, 3.2 µmol of synthetic DNA primer and 500 ng of template plasmid were adjusted to a volume of 20 µL with sterilized water, followed by initially heating for 1 minute at 96° C. and the repeating 25 cycles consisting of 10 seconds at 96° C., 5 seconds at 50° C. and 4 minutes at 60° C. using a thermal cycler (Perkin-Elmer).

(2) The sample for base sequencing prepared in (1) was purified according to the following method using a Centri-Sep Spin Column (trade name) (ABI).

(2-1) 800 µL of sterilized water were added to the Centri-Sep Spin Column to adequately hydrate the dried gel with a vortex.

(2-2) After confirming to be free of air bubbles, the column was allowed to stand for at least 2 hours at room temperature.

(2-3) The upper cap and lower stopper were removed in that order to allow the sterilized water in the column to spontaneously drain until it reached the surface of the gel followed by centrifuging for 2 minutes at 730×g.

(2-4) The sample for base sequencing was applied to the center of the spin column prepared according to (2-1) to (2-3), and the sample was recovered from the tube by centrifuging for 2 minutes at 730×g.

(2-5) The recovered sample was vacuum-dried followed by dissolving in formamide.

(3) The sample for base sequencing prepared in (2) was treated for 2 minutes at 95° C., and after rapidly cooling on ice, the base sequencing was carried out using an ABI PRISM 310-DNA Analyzer (trade name) (Applied Biosystems). Synthetic DNA primers used for the base sequencing were selected as necessary from among primer pTrcFs (SEQ ID NO: 15), primer pTrcRs (SEQ ID NO: 16), primer T7F0 (SEQ ID NO: 17), primer T7F1 (SEQ ID NO: 18), primer T7F2 (SEQ ID NO: 19), primer T7F3 (SEQ ID NO: 20), primer T7F4 (SEQ ID NO: 21), primer T7F5 (SEQ ID NO: 22), primer T7F6 (SEQ ID NO: 23), primer T7R0 (SEQ ID NO: 24), primer T7R1 (SEQ ID NO: 25), primer T7R2 (SEQ ID NO: 26), primer T7R3 (SEQ ID NO: 27), primer T7R4 (SEQ ID NO: 28), primer T7R5 (SEQ ID NO: 29) and primer T7R6 (SEQ ID NO: 30).

(4) The sequenced base sequence was analyzed using GENETYX Ver. 8.0 (trade name) (Genetyx).

As a result of analysis, base sequence substitutions were found in 19 strains. Among these, mutations resulting in amino acid changes were contained in 10 of the strains. In one of these strains, an AAG codon was substituted with a GAG codon as a result of adenine at position 535 having been substituted with guanine in wild type T7 RNA polymerase (SEQ ID NO: 5), and lysine at position 179 was determined to have mutated to glutamate in the amino acid sequence of this polymerase (SEQ ID NO: 6). The T7 RNA polymerase harboring this mutation was designated as mutant K179E, its gene sequence is shown in SEQ ID NO: 31, while its amino acid sequence is shown in SEQ ID NO: 32. Moreover, in the remaining nine strains, a CAA codon was substituted with a CTA codon as a result of adenine at position 2357 being substituted with thymine in the base sequence of wild-type T7 RNA polymerase (SEQ ID NO: 5), and glutamine at position 786 of the amino acid sequence of this polymerase (SEQ ID NO: 6) was determined to have mutated to leucine. The T7 RNA polymerase harboring this mutation was designated as mutant Q786L, its gene sequence is shown in SEQ ID NO: 33, and its amino acid sequence is shown in SEQ ID NO: 34.

Example 7

Preparation and Activity Measurement of T7 RNA Polymerase

T7 RNA polymerase was prepared according to the procedure described below.

(1) 3 mL of LBG/Crb broth medium (1% polypeptone, 0.5% yeast extract, 1% NaCl, 0.5% glucose, 50 µg/mL carbenicillin (pH 7.4)) was inoculated with a glycerol stock of the transformant obtained in Example 5 followed by shake-culturing overnight at 37° C. in an 18 mL test tube.

(2) 100 mL of 2xYTG/Crb medium (1.6% Bacto tryptone, 1% Bacto yeast extract, 0.5% NaCl, 0.5% glucose, 50 µg/mL carbenicillin (pH 7.4)) were inoculated with 1.0 mL of the pre-culture broth of (1) followed by shake-culturing at 37° C. and 150 rpm (rotary type, Tietech) in a 500 mL volumetric fluted Erlenmeyer flask.

(3) After about 3 to 4 hours of the culturing of (2) (to an $OD_{600\ nm}$ value of about 1.0), 100 µL of 500 mM IPTG (isopropyl-(3-thiogalactopyranoside) were added followed by lowering the temperature to 30° C. and additionally shake-culturing for 3 hours.

(4) Following completion of culturing, the culture broth was centrifuged for 15 minutes at 4° C. and 4000 rpm to recover the bacterial cells. The recovered cells were stored at −30° C. in the case of not lysing immediately.

(5) The recovered bacterial cells were washed once with 20 mL of 20 mM potassium phosphate buffer solution (pH 7.0), and then re-suspended in 20 mL of buffer solution having the same composition followed by lysing. Cell lysis was carried out by treating for about 5 minutes at 5° C. and an output of about 150 W using an ultrasonic generator (Insonator 201M (trade name), Kubota).

(6) The resulting cell lysate was centrifuged for 10 minutes at 4° C. and 12000 rpm, and using the recovered supernatant as an enzyme extract, sodium chloride and imidazole were added to the extract at 500 mM and 20 mM, respectively, followed by application to affinity purification using a nickel chelate resin.

(7) Enzyme purification was carried out with the following method by affinity purification with a histidine hexamer tag added to T7 RNA polymerase.

(7-1) 2 mL of a slurry of nickel chelate resin (His-Bind (trade name), Novagen) was packed into an empty column provided therewith and washed with 3 mL of sterilized water.

(7-2) Nickel was bound to a chelate resin by adding 5 mL of 50 mM aqueous nickel sulfate solution to the washed nickel chelate resin followed by further washing with 3 mL of buffer A (20 mM Tris-HCl buffer (pH 8.0), 500 mM sodium chloride, 20 mM imidazole). After adding the aforementioned enzyme extract thereto and washing with 6 mL of buffer A, the resin was eluted with 1 mL of buffer B (20 mM Tris-HCl buffer (pH 8.0), 500 mM sodium chloride, 150 mM imidazole) followed by recovery of the active fraction.

(7-3) The recovered fraction was replaced with 20 mM potassium phosphate buffer solution (pH 7.0) containing 5 mM dithiothreitol and 0.1 mM EDTA by using a desalting column (PD-10 (trade name), GE Healthcare Biosciences) followed by the addition of an equal volume of glycerol. The concentration of purified T7 RNA polymerase was determined with a protein assay kit (BioRad) using bovine serum albumin as a control protein. In addition, enzyme purity was analyzed by SDS-PAGE at a concentration of 7.5% and was confirmed to be nearly homogeneous.

(8) Activity was measured using a method that measures the amount of RNA formed in an in vitro transcription reaction. Furthermore, although DNA having a T7 promoter sequence that is specifically recognized by T7 RNA polymerase is used for the template DNA, in this case, an approximately 1.5 kbp DNA fragment was used that was amplified by PCR using a plasmid containing a T7 promoter sequence as a template. In addition, the length of DNA downstream from the T7 promoter sequence is about 1.0 kbps, and the RNA transcribed is about 1.0 kb.

(8-1) The reaction solution from which T7 RNA polymerase had been removed (40 mM Tris-HCl buffer (pH 8.0), 20 mM $MgCl_2$, 5 mM dithiothreitol, 20 ng template DNA, 0.4 U RNase inhibitor, 0.4 mM each NTPs (ATP, CTP, GTP, UTP)) was placed in a 0.2 mL PCR tube followed by addition of the purified T7 RNA polymerase while cooled to 0° C. and bringing to a total of 10 µL.

(8-2) The previously prepared PCR tube was placed on a heat block (Mastercycler ep Gradient (trade name), Eppendorf) pre-warmed to the reaction temperature followed by carrying out a transcription reaction. The reaction was stopped by heating for 2 minutes at 80° C.

(8-3) The amount of RNA formed was analyzed by a method consisting of electrophoresing with 1% agarose gel and staining the gel with ethidium bromide, and a method consisting of fluorescent staining using the commercially available RNA assay kit, Quant-IT RNA Assay Kit (trade name) (Invitrogen)

Example 8

Production of Double Mutant (K179E+Q786L)

A double mutant was produced that harbored two K179E and Q786L mutations based on mutant K179E and mutant Q786.

(1) Plasmids were respectively produced from mutant K179E and mutant Q786L using a miniprep method.

(2) A PCR reaction was carried out using the following reagent composition and under the following conditions using the plasmid prepared from mutant K179E as a template.

(Reagent Composition) (total reaction solution volume: 100 μL)

| | |
|---|---|
| Primer T7R2 (SEQ ID NO: 26) | 200 pM |
| Primer pTrcFs (SEQ ID NO: 15) | 200 pM |
| Template plasmid | 100 ng |
| dNTPs | 0.2 mM |
| TaqDNA polymerase (Takara Ex Taq (trade name), Takara Bio) | 0.025 unit/μL |

Buffer provided for the enzyme (Reaction Conditions)

After heating for 2 minutes at 94° C., a temperature cycle consisting of 1 minute at 94° C., 30 seconds at 58° C. and 2 minutes 40 seconds at 72° C. was repeated 25 times using a thermal cycler (Perkin-Elmer).

(3) The PCR product was purified by subjecting the reaction solution to 1% agarose gel electrophoresis, staining the gel with ethidium bromide and cutting out the band of the target product from the stained gel.

(4) A PCR reaction and purification were carried out under the same conditions as (1) and (2) with the exception of using the plasmid prepared from mutant Q786L for the template, and using the combination of primer T7F2 (SEQ ID NO: 19) and primer pTrcRs (SEQ ID NO: 16) as synthetic primers.

(5) A PCR reaction was further carried out using the two types of purified PCR products obtained in (3) and (4) as templates to produce a double mutant gene. Furthermore, the reagent composition, reaction conditions and purification procedure used in the PCR reaction were the same as in (1) and (2) with the exception of using the combination of primer pTrcFs (SEQ ID NO: 15) and primer pTrcRs (SEQ ID NO: 16) as synthetic DNA primers.

(6) The double mutant gene obtained in (5) was digested with restriction enzymes NcoI and PstI (Takara Bio) followed by reacting for 30 minutes at 4° C. with pCDF2 vector digested with the same enzymes using T4 ligase.

(7) The reaction solution of (6) was transformed into *E. coli* strain JM109 followed by selective culturing on LBG/Crb agar medium (1% polypeptone, 0.5% yeast extract, 1% NaCl, 0.5% glucose, 1% agar, 50 μg/mL carbenicillin (pH 7.4)) and the colonies that grew after culturing overnight at 37° C. were obtained as double mutant. Moreover, the double mutant was confirmed to have been introduced with mutations by the base sequencing method indicated in Example 6, and was designated as double mutant (K179E+Q786L). The gene sequence of this double mutant is shown in SEQ ID NO. 35, while the amino acid sequence is shown in SEQ ID NO.: 36.

Example 9

Evaluation of Thermal Stability of T7 RNA Polymerase Mutant (Part 1)

Thermal stability of the T7 RNA polymerase mutant was measured in the manner described below.

(1) A mutant in which the amino acid at position 179 was substituted from lysine to glutamate (K179E), a mutant in which the amino acid at position 786 was substituted from glutamine to leucine (Q786L) and a double mutant that combined both mutations (K179E+Q786L), which had higher activity at high temperatures than the wild type based on the results of base sequencing (Example 6) of the mutants screened in Example 5, were used to prepare purified enzymes according to the method described in Example 7. Furthermore, the protein concentrations and transcription activities of the purified enzymes were measured in compliance with the method indicated in Example 7.

(2) Each type of T7 RNA polymerase prepared in Example 7 was adjusted to 50 μg/mL using a diluent (40 mM Tris-HCl buffer (pH 8.0), 20 mM magnesium chloride, 5 mM dithiothreitol, 70 mM KCl, 0.1 mg/mL bovine serum albumin).

(3) 25 μl, aliquots of the diluted T7 RNA polymerase were dispensed into 0.2 mL PCR tubes and heated at 47° C. for 5 minutes, 10 minutes and 20 minutes, respectively.

(4) After recovering the supernatant by centrifuging following completion of heat treatment, a transcription reaction was carried out for 30 minutes at 43° C. followed by determination of residual activity.

(5) The amount of RNA that formed was analyzed by 1% agarose gel electrophoresis.

Figure 6:
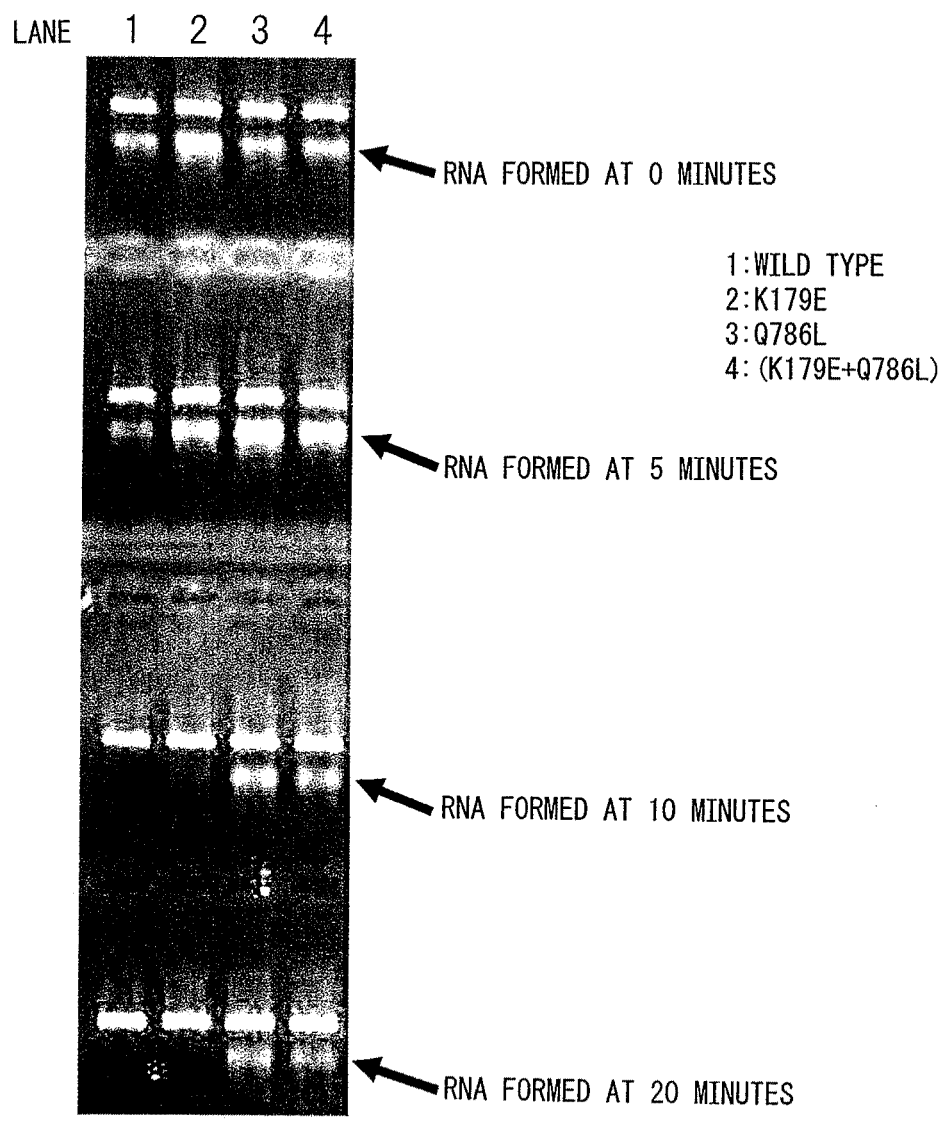
FIG. 6 shows the results (electrophoresis) of comparing thermal stability against heating at 47° C. between a wild type of T7 RNA polymerase produced and its mutants K179E, Q786L and a double mutant thereof (K179E+Q786L), respectively. Furthermore, lane 1, lane 2, lane 3 and lane 4 in the drawing indicate results when using T7 RNA polymerase of the wild type, mutant K179E, mutant Q786L and the double mutant (K179E+Q786L), respectively.

The results are shown in FIG. 6. On the basis of FIG. 6, mutants Q786L and (K179E+Q786L) were observed to demonstrate well-defined RNA bands at 47° C. at which the wild type demonstrates hardly any activity. On the basis of this finding, it was determined that T7 RNA polymerase at least introduced with mutant Q786L has superior thermal stability than the wild type.

Example 10

Evaluation of T7 RNA Polymerase Mutant Activity (Part 1)

The activity of the T7 RNA polymerase mutant at various reaction temperatures was measured in the manner described below.

(1) A mutant in which the amino acid at position 179 was substituted from lysine to glutamate (K179E), a mutant in which the amino acid at position 786 was substituted from glutamine to leucine (Q786L) and a double mutant that combined both mutations (K179E+Q786L), which had higher activity at high temperatures than the wild type based on the results of base sequencing (Example 6) of the mutants screened in Example 5, were used to prepare purified enzymes according to the method described in Example 7. Furthermore, the protein concentrations and transcription activities of the purified enzymes were measured in compliance with the method indicated in Example 7.

(2) The activity of T7 RNA polymerase was measured by using a value of 10 μg/mL for the amount of T7 RNA polymerase and reacting for 10 minutes over a temperature range of 43 to 50° C.

(3) The amount of RNA that formed was determined using the Quant-IT RNA Assay Kit (trade name) (Invitrogen).

Figure 7:
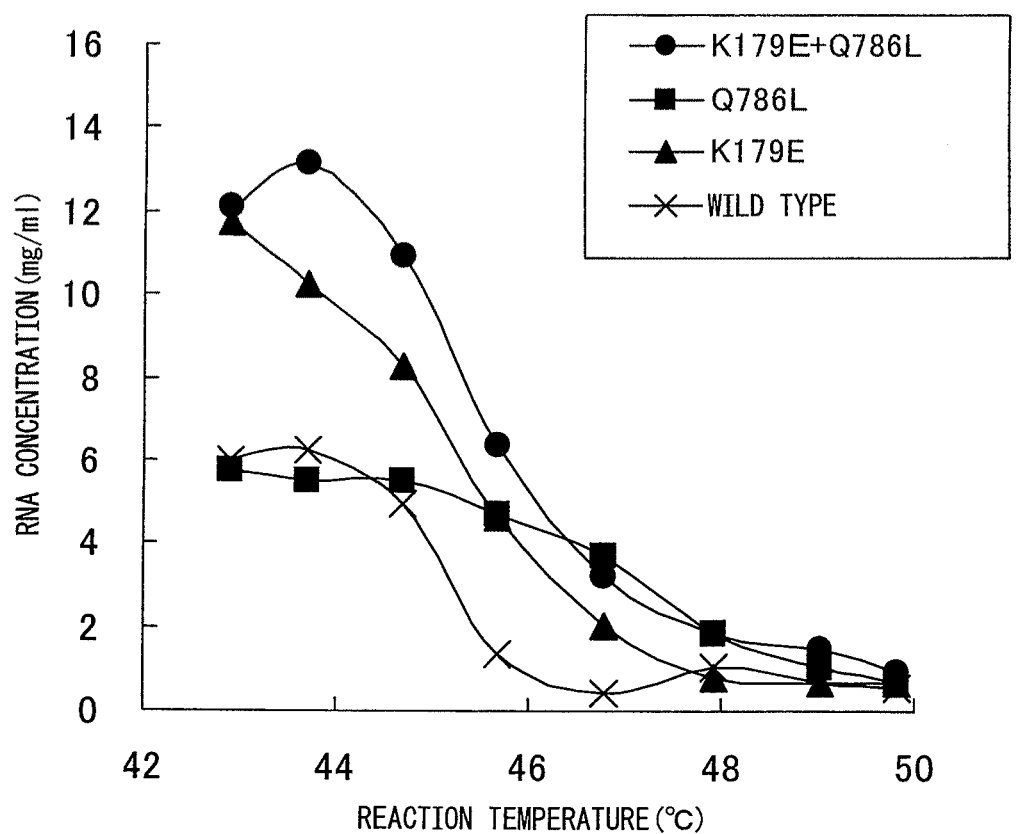
FIG. 7 shows the results of comparing RNA production amounts at 43 to 50° C. between a wild type of T7 RNA polymerase produced and mutant K179E, mutant Q786L and double mutant (K179E+Q786L), respectively.

The measured RNA concentrations are shown in FIG. 7. Mutant K179E was found to demonstrate specific activity higher than that of the wild type over a range of 42.9 to 46.8° C., and on the basis thereof, T7 RNA polymerase introduced with at least mutant K179E was determined to have improved specific activity as compared with the wild type. Next, although mutant Q786L demonstrated higher specific activity than the wild type over a range of 44.7 to 47.9° C., this is thought to be attributable to improved thermal stability based on the results of Example 9. In addition, the double mutant (K179E+Q786L) demonstrated higher specific activity than the wild type at a temperature range of 42.9° C. to 47.9° C. On the basis thereof, T7 RNA polymerase introduced with at least mutant K179E and mutant Q786L was determined to have improved thermal stability and specific activity as compared with the wild type.

Example 11

Preparation of T7 RNA Polymerase Mutant Gene (Part 1)

A gene encoding T7 RNA polymerase, in which lysine at position 179 of the amino acid sequence of wild-type T7 RNA polymerase (SEQ ID NO: 6) was substituted with another amino acid, was prepared according to the procedure described below.
(1) The first round of a PCR reaction was carried out using pCDF2-T7RNAPHis (FIG. 4) for the template plasmid, using the reagent composition indicated below and under the reaction conditions indicated below. Furthermore, a combination of primer pCDFF (SEQ ID NO: 12) and primer 179MIXR (SEQ ID NO: 39) was used as synthetic DNA primers for amplifying the 5'-terminal of T7 polymerase gene, while a combination of primer 179MIXF (SEQ ID NO: 37) and primer pCDFR2 (SEQ ID NO: 38) was used as synthetic primers for amplifying the 3'-terminal.
(Reagent Composition) (total reaction solution volume: 100 μL)

| | |
|---|---|
| Synthetic DNA primers | 200 pM each |
| Template plasmid | 100 ng |
| dNTPs | 0.2 mM |
| DNA polymerase (PrimeSTAR HS DNA polymerase (trade name), Takara Bio) | 0.025 unit/μL |

Buffer provided for the enzyme (Reaction Conditions)
After initially heating for 30 seconds at 98° C., a temperature cycle consisting of 30 seconds at 98° C., 30 seconds at 55° C. and 1 minute 30 seconds at 72° C. was repeated 30 times using a thermal cycler (Perkin-Elmer), followed by reacting for 7 minutes at 72° C.
(2) The PCR products prepared in (1) were purified by subjecting them to 1% agarose gel electrophoresis, staining the gel with ethidium bromide and cutting out bands of the target products from the stained gel.
(3) The second round of the PCR reaction was carried out using the two types of PCR products (5'-terminal and 3'-terminal) obtained above as templates, and using primer pCDFF (SEQ ID NO: 12) and primer pCDFR2 (SEQ ID NO: 38) as synthetic DNA primers. The reagent composition and reaction conditions in this PCR reaction were the same as (1) with the exception of the synthetic DNA primers and templates, and the amplified products were extracted and purified following electrophoresis in agarose gel in the same manner as (2).
(4) After digesting the second round PCR products purified in (3) with restriction enzymes NruI and SacI, they were reacted with plasmid pCDF2-T7RNAPHis (FIG. 4) digested with the same enzymes for 30 minutes at 4° C. using T4 ligase, and the DNA solutions obtained following the reaction were used as a T7 RNA polymerase gene mutant libraries.
(5) The libraries produced in (4) were transformed into *E. coli* strain JM109, and 90 colonies that grew at 37° C. in LBG/Crb medium (1.0% Bacto tryptone, 0.5% Bacto yeast extract, 0.5% NaCl, 0.5% glucose, 50 μg/mL carbenicillin (pH 7.4)) were selected from each library.
(6) After extracting plasmids from the selected bacterial strains using ordinary methods, base sequence mutations were confirmed by carrying out base sequencing in the same manner as the procedure of Example 6 with the exception of using pCDFF (SEQ ID NO: 12) for the synthetic DNA primer for base sequencing.

Example 12

Preparation of T7 RNA Polymerase Mutant Gene (Part 2)

A gene encoding T7 RNA polymerase, in which glutamine at position 786 of the amino acid sequence of wild-type T7 RNA polymerase (SEQ ID NO: 6) was substituted with another amino acid, was prepared according to the procedure described below.
(1) The first round of a PCR reaction was carried out using pCDF2-T7RNAPHis (FIG. 4) as the template plasmid, using the reagent composition indicated below and under the reaction conditions indicated below. Furthermore, a combination of primer pCDFF4 (SEQ ID NO: 42) and primer 786MIXR (SEQ ID NO: 41) was used as synthetic DNA primers for amplifying the 5'-terminal of T7 polymerase gene, while a combination of primer 786MIXF (SEQ ID NO: 40) and primer pTrcRS (SEQ ID NO: 16) was used as synthetic primers for amplifying the 3'-terminal.
(Reagent Composition) (total reaction solution volume: 100 μL)

| | |
|---|---|
| Synthetic DNA primers | 200 pM each |
| Template plasmid | 100 ng |
| dNTPs | 0.2 mM |
| DNA polymerase (PrimeSTAR HS DNA polymerase (trade name), Takara Bio) | 0.025 unit/μL |

Buffer provided for the enzyme (Reaction Conditions)
After initially heating for 30 seconds at 98° C., a temperature cycle consisting of 30 seconds at 98° C., 30 seconds at 55° C. and 1 minute 30 seconds at 72° C. was repeated 30 times using a thermal cycler (Perkin-Elmer), followed by reacting for 7 minutes at 72° C.
(2) The PCR products prepared in (1) were purified by subjecting them to 1% agarose gel electrophoresis, staining the gel with ethidium bromide and cutting out bands of the target products from the stained gel.
(3) The second round of the PCR reaction was carried out using the two types of PCR products (5'-terminal and 3'-terminal) obtained above as templates, and using primer pCDFF4 (SEQ ID NO: 42) and primer pTrcRS (SEQ ID NO: 16) as synthetic DNA primers. The reagent composition and reaction conditions in this PCR reaction were the same as (1) with the exception of the synthetic DNA primers and templates, and the amplified products were extracted and purified following electrophoresis in agarose gel in the same manner as (2).
(4) After digesting the second round PCR products purified in (3) with restriction enzyme HindIII and KpnI, they were reacted with plasmid pCDF2-T7RNAPHis (FIG. 4) digested with the same enzymes for 30 minutes at 4° C. using T4 ligase, and the DNA solutions obtained following the reaction were used as a T7 RNA polymerase gene mutant (position 179) libraries.
(5) The libraries produced in (4) were transformed into *E. coli* strain JM109, and 90 colonies that grew at 37° C. in LBG/Crb medium (1.0% Bacto tryptone, 0.5% Bacto yeast extract, 0.5% NaCl, 0.5% glucose, 50 μg/mL carbenicillin (pH 7.4)) were selected from each library.
(6) After extracting plasmids from the selected bacterial strains using ordinary methods, base sequence mutations were confirmed by carrying out the base sequencing in the same manner as the procedure of Example 6 with the exception of using pCDFF4 (SEQ ID NO: 42) for the synthetic DNA primer for base sequencing.

Example 13

Evaluation of T7 RNA Polymerase Mutant Activity (Part 2)

Figure 8:
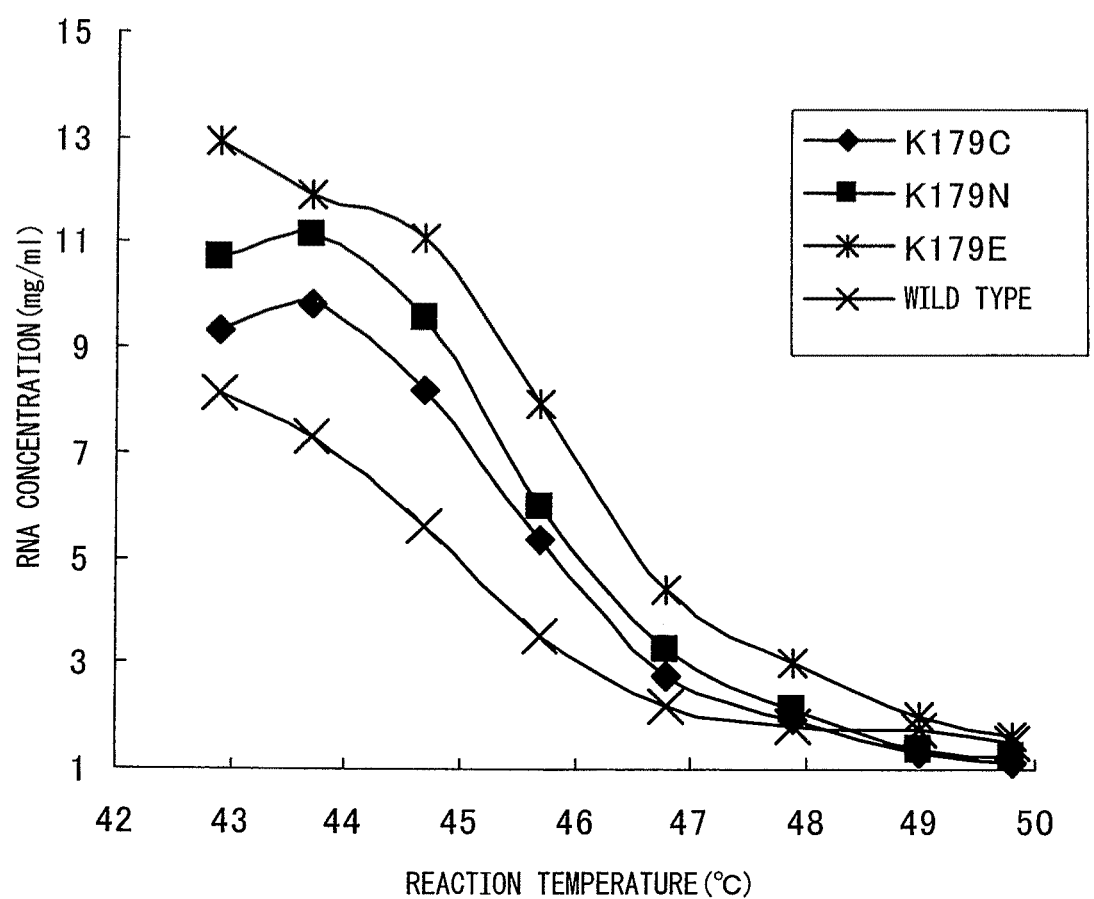
FIG. 8 shows the results of comparing RNA production amounts at 43 to 50° C. between a wild type of T7 RNA polymerase produced and mutants K179E, K179C and K179N, respectively.
Figure 9:
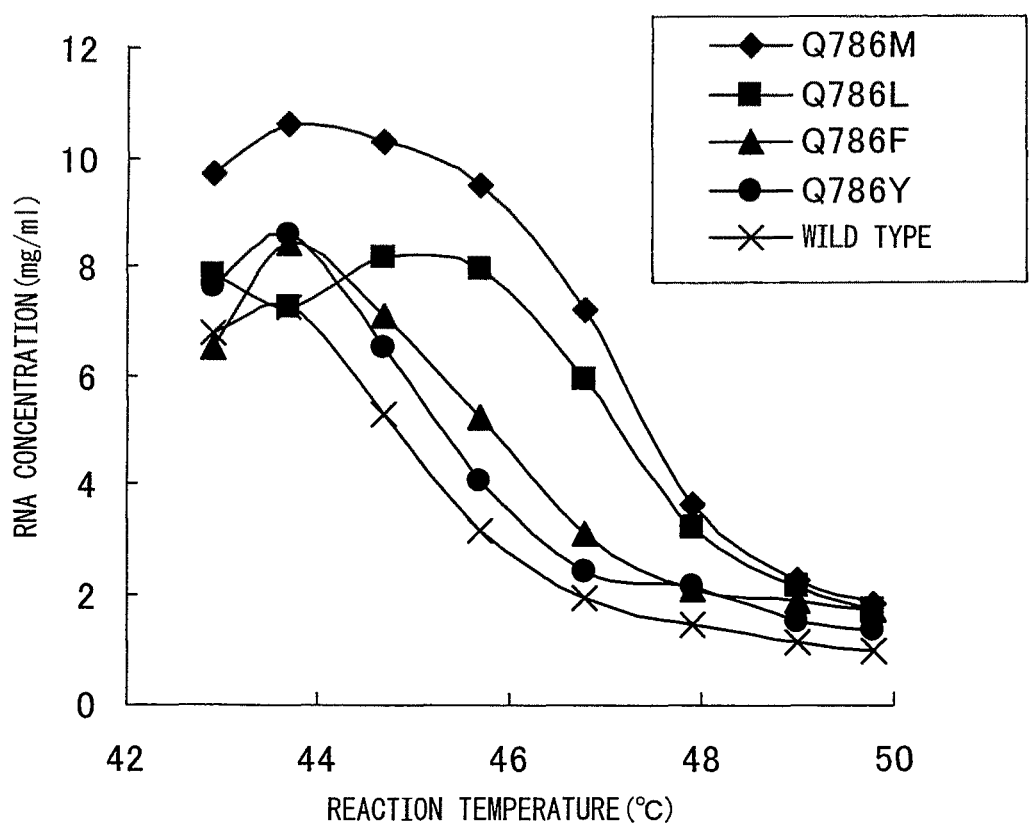
FIG. 9 shows the results of comparing RNA production amounts at 43 to 50° C. between a wild type of T7 RNA polymerase produced and mutants Q786L, Q786M, Q786F and Q786Y, respectively.

Preparation of T7 RNA polymerase and measurement of transcription activity were carried out according to the method of Example 7 based on the T7 RNA polymerase mutants prepared in Examples 11 and 12. The results are shown in FIG. 8 (T7 RNA polymerase in which lysine at position 179 is substituted with another amino acid) and FIG. 9 (T7 RNA polymerase in which glutamine at position 786 is substituted with another amino acid).
In the case of having substituted lysine at position 179 with another amino acid, in addition to the glutamate substitution (K179E) obtained in screening, mutants in which cysteine was substituted (K179C) and asparagine was substituted (K179N) also demonstrated improved thermal stability and/or specific activity as compared with the wild type, and the mutant substituted with glutamate (K179E) in particular demonstrated considerable improvement of heat resistance and specific activity as compared with the wild type (FIG. 8).
On the other hand, in the case of having substituted glutamine at position 786 with another amino acid, in addition to the leucine substitution (Q786L) obtained in screening, mutants substituted with methionine (Q786M), phenylalanine (Q786F) and tyrosine (Q786Y) also demonstrated improved heat resistance and/or specific activity as compared with the wild type, and the mutant substituted with methionine (Q786M) in particular demonstrated considerable improvement of heat resistance and specific activity as compared with the wild type (FIG. 9).

Example 14

Evaluation of Thermal Stability of T7 RNA Polymerase Mutants (Part 2)

Thermal stability of the T7 RNA polymerase mutants prepared in Example 13 was measured according to the following method.
(1) The T7 RNA polymerase mutants prepared in Example 13 (Q786M, Q786L, Q786F, Q786Y, K179E, K179C and K179N) and wild-type T7 RNA polymerase were prepared at 100 μg/mL using a buffer having the composition indicated below, and after dispensing 25 μl, aliquots thereof into 0.2 mL PCR tubes, were heat-treated for 1, 2, 5, 10, 20 and 30 minutes at 47° C.
(Buffer Composition)

| Tris-HCl buffer (pH 8.0) | 40 mM |
|---|---|
| MgCl₂ | 20 mM |
| Dithiothreitol | 5 mM |
| KCl | 70 mM |
| Bovine serum albumin | 0.01 mg/mL |

Figure 10:
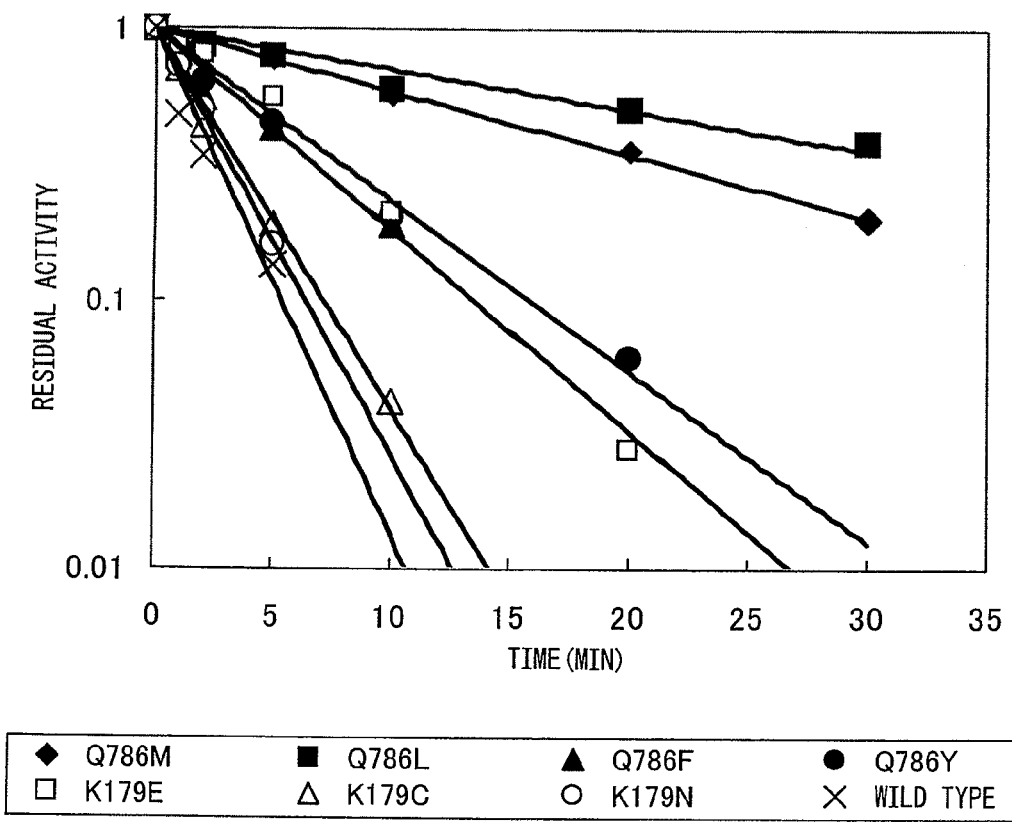
FIG. 10 shows the results of comparing thermal stability against heating at 47° C. between wild-type T7 RNA polymerase and polymerase mutants Q786L, Q786M, Q786F, Q786Y, K179E, K179C and K179N, respectively.

(2) Activities were measured by carrying out transcription reactions for 30 minutes at 43° C. using the heat-treated solutions, and the value obtained by dividing the activity for each treatment time by the activity prior to heating was defined as residual activity.
A graph of residual activity is shown in FIG. 10. In addition, the results of determining the half-lives of each type of T7 RNA polymerase mutant and the wild type from the slope of the graph of FIG. 10 are shown in Table 1. According to Table 1, the half-lives of each of the T7 RNA polymerase mutants were found to be longer than that of the wild type, thereby demonstrating superior thermal stability at 48° C. In addition, the thermal stabilities of T7 RNA polymerase mutants Q786L and Q786M were determined to be particularly high.

TABLE 1

| T7 RNA Polymerase | Half-life (min) |
|---|---|
| Mutant Q786M | 12.9 |
| Mutant Q786L | 19.9 |
| Mutant Q786F | 4.0 |
| Mutant Q786Y | 4.7 |
| Mutant K179E | 4.0 |
| Mutant K179C | 2.1 |
| Mutant K179N | 1.9 |
| Wild type | 1.6 |

Example 15

Production of Mutation Library (Part 2)

Mutations were introduced according to the following procedure using plasmid vector pCDF2-T7RNAPHis (K179E+Q786L) containing the mutant (K179E+Q786L) gene sequence produced in Example 8 (SEQ ID NO: 35) and a histidine hexamer sequence on the 5'-terminal of that sequence.
(1) An error-prone PCR reaction was carried out by using plasmid pCDF2-T7RNAPHis (K179E+Q786L) as a template plasmid with the following reagent composition and under the following reaction conditions.
(Reagent Composition) (total reaction solution volume: 100 μL)

| MnCl₂ | 0.1 to 0.3 mM (as necessary) |
|---|---|
| Primer pTrcFs (SEQ ID NO: 15) | 200 pM |
| Primer pTrcRs (SEQ ID NO: 16) | 200 pM |
| Template plasmid | 100 ng |
| dATP | 0.2 mM |

| -continued | |
|---|---|
| dGTP | 0.2 mM |
| dCTP | 1 mM |
| dTTP | 1 mM |
| MgCl$_2$ | 2 mM |
| Taq DNA polymerase (GoTaq (trade name) Promega) | 0.01 unit/μL |

Mg-free buffer provided for the enzyme (Reaction Conditions)

After initially heating for 2 minutes at 94° C., a temperature cycle consisting of 30 seconds at 94° C., 1 minute at 55° C. and 8 minutes at 72° C. was repeated 25 times using a thermal cycler (Perkin-Elmer).

(2) The PCR product was purified by subjecting it to 1% agarose gel electrophoresis, staining the gel with ethidium bromide and cutting out the band of the target product from the stained gel.

(3) After digesting the purified T7 RNA polymerase gene with restriction enzymes NcoI and PstI, it was reacted with plasmid pCDF2-T7RNAPHis (FIG. 4) digested with the same enzymes for 30 minutes at 4° C. using T4 ligase, and the DNA solution obtained following the reaction was used as a T7 RNA polymerase gene mutant library.

(4) The T7 RNA polymerase mutant library produced was transformed into E. coli strain JM109 containing plasmid pSTVGFP (FIG. 5) produced in Example 4, and after incubating the transformants for 1 hour at 37° C. in SOC medium, those strains that grew in LBG/Crb/Cm agar medium (1% polypeptone, 0.5% yeast extract, 1% NaCl, 0.5% glucose, 50 μg/mL carbenicillin, 30 μg/mL chloramphenicol, 1.5% agar) and emitted GFP fluorescence were designated as mutant candidate strains. Furthermore, a portion of the produced library was transformed into E. coli strain JM109 in accordance with established methods and the plasmids were purified therefrom, and then the effect of error-prone PCR was confirmed by base sequencing using the method indicated in Example 6.

Example 16

Screening of High-Temperature T7 RNA Polymerase (Part 2)

Screening of the mutant strains obtained in Example 15 was carried out using the same method as Example 5. As a result of screening, 34 strains were obtained from about 4000 mutant strains that demonstrated specific activity roughly twice as high as that of the mutant (K179E+Q786L) T7 RNA polymerase produced in Example 8, and these strains were designated as primary candidate strains. Moreover, the primary candidate screens were re-screened using the same method as Example 5, and as a result thereof, one strain was selected that demonstrated specific activity more than twice as high as that of the (K179E+Q786L) T7 RNA polymerase mutant.

Example 17

Base Sequence Analysis of Selected Strain

Mutation sites were confirmed by confirming the base sequence of the bacterial strains selected in Example 16 using the method described in Example 6. As a result, thymine at position 2054 of the base sequence was substituted with cytosine, GTG codon was substituted with GCG codon and valine at position 685 of the amino acid sequence was determined to have mutated to alanine. T7 RNA polymerase harboring this mutation was designated as mutant (K179E+Q786L+V685A), its gene sequence is shown in SEQ ID NO: 43, and its amino acid sequence is shown in SEQ ID NO: 44.

Example 18

Production of (K179E+Q786L+V685A) T7 RNA Polymerase Mutant

An enzyme was produced according to the following procedure using E. coli strain JM109 expressing the (K179E+Q786L+V685A) T7 RNA polymerase triple mutant having a histidine hexamer sequence obtained in Example 16.

(1) Glycerol stock cultures of the bacterial strains obtained in Example 16 were inoculated into 40 mL of LBG/Crb broth medium (1% polypeptone, 0.5% yeast extract, 1% NaCl, 0.5% glucose, 50 μg/mL carbenicillin (pH 7.4)) and shake-cultured overnight at 37° C. in a 100 mL volumetric fluted Erlenmeyer flask.

(2) 30 mL of the pre-culture broth were inoculated into 1.5 L of 2xYTG/Crb medium (1.6% Bacto tryptone, 1% Bacto yeast extract, 0.5% NaCl, 0.5% glucose, 50 μg/mL carbenicillin (pH 7.4)) followed by culturing at 37° C. in a 3 L volumetric fermentation tank.

(3) After continuing the culturing of (2) for about 3 hours (to an OD$_{600\ nm}$ value of about 2.0), 1.5 mL of 500 mM IPTG (isopropyl-β-thiogalactopyranoside) were added followed by lowering the temperature to 30° C. and further culturing for 3 hours. The enzyme concentration in the culture was adjusted to 1.6 ppm or more and the pH was adjusted to a range of 6.8 to 7.2.

(4) Following completion of culturing, 21 g of wet bacterial cells were obtained by centrifuging for 15 minutes at 4° C. and 7000 rpm. The cells were washed with 100 mL of 20 mM potassium phosphate buffer solution (pH 7.0), and stored at −30° C. unless in the case not immediately carrying out the next treatment.

(5) Half of the recovered cells were suspended in 42 mL of 20 mM potassium phosphate buffer solution (pH 7.0) containing 0.1 mM PMSF and 1 mM EDTA to lyse the cells. Cell lysis was carried out by treating for about 5 minutes at 5° C. and an output of about 150 W using an ultrasonic generator (Insonator 201M (trade name), Kubota), and a soluble fraction was recovered by centrifuging for 10 minutes at 4° C. and 12000 rpm.

(6) 5.1 mL of 2 M ammonium sulfate and 0.95 mL of 10% polyethyleneimine were respectively added to 45 mL of the recovered fraction, and after refrigerating for about 1 hour at 0° C., supernatant was recovered by centrifuging for 10 minutes at 4° C. and 12000 rpm.

(7) Using a portion of the recovered supernatant, the supernatant was purified by affinity chromatography using the histidine hexamer tag in compliance with the method indicated in Example 7.

The protein concentration of the purified T7 RNA polymerase was determined according to optical absorbance at 280 nm. In addition, enzyme protein purity was analyzed by SDS-PAGE at concentrations from 5% to 20%, and the enzyme was confirmed to essentially only consist of a single protein.

Example 19

Evaluation of T7 RNA Polymerase Mutant Activity (Part 3)

Evaluation of the activity of the (K179E+Q786L+V685A) T7 RNA polymerase triple mutant produced in Example 18 was carried out using the method indicated in Example 7 consisting of measuring the amount of RNA formed by an in vitro transcription reaction. Furthermore, the transcription reaction temperature was set to a range of 43 to 50° C., the amount of T7 RNA polymerase was set to 10 ng/μL, and the reaction time was set to 30 minutes. In addition, the (K179E+Q786L) T7 RNA polymerase double mutant produced in Example 8 and wild-type T7 RNA polymerase were used as controls.

Figure 11:
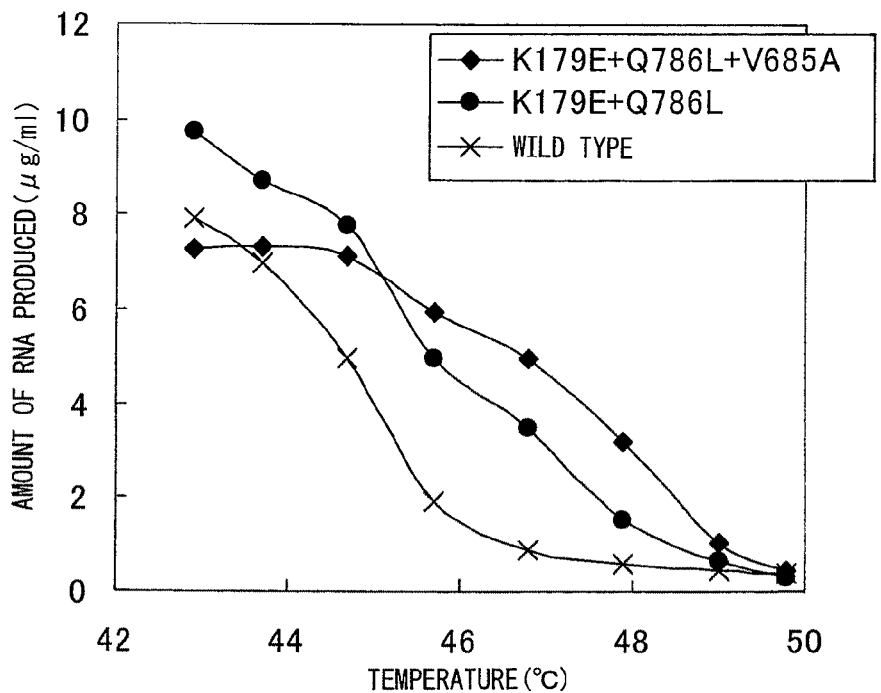
FIG. 11 shows the results of comparing RNA production amounts at 43 to 50° C. between wild-type T7 RNA polymerase, a double mutant (K179E+Q786L) and a triple mutant (K179E+Q786L+V685A), respectively.

The amounts of RNA formed at each temperature are shown in FIG. 11. It can be determined from FIG. 11 that the triple mutant (K179E+Q786L+V685A) demonstrates higher specific activity at a reaction temperature of 46° C. or higher than the original double mutant (K179E+Q786L).

Example 20

Evaluation of Thermal Stability of T7 RNA Polymerase Mutant (Part 3)

The thermal stabilities of each of the T7 RNA polymerase mutants and the wild type were measured according to the following method.
(1) The (K179E+Q786L+V685A) T7 RNA polymerase triple mutant produced in Example 18, the (K179E+Q786L) T7 RNA polymerase double mutant produced in Example 8, and wild-type T7 RNA polymerase were adjusted to 100 μg/mL using a buffer having the composition indicated below, and after dispensing 25 μL aliquots thereof into 0.2 mL PCR tubes, were heat-treated for 1, 2, 5, 10 and 20 minutes at 48° C.

(Buffer Composition)

| Tris-HCl buffer (pH 8.0) | 40 mM |
| MgCl$_2$ | 20 mM |
| Dithiothreitol | 5 mM |
| KCl | 70 mM |
| Bovine serum albumin | 0.01 mg/mL |

(2) Activities were measured by carrying out transcription reactions for 30 minutes at 43° C. using the heat-treated solutions, and the value obtained by dividing the activity for each treatment time by the activity prior to heating was defined as residual activity.

Figure 12:
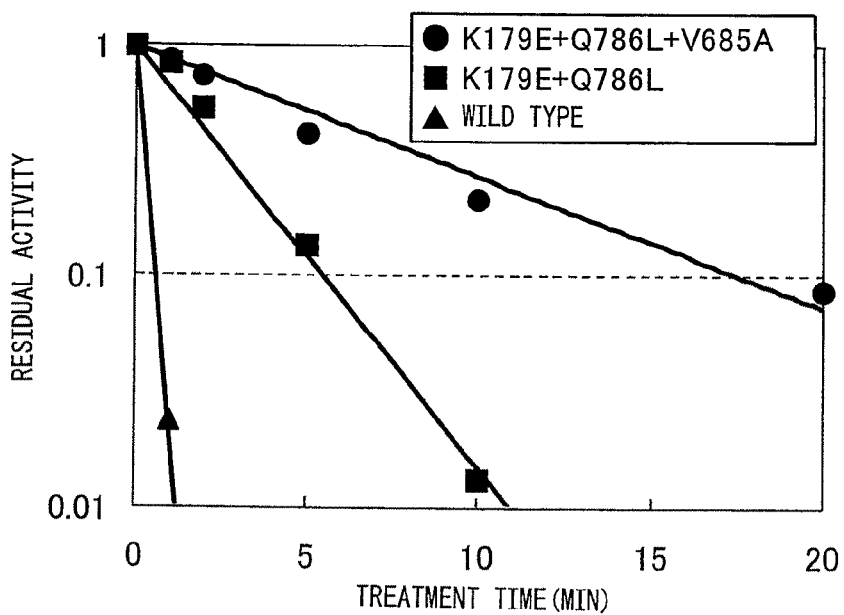
FIG. 12 shows the results of comparing thermal stability against heating at 48° C. between wild-type T7 RNA polymerase, a double mutant (K179E+Q786L) and a triple mutant (K179E+Q786L+V685A), respectively.

A graph of residual activity is shown in FIG. 12. In addition, the results of determining the half-lives of each type of T7 RNA polymerase mutant and the wild type from the slope of the graph of FIG. 12 are shown in Table 2. According to Table 2, the half-life of the (K179E+Q786L+V685A) T7 RNA polymerase triple mutant was found to be longer than that of the (K179E+Q786L) T7 RNA polymerase double mutant and the wild type, thereby demonstrating superior thermal stability at 48° C.

TABLE 2

| T7 RNA Polymerase | Half-life (min) |
|---|---|
| Mutant (K179E + Q786L + V685A) | 5.3 |
| Mutant (K179E + Q786L) | 1.7 |
| Wild type | <1 |

Example 21

Production of (Q786L+M685A) T7 RNA Polymerase Mutant

A (Q786L+V685A) T7 RNA polymerase double mutant was produced from the (K179E+Q786L+V685A) T7 RNA polymerase triple mutant produced in Example 18 according to the method indicated below.
(1) A pCDF2-T7RNAPHis (K179E+Q786L+V685A) plasmid inserted with a gene encoding the (K179E+Q786L+V685A) T7 RNA polymerase triple mutant, and a plasmid pCDF2-T7RNAP (FIG. 3) inserted with a gene encoding wild-type T7 RNA polymerase were prepared using a miniprep method.
(2) 200 ng of both plasmids were digested with restriction enzymes KpnI and SadI according to ordinary methods, and after subjecting to agarose gel electrophoresis, a wild-type 4.5 kbp fragment and a mutant (K179E+Q786L+V685A) 1.4 kbp fragment were purified by gel extraction.
(3) 40 ng of the purified wild-type fragment and 80 ng of the mutant (K179E+Q786L+V685A) fragment were reacted for 30 minutes at 16° C. using T4 ligase and transformed into E. coli strain JM109 in accordance with ordinary methods.
(4) The transformant was selected on LBG/Crb agar medium (1% polypeptone, 0.5% yeast extract, 1% NaCl, 0.5% glucose, 1.5% agar, 50 μg/mL carbenicillin (pH 7.4)), and plasmid was prepared from those colonies that grew after incubating overnight at 37° C.

The plasmid prepared in (4) was confirmed to be inserted with the target mutation according to the base sequencing method indicated in Example 6. The gene sequence of the plasmid is shown in SEQ ID NO: 45, while the amino acid sequence is shown in SEQ ID NO: 46.

Example 22

Purification of Mutant (Q786L+V685A) T7 RNA Polymerase

A (Q786L+V685A) T7 RNA polymerase mutant was prepared according to the following method using E. coli strain JM109 expressing the (Q786L+V685A) T7 RNA polymerase double mutant produced in Example 21.
(1) Culturing was carried out according to the procedure indicated in Example 18 to obtain 28 g of wet bacterial cells.
(2) The resulting cells were suspended in 112 mL of 20 mM potassium phosphate buffer solution (pH 7.0) containing 0.1 mM PMSF and 20 mM EDTA followed by ultrasonically lysing the cells and obtaining a supernatant by centrifugal separation.
(3) 17.5 mL of 2 M ammonium sulfate and 3.5 mL of 10% polyethyleneimine were added to 135 mL of the resulting enzyme extract, and after refrigerating for about 1 hour at 0° C., the supernatant was recovered by centrifugal separation.
(4) 51 g of ammonium sulfate were added to 130 mL of the recovered supernatant, and after refrigerating for 1 hour at 0° C., the precipitate recovered by centrifugal separation was dissolved in 30 mL of a buffer solution having the composition indicated below.
(Buffer Composition)

| Potassium phosphate buffer (pH 7.6) | 20 mM |
| Dithiothreitol | 1 mM |

-continued

| | |
|---|---|
| PMSF | 0.1 mM |
| EDTA | 1 mM |

(5) The precipitate solution prepared in (4) was purified by high-performance liquid chromatography according to the following method.
(5-1) Purification was carried out under the following conditions using a hydrophobic column (TSKgel Phenyl-5PW (trade name), Tosoh Corp.).
(Purification Conditions)
Eluent A:

| | |
|---|---|
| Potassium phosphate buffer (pH 7.2) | 20 mM |
| NaCl | 50 mM |
| Ammonium sulfate | 0.6M |
| DTT | 1 mM |
| EDTA | 1 mM |

Eluent B:
Composition of eluent A excluding ammonium sulfate
Gradients:
0 to 60 minutes: 100% eluent A
60 to 120 minutes: linear gradient from 100% to 0% eluent A
120 to 130 minutes: 0% eluent A
130 minutes: Stepwise gradient from 0% to 100% eluent A
Detection: 280 nm
Flow rate: 4 mL/min
(5-2) 100 mL of a fraction containing a large amount of T7 RNA polymerase were recovered by SDS-PAGE and salted-out with 39 g of ammonium sulfate.
(5-3) The salted-out precipitate recovered by centrifugal separation was dissolved in 5 mL a buffer solution having the composition indicated below.
(Buffer Composition)

| | |
|---|---|
| Potassium phosphate buffer (pH 7.6) | 20 mM |
| Dithiothreitol | 1 mM |
| PMSF | 0.1 mM |
| EDTA | 1 mM |

(5-4) The resulting solution was dialyzed overnight at 4° C. in a buffer solution of the same composition using a dialysis membrane having a cutoff molecular weight of 12000, and then purified with an ion exchange column (TSKgel DEAE-5PW (trade name), Tosoh Corp.) under the following conditions.
(Purification Conditions)
Eluent A:

| | |
|---|---|
| Potassium phosphate buffer (pH 7.6) | 20 mM |
| NaCl | 50 mM |
| Dithiothreitol | 1 mM |
| EDTA | 1 mM |

Eluent B:
Composition of eluent A with the exception of changing NaCl concentration to 0.8 M
Gradients:
0 to 20 minutes: 100% eluent A
20 to 80 minutes: Linear gradient from 100% to 0% eluent A
80 to 90 minutes: 0% eluent A
90 minutes: Stepwise gradient from 0% to 100% eluent A
Detection: 280 nm
Flow rate: 4 mL/min
(5-5) A fraction being analyzed to contain a large amount of T7 RNA polymerase by SDS-PAGE was recovered and salted-out with 1.95 g of ammonium sulfate.
(5-6) The salted-out precipitate was dissolved in 1 mL of a buffer used for gel filtration purification and purified under the following conditions using a gel filtration column (TSKgel G3000SW (trade name), Tosoh Corp.).
(Purification Conditions)
Eluent:

| | |
|---|---|
| Potassium phosphate buffer (pH 7.6) | 40 mM |
| NaCl | 200 mM |
| Dithiothreitol | 2 mM |
| EDTA | 0.2 mM |
| Detection: | 280 nm |
| Flow rate: | 5 mL/min |

(5-7) 4 mL of a fraction containing a large amount of T7 RNA polymerase based on analysis by SDS-PAGE were recovered.
(5-8) After salting-out the recovered fraction with 1.56 g of ammonium sulfate, the buffer was replaced with a buffer having the same composition as that used for gel filtration column purification using a salting-out column (PD-10 (trade name), GE Healthcare Bio Sciences), followed by adding an equal volume of glycerol to bring to a volume of 2.5 mL.
When the protein concentration of the purified T7 RNA polymerase double mutant was determined according to optical absorbance at 280 nm, it was found to be 1.9 mg/mL. In addition, the purified T7 RNA polymerase double mutant was confirmed to consist of essentially a single band by analyzing enzyme proteins with SDS-PAGE at concentrations from 5 to 20%.

Example 23

Nucleic Acid Amplification Reaction by T7 RNA Polymerase Mutant

Nucleic acid amplification was measured by TRC using the (Q786L+M685A) T7 RNA polymerase double mutant prepared in Example 22 according to the following method by using *Salmonella* toxin gene (stn RNA) as the target RNA. Furthermore, wild-type T7 RNA polymerase was used as a control.
(1) An stn RNA positive standard (concentration: $10^6$ copies/5 μL) appended to a *Salmonella* stn mRNA detection reagent (TRCRtest stn-m (trade name), Tosoh Corp.) was diluted to $10^4$ copies/5 μL with RNA diluent (10 mM Tris-HCl buffer (pH 8.0), 1 mM EDTA, 0.5 U/mL RNase inhibitor, 5 mM dithiothreitol). Only the RNA diluent was used in a control test (negative control).
(2) 20 μL of a reaction solution having the following composition was dispensed into a 0.5 mL volumetric PCR tube followed by the addition of 5 μL of the aforementioned RNA sample thereto.
(Reaction Solution Composition) (concentration or amount in 30 μL of final reaction solution)

| | |
|---|---|
| Tris-HCl buffer (pH 8.6) | 60 mM |
| MgCl$_2$ | 17 mM |
| KCl | 100 mM |
| RNase inhibitor | 6 U |
| Dithiothreitol | 1 mM |
| dATP, dCTP, dGTP, dTTP | 0.25 mM each |
| ITP | 3.6 mM |
| ATP, CTP, GTP, UTP | 3.0 mM each |
| Cleaving oligonucleotide (SEQ ID NO: 47, amination of hydroxyl group of 3'-terminal) | 0.12 µM |
| First primer (SEQ ID NO: 48) | 1.0 µM |
| Second primer (SEQ ID NO: 49) | 1.0 µM |
| Nucleic acid probe labeled with intercalating fluorescent pigment (SEQ ID NO: 50, intercalating fluorescent pigment labeled between "A" at position 12 and "A" at position 13 of 5'-terminal, and hydroxyl group on 3'-terminal modified with a glycol group) | 7.5 nM |
| DMSO | 1% |

Distilled water for adjusting volume

Distilled Water for Adjusting Volume (3) After heating the mutant at temperatures of 49° C., 50° C. and 51° C. and the wild type at temperatures of 43° C. and 49° C. for 5 minutes in the reaction solution of (2), 5 µL of an enzyme solution pre-heated for 2 minutes at each temperature and having the composition indicated below were added.

(Enzyme Solution Composition) (concentration or amount in 30 µL of final reaction solution)

| | |
|---|---|
| Sorbitol | 2% |
| Bovine serum albumin | 3.6 µg |
| AMV reverse transcriptase (Life Science) | 4 U |
| T7 RNA polymerase | 46 U |

Distilled water for adjusting volume (4) PCR tubes were heated at each temperature and the absorbance of the reaction solution was measured over time at an excitation wavelength of 470 nm and emission wavelength of 510 nm using a fluorescent photometer equipped with a temperature control function capable of direct measurement.

Figure 13:
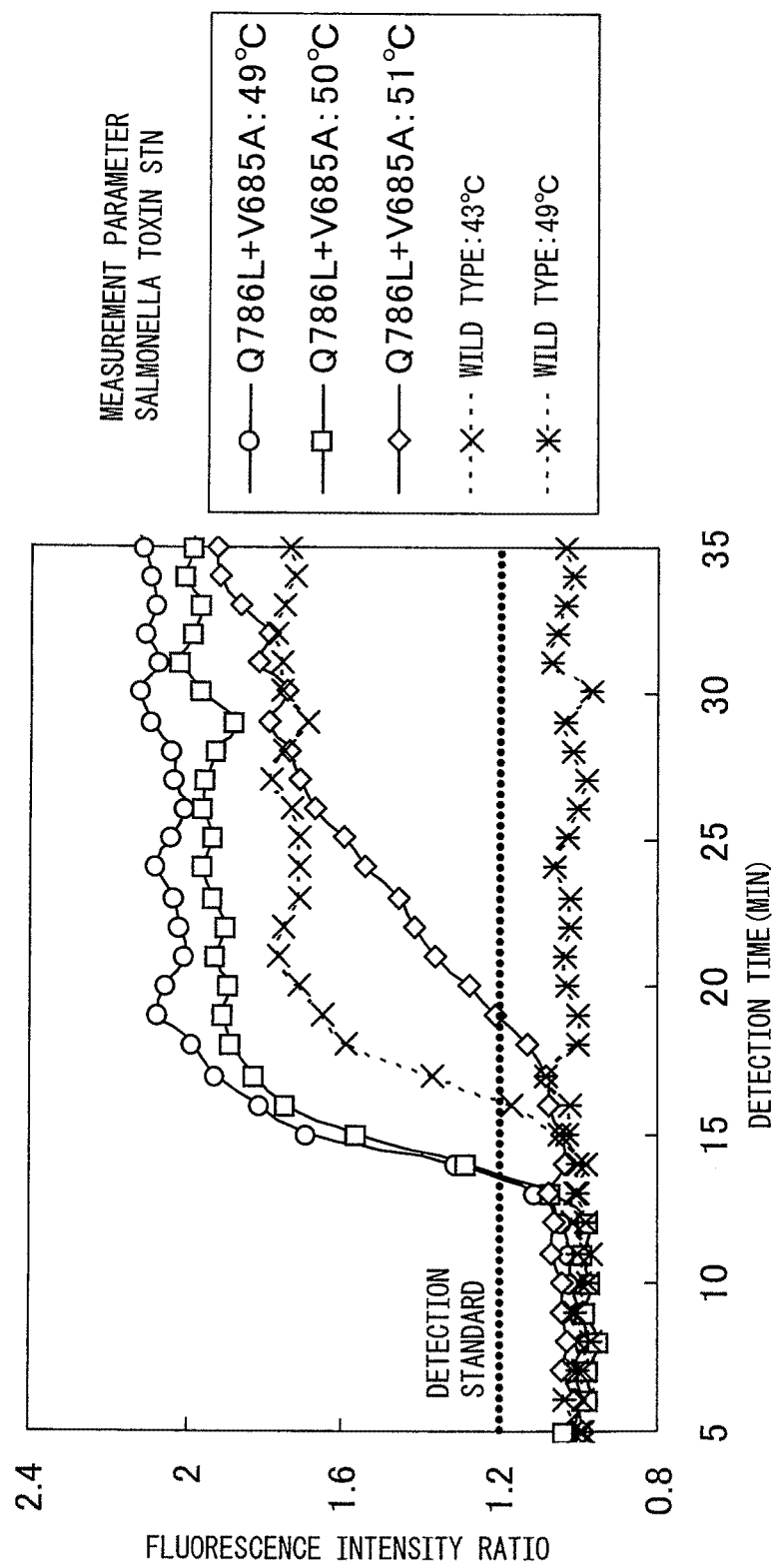
FIG. 13 shows the results of carrying out isothermal nucleic acid amplification by TRC on *Salmonella* stn RNA using wild-type T7 RNA polymerase and a double mutant (Q786L+V685A).

The time-based changes in fluorescence intensity ratio (value obtained by dividing the fluorescence intensity value at a prescribed time by a background fluorescence intensity value) of the reaction solution are shown in FIG. 13 by assigning a value of 0 minutes to the time of enzyme addition. In contrast to amplification of stn RNA not being observed during a reaction temperature of 49° C. when the wild-type T7 RNA polymerase was used, stn RNA amplification was observed even at a reaction temperature of 51° C. for the double mutant (Q786L+V685A). On the basis thereof, the double mutant (Q786L+V685A) was determined to have superior thermal stability and/or specific activity at high temperatures of 49 to 51° C. in comparison with wild-type T7 RNA polymerase.

Example 24

Measurement of Minimum Detected Concentration of Nucleic Acid Amplification Reaction by T7 RNA Polymerase Mutant The minimum detected concentration of the (Q786L+V685A) T7 RNA polymerase double mutant prepared in Example 22 was confirmed relative to stn mRNA standard RNA.

The measurement method consisted of the same method used in Example 23 with the exception of changing the reaction temperature to 50° C. (double mutant) or 43° C. (wild type), and changing the concentration of the target RNA to 10, 50, 100, 300, 500 and 1000 copies/5 µL.

Detection rates of the (Q786L+V685A) T7 RNA polymerase double mutant and the wild-type T7 RNA polymerase for their respective initial number of RNA copies are shown in Table 3. According to Table 3, the stn RNA detection rate when using the double mutant (Q786L+V685A) was higher than the detection rate of the wild type at 43° C., and when a comparison is made of the minimum RNA concentrations that exhibit a detection rate of 80% or higher, the minimum RNA concentration of the double mutant (Q786L+V685A) was 200 copies/5 µL in contrast to 1000 copies/5 µL for the wild type. In the case of comparing at the optimum temperature conditions of both enzymes, the double mutant (Q786L+V685A) was determined to have improved sensitivity that was about 5 times greater than that of the wild type.

TABLE 3

| Recombinant Used | Reaction Temperature | Detection Rates for Initial No. of Copies (copies/test) (%) | | | | | | |
|---|---|---|---|---|---|---|---|---|
| | | 0 | 50 | 100 | 200 | 300 | 500 | 1000 |
| Wild type | 43° C. | 0 | 0 | 13 | 43 | 50 | 63 | 100 |
| Double mutant (Q786L + V685A) | 50° C. | 0 | 38 | 63 | 88 | 86 | 100 | 100 |

Example 25

Production of V685 T7 RNA Polymerase Mutant

A T7 RNA polymerase mutant, in which valine at position 685 of the amino acid sequence had mutated to alanine (mutant V685A), was produced according to the following procedure from T7 RNA polymerase gene of the pCDF-T7RNAPHis plasmid (FIG. 4) produced in Example 2.

(1) A PCR reaction was carried out using pCDF2-T7RNAPHis (FIG. 4) as a template plasmid with the following reagent composition and under the following reaction conditions. Furthermore, a combination of primer V685AF (SEQ ID NO: 51) and primer pTrcRs (SEQ ID NO: 16) or a combination of primer pCDFF4 (SEQ ID NO: 42) and primer V685AR (SEQ ID NO: 53) was used as synthetic primers.

(Reagent Composition) (total reaction solution volume: 50 µL)

| | |
|---|---|
| Synthetic DNA primers | 100 pM each |
| Template plasmid | 50 ng |
| dNTPs | 0.1 mM |
| DNA polymerase (PrimeSTAR HS DNA polymerase (trade name), Takara Bio) | 0.025 unit/µL |

Buffer provided for the enzyme (Reaction Conditions)

After initially heating for 30 seconds at 96° C., a temperature cycle consisting of 30 seconds at 96° C., 30 seconds at 50° C. and 1 minute at 72° C. was repeated 30 times using a thermal cycler (Perkin-Elmer).

(2) The reaction solution was purified by subjecting it to 1% agarose gel electrophoresis, staining the gel with ethidium bromide and cutting out bands of the target products from the stained gel.

(3) A PCR reaction was further carried out using the two types of purified PCR products obtained in (2) as templates to produce mutant V685A gene. Furthermore, the reaction composition, reaction conditions and purification procedure of the PCR reaction were the same as (1) and (2) with the exception of using the combination of primer pCDFF4 (SEQ ID NO: 42) and primer pTrcRs (SEQ ID NO: 16) as synthetic DNA primers.

(4) The DNA fragments obtained in (3) were digested with restriction enzymes HindIII and KpnI (Takara Bio) and then reacted for 30 minutes at 4° C. with the pCDF2-T7RNAPHis vector digested with the same enzymes using T4 ligase.

(5) The reaction solution of (4) was transformed into *E. coli* strain JM109, selection was carried out on LBG/Crb agar medium (1% polypeptone, 0.5% yeast extract, 1% NaCl, 0.5% glucose, 1.5% agar, 50 μg/mL carbenicillin (pH 7.4)), and those colonies that grew after culturing overnight at 37° C. were designated as mutant V685A. Moreover, mutant V685A was confirmed to have been introduced with the mutation according to the base sequencing method indicated in Example 6. The gene sequence thereof is shown in SEQ ID NO: 54, while the amino acid sequence is shown in SEQ ID NO: 55.

Example 26

Purification and Evaluation of Activity of V685A T7 RNA Polymerase Mutant

Preparation and evaluation of activity of a V685A T7 RNA polymerase mutant were carried out according to the method indicated in Example 7 using *E. coli* strain JM109 expressing the V685A T7 RNA polymerase mutant produced in Example 25. Furthermore, the transcription reaction temperature was set to 43 to 49° C., the amount of T7 RNA polymerase was set to 20 ng/μL, and the reaction time was set to 30 minutes. In addition, wild-type T7 RNA polymerase was used as a control.

Figure 14:
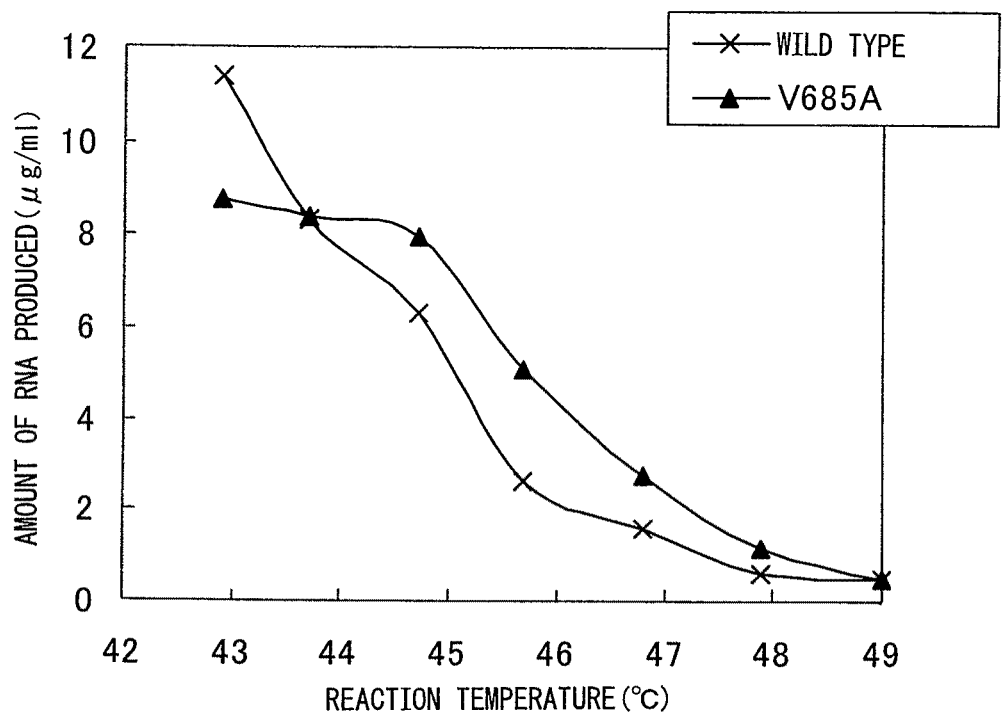
FIG. 14 shows the results of comparing RNA production amounts at 43 to 49° C. between wild-type T7 RNA polymerase and a mutant V685A, respectively.

The amounts of RNA formed at each temperature are shown in FIG. 14. It was determined from FIG. 14 that V685A T7 RNA polymerase mutant demonstrates a larger amount of RNA produced at a reaction temperature of 45° or higher and improved specific activity at high temperatures as compared with the wild type.

Example 27

Evaluation of Thermal Stability of V685A T7 RNA Polymerase Mutant

Thermal stability of the V685A T7 RNA polymerase mutant was evaluated according to the method indicated in Example 20 using the V685A T7 RNA polymerase mutant prepared in Example 26. Furthermore, the heat treatment temperature was set to 46° C., and the treatment times were set to 1, 2 and 5 minutes. In addition, wild-type T7 RNA polymerase was used as a control.

Figure 15:
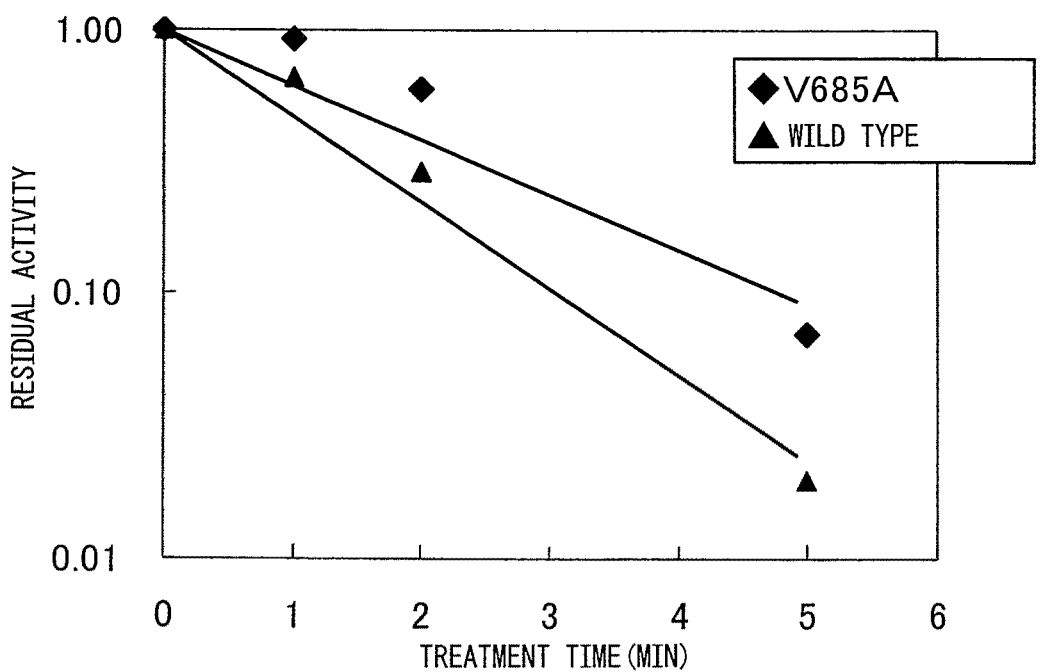
FIG. 15 shows the results of comparing thermal stability against heating at 46° C. between wild-type T7 RNA polymerase and a mutant V685A, respectively.

A graph of residual activity is shown in FIG. 15. In addition, the results of determining the half-lives of the V685A T7 RNA polymerase mutant and the wild type from the slope of the graph of FIG. 15 are shown in Table 4. According to Table 4, the half-life of the V685A T7 RNA polymerases mutant was found to be longer than that of the wild type, thereby demonstrating superior thermal stability at 46° C.

TABLE 4

| T7 RNA Polymerase | Half-life (min) |
|---|---|
| Mutant V685A | 1.4 |
| Wild type | 0.9 |

Example 28

Production of (V685A+Q786M) T7 RNA Polymerase Mutant

A (V685A+Q786M) T7 RNA polymerase double mutant, in which glutamine at position 786 of the amino acid sequence had further mutated to methionine, was produced according to the following method using the pCDF-T7RNAPHis plasmid (FIG. 4) introduced with the V685A T7 RNA polymerase mutant gene produced in Example 25.

(1) A PCR reaction was carried out using pCDF2-T7RNAPHis of mutant V685A as a template plasmid with the following reagent composition and under the following reaction conditions. Furthermore, a combination of primer Q786MF (SEQ ID NO: 56) and primer pTrcRs (SEQ ID NO: 16) or a combination of primer pCDFF4 (SEQ ID NO: 42) and primer Q786MR (SEQ ID NO: 57) was used as synthetic primers.

(Reagent Composition) (total reaction solution volume: 50 μL)

| Synthetic DNA primers | 100 pM each |
|---|---|
| Template plasmid | 50 ng |
| dNTPs | 0.1 mM |
| DNA polymerase (PrimeSTAR HS DNA polymerase (trade name), Takara Bio) | 0.025 unit/μL |

Buffer provided for the enzyme (Reaction Conditions)

After initially heating for 30 seconds at 96° C., a temperature cycle consisting of 30 seconds at 96° C., 30 seconds at 50° C. and 1 minute at 72° C. was repeated 30 times using a thermal cycler (Perkin-Elmer).

(2) The reaction solution was purified by subjecting it to 1% agarose gel electrophoresis, staining the gel with ethidium bromide and cutting out bands of the target products from the stained gel.

(3) A PCR reaction was further carried out using the two types of purified PCR products obtained in (2) as templates to produce mutant (V685A+Q786M) gene. Furthermore, the reaction composition, reaction conditions and purification procedure of the PCR reaction were the same as (1) and (2) with the exception of using the combination of primer pCDFF4 (SEQ ID NO: 42) and primer pTrcRs (SEQ ID NO: 16) as synthetic DNA primers.

(4) The DNA fragments obtained in (3) were digested with restriction enzymes HindIII and KpnI (Takara Bio) and then reacted for 30 minutes at 4° C. with the pCDF2-T7RNAPHis vector digested with the same enzymes using T4 ligase.

(5) The reaction solution of (4) was transformed into E. coli strain JM109, selection was carried out on LBG/Crb agar medium (1% polypeptone, 0.5% yeast extract, 1% NaCl, 0.5% glucose, 1.5% agar, 50 μg/mL carbenicillin (pH 7.4)), and those colonies that grew after culturing overnight at 37° C. were designated as mutant (V685A+Q786M). Moreover, mutant (V685A+Q786M) was confirmed to have been introduced with the mutation according to the base sequencing method indicated in Example 6. The gene sequence thereof is shown in SEQ ID NO: 58, while the amino acid sequence is shown in SEQ ID NO: 59.

Example 29

Purification and Evaluation of Activity of (V685A+Q786M) T7 RNA Polymerase Mutant Preparation and evaluation of activity of the (V685A+Q786M) T7 RNA polymerase mutant were carried out according to the method indicated in Example 7 using E. coli strain JM109 expressing the (V685A+Q786M) T7 RNA polymerase mutant produced in Example 28. Furthermore, the transcription reaction temperature was set to 43 to 50° C., the amount of T7 RNA polymerase was set to 20 ng/μL, and the reaction time was set to 30 minutes. In addition, wild-type T7 RNA polymerase was used as a control.

Figure 16:
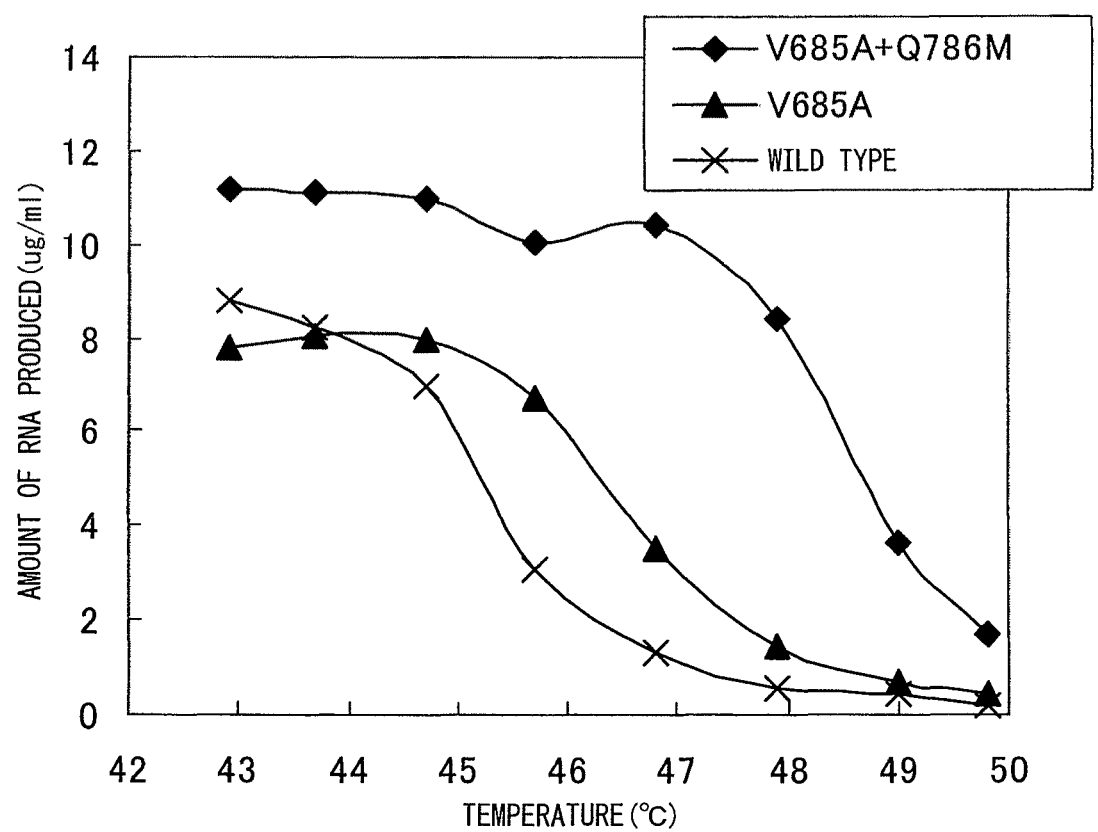
FIG. 16 shows the results of comparing RNA production amounts at 43 to 50° C. between wild-type T7 RNA polymerase, a mutant V685A and a double mutant (V685A+Q786M), respectively.

The amounts of RNA formed at each temperature are shown in FIG. 16. It was determined from FIG. 16 that (V685A+Q786M) T7 RNA polymerase mutant demonstrates a larger amount of RNA produced at a reaction temperature of 45° or higher and improved specific activity at high temperatures as compared with the wild type.

The invention claimed is:

1. A mutant T7 RNA polymerase characterized by having improved thermal stability and/or specific activity in comparison with the wild-type T7 bacteriophage RNA polymerase, wherein said mutant T7 RNA polymerase comprises the amino acid sequence of SEQ ID NO: 6 in which one or more residues are substituted with another amino acid, said one or more residues being selected from the group consisting of positions 786, 179 and 685 of SEQ ID NO: 6.

2. The mutant T7 RNA polymerase of claim 1, wherein said mutant has a substitution at position 786 in SEQ ID NO: 6, and wherein said substitution at position 786 in SEQ ID NO: 6 is with a hydrophobic amino acid.

3. The mutant T7 RNA polymerase of claim 1, wherein said mutant has a substitution at position 786 in SEQ ID NO: 6, and wherein said substitution at position 786 in SEQ ID NO: 6 is with leucine or methionine.

4. The mutant T7 RNA polymerase according to claim 2, wherein said mutant has a further substitution at position 179 in SEQ ID NO: 6, and wherein said substitution at position 179 in SEQ ID NO: 6 is with glutamate, asparagine or cysteine.

5. The mutant T7 RNA polymerase of claim 1, wherein said mutant has a substitution at position 179 in SEQ ID NO: 6, and wherein said substitution at position 179 in SEQ ID NO: 6 is with glutamate, asparagine or cysteine.

6. The mutant T7 RNA polymerase according to claim 2, wherein said mutant has a substitution at position 685 in SEQ ID NO: 6, and wherein said substitution at position 685 in SEQ ID NO: 6 is with a neutral or weakly hydrophobic amino acid.

7. The mutant T7 RNA polymerase according to claim 6, wherein said substitution at position 685 in SEQ ID NO: 6 is with alanine.

8. The mutant T7 RNA polymerase of claim 1, wherein said mutant has a substitution at position 685 in SEQ ID NO: 6, and wherein said substitution at position 685 in SEQ ID NO: 6 is with a neutral or weakly hydrophobic amino acid.

9. The mutant T7 RNA polymerase of claim 8, wherein the substitution at position 685 in SEQ ID NO: 6 is with alanine.

10. The mutant T7 RNA polymerase of claim 1, wherein said mutant has a substitution at position 685 in SEQ ID NO: 6, and a further substitution(s) at either or both of positions 179 and 786 in SEQ ID NO: 6.

11. The mutant T7 RNA polymerase of claim 10, wherein the substitution at position 685 is with alanine, the substitution at position 179 is with glutamate, and the substitution at position 786 is with leucine or methionine.

* * * * *